(12) United States Patent
Kadokawa et al.

(10) Patent No.: US 8,575,131 B2
(45) Date of Patent: Nov. 5, 2013

(54) GLUCURONIC ACID-CONTAINING GLUCAN, PROCESS FOR PRODUCTION OF SAME, AND USE OF SAME

(75) Inventors: Junichi Kadokawa, Kagoshima (JP); Takeshi Takaha, Osaka (JP); Akiko Kubo, Osaka (JP); Michiyo Yanase, Osaka (JP); Kayo Hosoya, Osaka (JP)

(73) Assignees: National University Corporation Kagoshima University, Kagoshima (JP); Ezaki Glico Co., Ltd., Osaka (JP)

( * ) Notice: Subject to any disclaimer, the term of this patent is extended or adjusted under 35 U.S.C. 154(b) by 50 days.

(21) Appl. No.: 13/318,958

(22) PCT Filed: May 10, 2010

(86) PCT No.: PCT/JP2010/003182
§ 371 (c)(1),
(2), (4) Date: Jan. 27, 2012

(87) PCT Pub. No.: WO2010/128601
PCT Pub. Date: Nov. 11, 2010

(65) Prior Publication Data
US 2012/0135063 A1    May 31, 2012

(30) Foreign Application Priority Data
May 8, 2009    (JP) .................................. 2009-113754

(51) Int. Cl.
*A61K 31/70*    (2006.01)
*C07H 1/00*    (2006.01)

(52) U.S. Cl.
USPC ...................................... 514/54; 536/123.12

(58) Field of Classification Search
USPC ............................... 536/1.11, 123.12; 514/54
See application file for complete search history.

(56) References Cited

FOREIGN PATENT DOCUMENTS

JP    2005-015680    1/2005

OTHER PUBLICATIONS

International Search Report for corresponding International Application No. PCT/JP2010/003182 mailed Jul. 13, 2010.
Form PCT/ISA/237 for corresponding International Application No. . PCT/JP2010/003182 dated Jul. 13, 2010.
Umegaya et al., "Tainetsusei Phosphorylase ni yoru Glucron-san Zanki no Maltooligo-to eno Ten'i Hanno", CSJ: The Chemical Socity of Japan Koen Yokoshu, Mar. 12, 2010, vol. 90, p. 1033.
Dean et al., Identification of UGT2B9*2 and UGT2B33 isolated from female rhesus monkey liver, Archives of Biochemistry and Biophysics, 2004, vol. 426, p. 55-62.
Nawaji et al., Enzymatic α-glucosaminylation of maltooligosaccharides catalyzed by phosphorylase, Carbohydr Research, 2008, vol. 343, p. 2692-2696.
Nawaji et al., Enzymatic Synthesis of α-D-Xylosylated Maltooligosaccharides by Phosphyorylase-catalyzed Xylosylation, Journal of Carbohydrate Chemistry, 2008, vol. 27, p. 214-222.

*Primary Examiner* — Elli Peselev
(74) *Attorney, Agent, or Firm* — Renner, Otto, Boisselle & Sklar, LLP

(57) ABSTRACT

An object of the present invention is to provide a uronic acid-containing glucan or a modified product thereof. The glucuronic acid-containing glucan of the present invention is a glucuronic acid-containing glucan in which a glucuronic acid residue is bound to at least one non-reducing end of a glucan, and the glucan is a branched α-1,4 glucan or a linear α-1,4 glucan. The glucuronic acid-containing glucan of the present invention can be provided by allowing α-glucan phosphorylase derived from *Aquifex aeolicus* VF5 to act on glucuronic acid-1-phosphate to thereby transfer a glucuronic acid residue to the non-reducing end of the receptor glucan.

17 Claims, 14 Drawing Sheets

GLUCURONIC ACID-CONTAINING GLUCAN, PROCESS FOR PRODUCTION OF SAME, AND USE OF SAME

This application is a national phase of International Application No. PCT/JP2010/003182 filed May 10, 2010.

TECHNICAL FIELD

The present invention relates to a glucan having a uronic acid residue on a non-reducing end, a modified product and a conjugate thereof, as well as a method for producing the same, and utilization of the same. More particularly, the present invention relates to a glucan having a glucuronic acid residue on a non-reducing end, a modified product and a conjugate thereof, as well as a method for producing the same, and utilization of the same.

BACKGROUND ART

Polysaccharides have been used as a food raw material from the old time and, in recent years, have begun to be paid attention as a macromolecular material which is environment friendly, as a safe material having biocompatibility and, further, as a functional material. The polysaccharides can be classified into neutral polysaccharides typified by a starch, cellulose, dextrin and the like; acidic polysaccharides typified by alginic acid, hyaluronic acid and the like; and basic polysaccharides typified by chitosan. It has been found that the presence or the absence of an acidic sugar and a basic sugar, and an abundance ratio between them greatly influence on physical properties and function of polysaccharides. Among them, particularly, the acidic polysaccharides have been widely utilized in foods, cosmetics, medicaments and the like, and an acidic polysaccharide having a new structure or function has been expected.

The method which has been previously used for finding a new acidic polysaccharide is a method of finding a novel acidic polysaccharide from nature, or a method of binding a carboxyl group or a sulfuric acid group to an existing polysaccharide by a chemical procedure. However, a uronic acid-containing glucan in which a uronic acid residue is bound to a non-reducing end has not been found in nature and, even if a chemical method is used, synthesis of a uronic acid-containing glucan in which a uronic acid residue is bound only to a non-reducing end is not easy, and, chemical synthesis of a uronic acid-containing glucan in which a uronic acid residue is bound only to a non-reducing end has not been suggested or disclosed.

A procedure of performing a reaction of oxidizing a polysaccharide in the presence of a catalyst of an N-oxyl compound to obtain water-soluble polyuronic acid is known. This oxidation method is to oxidize a polysaccharide while an oxoammonium salt is sequentially produced in a system using an N-oxyl compound such as 2,2,6,6-tetramethyl-1-piperidinyloxy radical (TEMPO) and a co-oxidizing agent such as sodium hypochlorite in a water dispersion or solution system of a polysaccharide (Patent Documents 1 to 3). The aforementioned method is applied to hardly-soluble polysaccharides such as cellulose, in addition to water-soluble polysaccharides such as a starch and pullulan. However, in this method, since a glucose residue in the interior of a polysaccharide is randomly oxidized, a polysaccharide containing a glucuronic acid residue only on a non-reducing end cannot be obtained.

As a substance having a glucuronic acid residue on a non-reducing end, various glycosides present in nature such as glycyrrhizin and baicalin, glycosides generated by glucuronic acid conjugation which is performed as detoxification action in a body of an animal, and the like are known. However, these are a so-called glycoside in which glucuronic acid is bound to an aglycon, and do not contain an α(alpha)-1,4-glucan.

α-Glucan phosphorylase (EC2.4.1.1) is an enzyme which acts on glucose-1-phosphate (Glc-1-P) and catalyzes a reaction of transferring a glucose residue to a non-reducing end of a receptor glucan (and a reverse reaction thereof). This reaction is shown in the following formula; wherein, Glucan primer is a receptor glucan, and Glucan Phosphorylase is α-glucan phosphorylase. A glucan obtained by transfer of a glucose residue of one molecule can act again as a receptor, and a transfer reaction is repeated. As a result, the finally obtained glucan can be a high molecular weight glucan.

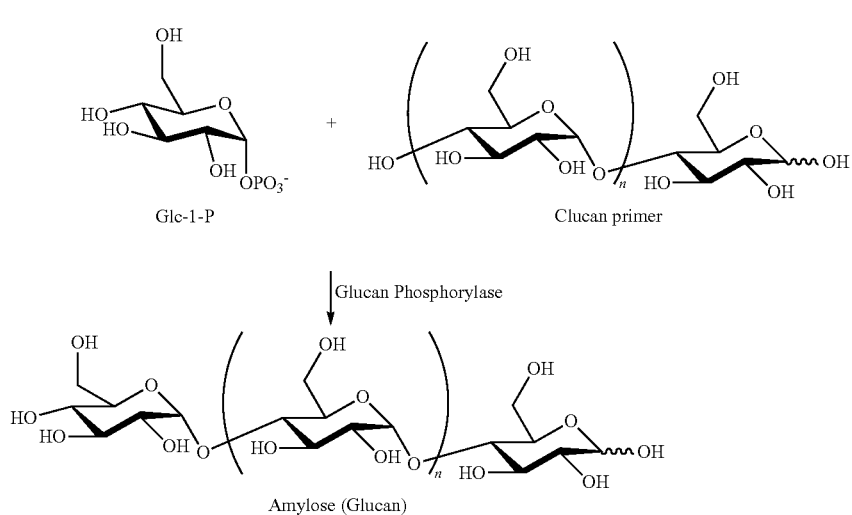

[Chemical formula 1]

α-Glucan phosphorylase is one of ubiquitous enzymes which are distributed in almost all organisms, and extremely many kinds of α-glucan phosphorylases are known. α-Glucan phosphorylase, a reaction mechanism of which is best studied, is potato-derived α-glucan phosphorylase.

In recent years, it has been reported that potato-derived α-glucan phosphorylase can use an analog of glucose-1-phosphate (described as G-1-P or Glc-1-P) as a substrate. Non-Patent Document 1 discloses that potato-derived α-glucan phosphorylase can transfer a xylose residue to a non-reducing end of a maltooligosaccharide utilizing xylose-1-phosphate (Xyl-1-P) as a substrate. Non-Patent Document 2 discloses that potato-derived α-glucan phosphorylase can transfer a glucosamine residue to a non-reducing end of a maltooligosaccharide utilizing glucosamine-1-phosphate (GlcN-1-P) as a substrate. G-1-P and a G-1-P analog are shown in the following chemical formula:

[Chemical formula 2]

G-1-P and G-1-P analogs

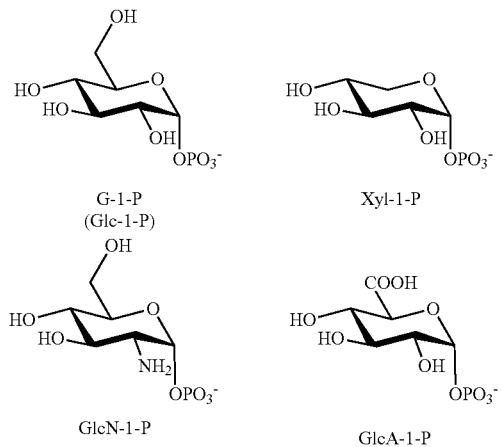

On the other hand, Non-Patent Document 3 discloses that glucuronic acid-1-phosphate (GlcA-1-P) being a substance in which a 6-position of glucose-1-phosphate is oxidized can be synthesized by chemical oxidation of glucose-1-phosphate using a TEMPO catalyst. The present inventors tried a few kinds of α-glucan phosphorylases including potato α-glucan phosphorylase, intending that α-glucan phosphorylase is allowed to act on glucuronic acid-1-phosphate to thereby transfer a glucuronic acid residue to a non-reducing end of a receptor glucan, but could not produce an intended glucuronic acid-containing glucan.

A medically effective ingredient of medicaments is rapidly changing from a chemically synthesized stable low-molecular weight compound to an unstable substance which is easily degraded in blood, such as a protein, an antibody and a nucleic acid. For this reason, there is a necessity of stabilizing these unstable medically effective ingredients to keep the blood concentration of the medically effective ingredient high. In addition, in order to decrease side effects of drugs, a necessity of delivering drugs to a target tissue efficiently has been increasing. Under such a background, a so-called drug delivery system (DDS) technique (i.e., a technique of delivering a medically effective ingredient to a desirable target at a desirable concentration for a desirable time) has been utilized in earnest (Non-Patent Documents 4 to 7).

In the DDS technique of medicaments, a modifying material for a medically effective ingredient is important. The term "modifying material" in the present specification refers to a material which modifies a medically effective ingredient by covalently binding, or via non-covalent type interaction, with a medically effective ingredient. By utilizing the modifying material, a variety of properties (for example, pharmacokinetics (for example, absorption, distribution, metabolism and excretion), pharmacological effect, stability and the like) of the medically effective ingredient can be modified. As a substance which has been used previously as the modifying material of the medically effective ingredient, there are a variety of substances, and what is used most generally is a macromolecular material. For example, polyethylene glycol (PEG) which is a synthetic macromolecule, and derivatives thereof are widely utilized as a modifying material for medicaments. Many medicament-modifying materials having a functional group for binding the medically effective ingredient on a terminus of a PEG chain have been developed, and such modifying materials are actually utilized as a medicament. Specific application examples include pegylated interferon α (product name: PEGASYS). Since interferon α has a small molecular weight and is easily excreted into urine, there was a problem that it has a short half-life in blood. However, the half-life in blood was successfully enhanced dramatically by covalently binding interferon α to a PEG chain having a molecular weight of 40,000 to form an interferon α-conjugate having a high molecular weight.

The modifying material of the medically effective ingredient can be utilized not only for directly modifying the medically effective ingredient but also for modifying a finely particulate carrier for other DDSs such as a liposome. An unmodified liposome is captured by phagocyte cells of a reticuloendothelial tissue (RES) during circulation in blood, and the blood concentration of the liposome is rapidly reduced. However, a pegylated liposome in which a PEG chain is bound to a surface of a liposome (also referred to as a Stealth Liposome) is difficult to be taken into the RES, and has a property that it is circulated and stays in blood for a long time. A Stealth Liposome preparation in which doxorubicin being an anti-cancer agent is encapsulated is sold with a trade name of DOXIL (registered trademark) (CAELYX (registered trademark) in Europe). DOXIL (registered trademark) is a liposome having a particle size of 70 to 100 nm, is supplied in the state of a dispersed aqueous solution, and is intravenously administered. There are the results that the disappearance half-life when DOXIL (registered trademark) is administered to a Kaposi's sarcoma AIDS patient is long and about 45 hours, and the concentration in Kaposi's sarcoma after 72 hours from administration is about 5-fold higher as compared with the case of doxorubicin alone.

As described above, the remarkable effect is recognized in the modification of the medically effective ingredient or the finely particulate carrier for DDSs, with a macromolecular material. However, on the other hand, a problem has been pointed out. For example, when a high-molecular weight synthetic macromolecule which has no degradability in a living body and will not undergone renal glomerular filtration is administered to blood, there are a risk that the macromolecule is accumulated in a particular organ and a risk that side effects due to the accumulation are generated. The reason is that a molecule having a molecular weight of a few tens thousands or less present in blood undergoes renal glomerular filtration and is rapidly excreted into urine, but a molecule having a molecular weight of a few tens thousands or more does not undergo renal glomerular filtration and its excretion into urine is limited. For this reason, a modifying material of the medically effective ingredient which can be safely utilized is expected.

PRIOR ART DOCUMENTS

Patent Documents

[Patent Document 1] Japanese Laid-Open Publication No. 2006-124598
[Patent Document 2] Japanese Laid-Open Publication No. 2005-15680
[Patent Document 3] Japanese Laid-Open Publication No. 10-251302

Non-Patent Documents

[Non-Patent Document 1] Nawaji et al., J. Carbohydr. Chem. 2008, 27, 214-222
[Non-Patent Document 2]-Nawaji et al., Carbohydr. Res. 2008, 343, 2692-2696
[Non-Patent Document 3] Heeres et al., Carbohydr. Res. 1997, 299, 221-227
[Non-Patent Document 4] Hiroaki Okada, "Drug delivery using functional DDS carriers" Chapter 1, General Statement: Kinousei DDS carrier wo mochiita seizai sekkei ni yoru soyaku (Drug Discovery by Preparation Design Using Functional DDS Carrier), CMC Publishing Co., Ltd., 2008, 1-23
[Non-Patent Document 5] Masayuki Yokoyama, "Polymeric materials for drug carriers, Special Topic, DDS ni riyou sareru kobunshi kagaku (Polymer Chemistry Utilized in DDS)", Drug Delivery System 23-6, 2008: 610-617
[Non-Patent Document 6] Maria Laura Immordino et al., International Journal of Nanomedicine 2006: 1(3) 297-315
[Non-Patent Document 7] J. Milton Harris and Robert B. Chess, NATURE REVIEWS, DRUG DISCOVERY, VOLUME 2, MARCH 2003, 214-221

SUMMARY OF THE INVENTION

Problems to be Solved by the Invention

The present invention is intended to solve the above-mentioned problems.

An ideal modifying material for the medically effective ingredient which can be safely utilized is thought to have the following characteristics.

(1) The modifying material shall be a macromolecular material provided with a functional group which can bind to or interact with the medically effective ingredient;

(2) The modifying material shall be a macromolecular material which can be degraded in a living body, and after administration, shall be degraded into components which are usually present in a body, or shall be completely excreted to the outside of a body and shall not be accumulated in a body;

(3) The modifying material shall have such a stable quality that it can be usable as a medicament. That is, the structure can be specified, and a modifying material having the same quality shall be able to produce every time.

The present inventors thought that a macromolecular substance most excellent as the modifying material for the medically effective ingredient is a glucan (in the present specification, the glucan refers to an α-1,4-glucan, and an α-1,4-glucan which is branched with an α-1,6-bond(s)). Since glycogen or a starch, which is accumulated in an animal's and plant's body as a polysaccharide for storage, is one kind of glucan, it is a component which is always present in a body of a human, and is excellent in biocompatibility. Further, the glucan undergoes hydrolysis by α-amylase in a body, and is converted into glucose or a maltooligosaccharide being a component which is always present in a body. For this reason, the glucan can be said to be the safest macromolecular material.

The glucan has another advantage that design of its structure is easy. It is also easy to artificially alter the structure of the glucan. Methods for controlling the molecular weight, degree of branching, cyclization and the like of the glucan are known. Completely linear glucans in which glucose residues are bound only with an α-1,4-bond, glucans which are branched at high frequency by some glucose residues bound with an α-1,6-bond, and the like are available. In a branched glucan, every time an α-1,6-bond is increased by one, one new non-reducing end is generated. For this reason, a branched glucan molecule which is branched at high frequency has quite many non-reducing ends. The number of α-1,6-bonds can be suitably adjusted according to desire upon synthesis of a glucan molecule. The fact that the glucan has a customizable structure as described above is also thought to be advantageous upon the use as the modifying material for the medically effective ingredient.

On the other hand, the greatest problem when the glucan is utilized as the modifying material for the medically effective ingredient is that it does not have a functional group which can bind to or interact with the medically effective ingredient. It is possible to introduce a cationic or anionic functional group into a large number of hydroxyl groups present in a glucan by a chemical reaction. However, when such a procedure is used, the position of introduction of the functional group is random and it is difficult to obtain a modifying material of the same quality. Therefore, this procedure is not preferable for utilization in medicaments. Further, there are problems that the glucan in which a substituent has been chemically introduced is suppressed in degradation with amylase, and that glucose which has undergone substitution, which is generated by degradation, is not a component usually present in a body, and that anxiety for safety is generated and the like.

The present inventors thought that introduction of glucuronic acid into a non-reducing end of a glucan chain is the most ideal method of modifying a glucan. This is because glucuronic acid is a monosaccharide having a carboxyl group and is a component which is usually present in a body, and there is no anxiety for safety. A carboxyl group of glucuronic acid can be utilized for binding or interaction with the medically effective ingredient. If glucuronic acid can be selectively introduced into a non-reducing end of a glucan, since the introduction position is not random, the same quality material can be produced reproductively, and this is suitable for utilization in medicaments. When one wants to increase an amount of introduction of a glucuronic acid residue into a glucan, it is possible to adjust the introduction amount for example by using a glucan having a high branching frequency. Further, since the introduction position is at an end, it is thought to be no influence on degradability of a glucan with α-amylase. In the case of a branched glucan which is highly branched, since non-reducing ends are distributed in an outermost layer of a glucan molecule, introduced glucuronic acid residues are distributed in an outermost layer of a glucan molecule after introduction of a glucuronic acid residue, and it is thought that this is ideal for interaction or binding with the medically effective ingredient. As described above, a glucan in which a glucuronic acid residue is selectively bound to a non-reducing end has a possibility that it can be an excellent modifying material for the medically effective ingredient. However, a method for producing a glucan in which a glucuronic acid residue is bound to a non-reducing end has not been known, and the function thereof has not been confirmed. For this reason, the present inventors were searching a technique of selectively introducing a functional group into a non-reducing end of a glucan.

Means for Solving the Problems

The present inventors intensively studied in order to solve the aforementioned problems and found that *Aquifex aeolicus* VF5-derived α-glucan phosphorylase acts on glucuronic acid-1-phosphate which is not its original substrate, and can catalyze a reaction of transferring only one molecule of a glucuronic acid residue to a non-reducing end of a linear glucan, and completed the present invention based on this finding (for example, see FIG. 1). Further, the present inventors found that *Aquifex aeolicus* VF5-derived α-glucan phosphorylase acts on glucuronic acid-1-phosphate, and can catalyze a reaction of transferring a glucuronic acid residue to one or more non-reducing ends of a branched glucan, and completed the present invention based on this finding (for example, see FIG. 2).

An object of the present invention is to develop a novel uronic acid-containing glucan, a modified product thereof, and a conjugate thereof. In the uronic acid-containing glucan, a modified product thereof and a conjugate thereof of the present invention, a uronic acid residue is bound only to a non-reducing end. In the glucuronic acid-containing glucan, a modified product thereof and a conjugate thereof of the present invention, a glucuronic acid residue is bound only to a non-reducing end. In the present invention, transfer of a glucuronic acid residue is performed using α-glucan phosphorylase (EC 2.4.1.1). For this reason, binding of a glucuronic acid residue to a glucan is an α-bond. As an enzyme which can transfer glucuronic acid to an aglycon, glucuronosyl transferase (Glucuronosyl transferase, UDP-glucuronate β-D-glucuronosyltransferase) classified into EC 2.4.1.17 has been previously well known, however glucuronosyl transferase is an enzyme which transfers a glucuronic acid residue to an aglycon with a β-bond. For this reason, the product has a different steric configuration from those obtained by binding a glucuronic acid residue to an aglycon using α-glucan phosphorylase used in the method of the present invention. Further, glucuronosyl transferase cannot use a glucan such as a maltooligosaccharide as a receptor. For this reason, even when glucuronosyl transferase is used, a glucan to which a glucuronic acid residue is bound cannot be obtained. Therefore, a glucuronic acid-containing glucan was generated first by using α-glucan phosphorylase. Since the present uronic acid-containing glucan, a modified product thereof and a conjugate thereof have uronic acid on a terminus, a glucan terminus comes to be negatively charged, and a physicochemical nature of the glucan is changed. The present uronic acid-containing glucan, a modified product thereof and a conjugate thereof are expected to be widely utilized in foods, cosmetics, medicaments and the like.

For example, the present invention provides the followings:

(Item 1) A glucuronic acid-containing glucan in which a glucuronic acid residue is bound to at least one non-reducing end of a glucan, but there is no glucuronic acid residue at the positions other than the non-reducing end, wherein the glucan is a branched α-1,4 glucan or a linear α-1,4 glucan.

(Item 2) The glucuronic acid-containing glucan according to Item 1, wherein the glucan is a branched α-1,4 glucan, and a glucuronic acid residue is bound to at least one non-reducing end of a plurality of non-reducing ends of the branched α-1,4-glucan.

(Item 3) The glucuronic acid-containing glucan according to Item 2, wherein the branched α-1,4 glucan is selected from the group consisting of a branched maltooligosaccharide, a starch, amylopectin, glycogen, dextrin, an enzymatically synthesized branched glucan and highly branched cyclic dextrin.

(Item 4) A hydroxyl group-modified product of the glucuronic acid-containing glucan according to any one of Items 1-3, wherein the modification is a modification on some or all of alcoholic hydroxyl groups of the glucan, and the modification is independently selected from the group consisting of hydroxyalkylation, alkylation, acetylation, carboxymethylation, sulfation and phosphorylation.

(Item 5) A reducing end-modified product of the glucuronic acid-containing glucan according to any one of Items 1-3 or a hydroxyl group-modified product thereof.

(Item 6) A carboxyl group-modified product of the glucuronic acid-containing glucan according to any one of Items 1-3, a hydroxyl group-modified product thereof or a reducing end-modified product thereof, wherein the modification is a modification on some or all of carboxyl groups of the glucuronic acid residues, the modification is attained by a reaction of the carboxyl group and a carboxyl group modifying reagent, and the carboxyl group modifying reagent has at least one amine group and at least one other functional group.

(Item 7) The carboxyl group-modified product according to Item 6, wherein the functional group is a cationic functional group or an anionic functional group.

(Item 8) The carboxyl group-modified product according to Item 6, wherein the functional group is a hydrophobic functional group.

(Item 9) The carboxyl group-modified product according to Item 6, wherein the functional group is selected from the group consisting of a maleimide group, a thiol group and an aldehyde group.

(Item 10) The carboxyl group-modified product according to Item 6, wherein the carboxyl group modifying reagent is selected from the group consisting of N-hydroxysuccinimide, N,N-disuccinimide carbonate, 1-hydroxybenzotriazole, N-hydroxy-5-norbornene-2,3-dicarboxyimide, N-hydroxyphthalimide, isobutyl chloroformate and 4-hydroxyphenyldimethylsulfonium methylsulfate.

(Item 11) A method for producing a glucuronic acid-containing glucan, characterized by allowing α-glucan phosphorylase to act on an aqueous solution comprising a glucan and glucuronic acid-1-phosphate.

(Item 12) The method according to Item 11, wherein the α-glucan phosphorylase has 95% or more sequence identity with an amino acid sequence of α-glucan phosphorylase derived from *Aquifex aeolicus* VF5, and has activity of transferring glucuronic acid to a non-reducing end of a glucan.

(Item 13) A medicament comprising the glucuronic acid-containing glucan according to any one of Items 1-3, a hydroxyl group-modified product thereof, a reducing end-modified product thereof, or a carboxylic acid group-modified product thereof, and a medically effective ingredient.

(Item 14) The medicament according to Item 13, wherein the medically effective ingredient is selected from the group consisting of a low-molecular weight organic compound, a protein, a peptide, an antibody, an antibody fragment, a receptor, a receptor fragment, a DNA, an RNA, a siRNA and an RNA aptamer.

(Item 15) A conjugate of a medically effective ingredient and the glucuronic acid-containing glucan according to any one of Items 1-3, a hydroxyl group-modified product thereof, a reducing end-modified product thereof, or a carboxylic acid group-modified product thereof, wherein the medically effective ingredient is covalently bound to at least one of carboxyl groups of the glucuronic acid residue directly or bound to at least one of carboxyl groups of the glucuronic acid residue via a spacer.

(Item 16) A composition for clinical diagnosis, comprising the glucuronic acid-containing glucan according to any one of Items 1-3, a hydroxyl group-modified product thereof, a reducing end-modified product thereof, or a carboxylic acid group-modified product thereof.

(Item 17) A finely particulate carrier for a DDS, comprising the glucuronic acid-containing glucan according to any one of Items 1-3, a hydroxyl group-modified product thereof, a reducing end-modified product thereof, or a carboxylic acid group-modified product thereof.

(Item 18) The carrier according to Item 17, wherein the finely particulate carrier for a DDS is selected from the group consisting of a liposome, a virus particle, a macromolecule micelle and a nanogel composed of macromolecule bearing hydrophobic groups.

(Item 19) A contrast agent for clinical diagnosis, comprising the glucuronic acid-containing glucan according to any one of Items 1-3, a hydroxyl group-modified product thereof, a reducing end-modified product thereof, or a carboxylic acid group-modified product thereof.

(Item 20) A glucuronic acid-containing glucan having the structure consisting of formula 5:

[Chemical formula 3]

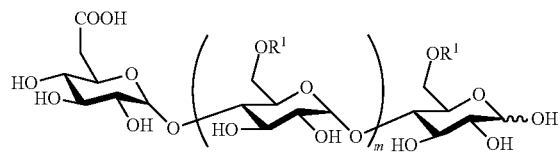

Formula 5 wherein m is an integer of 1 or more, and $R^1$ is independently H, a glucan chain having the structure of formula A or a glucan chain having the structure of formula B:

[Chemical formula 4]

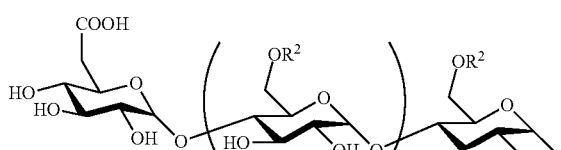

Formula A in formula A, k is an integer of 1 or more, and $R^2$ is independently H, a glucan chain having the structure of formula A or a glucan chain having the structure of formula B:

[Chemical formula 5]

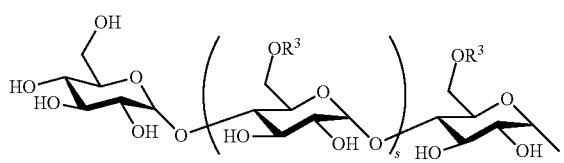

Formula B in formula B, s is an integer of 1 or more, and $R^3$ is independently H, a glucan chain having the structure of formula A or a glucan chain having a structure of formula B.

(Item 21) A glucuronic acid-containing glucan or a hydroxyl group-modified product of the glucuronic acid-containing glucan, having the structure consisting of formula 6:

[Chemical formula 6]

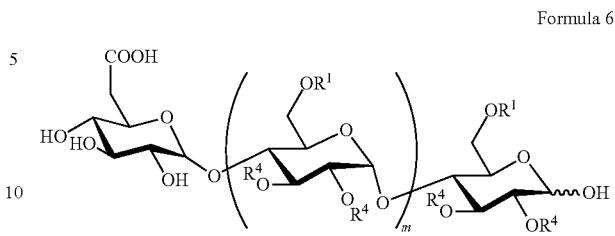

Formula 6 wherein m is an integer of 1 or more, and $R^1$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B:

[Chemical formula 7]

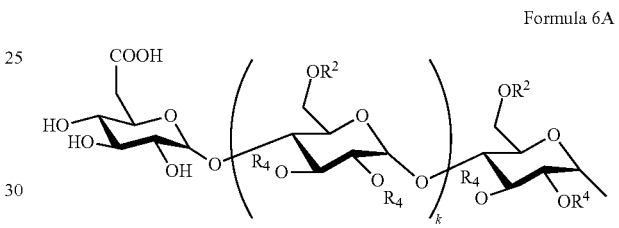

Formula 6A in formula 6A, k is an integer of 1 or more, and $R^2$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B:

[Chemical formula 8]

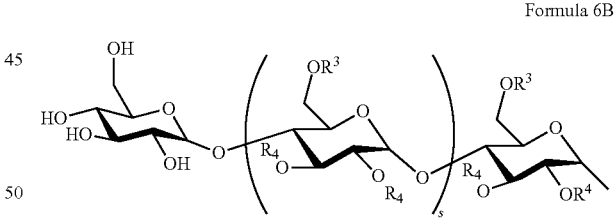

Formula 6B in formula 6B, s is an integer of 1 or more, and $R^3$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B, and in formula 6, formula 6A and formula 6B, $R^4$ is independently selected from the group consisting of H, a hydroxyalkyl group, an alkyl group, an acetyl group, a carboxymethyl group, a sulfuric acid group and a phosphoric acid group.

(Item 22) A glucuronic acid-containing glucan, a hydroxyl group-modified product of the glucuronic acid-containing glucan or a reducing end-modified product thereof, having the structure consisting of formula 7:

[Chemical formula 9]

Formula 7

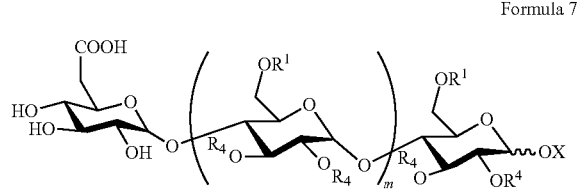

wherein m is an integer of 1 or more, and $R^1$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B:

[Chemical formula 10]

Formula 6A

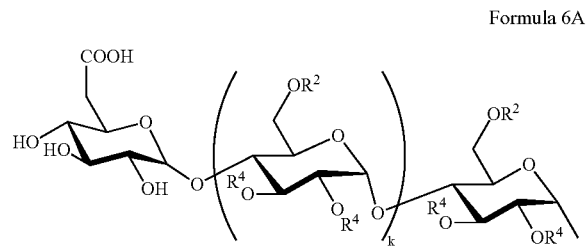

in formula 6A, k is an integer of 1 or more, and $R^2$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B:

[Chemical formula 11]

Formula 6B

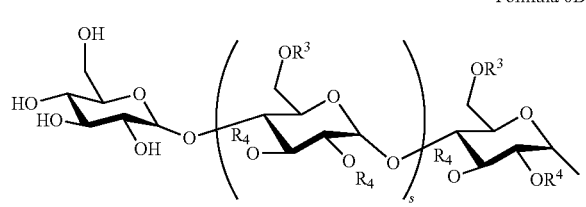

in formula 6B, s is an integer of 1 or more, and $R^3$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B, in formula 7, formula 6A and formula 6B, $R^4$ is independently selected from the group consisting of H, a hydroxyalkyl group, an alkyl group, an acetyl group, a carboxymethyl group, a sulfuric acid group and a phosphoric acid group, and in formula 7, X is independently selected from the group consisting of a monosaccharide, a non-reducing carbohydrate, a biocompatible macromolecule, a liposome constituent component, a glycoside and an amine group-containing low-molecular weight substance.

(Item 23) The glucuronic acid-containing glucan, the hydroxyl group-modified product of the glucuronic acid-containing glucan or the reducing end-modified product thereof according to Item 22, wherein X is selected from the group consisting of glucosamine, N-acetylglucosamine, gluconic acid, sorbitol, sucrose, trehalose, cyclodextrin, cyclic dextrin, cyclic amylose, starches, cellulose, chitin, chitosan, dextran, proteins, peptides, phospholipids, fatty acids, surfactants, ascorbic acid glucosides, hydroquinone glucosides, hesperidin glucosides, rutin glucosides, para-nitrophenyl maltopentaose, dodecylmaltose, flavonoid glycosides, terpene glycosides, phenol glycosides, chalcone glycosides, steroid glycosides, amino acids and dodecylamine.

(Item 24) A glucuronic acid-containing glucan, a hydroxyl group-modified product of the glucuronic acid-containing glucan, a reducing end-modified product thereof, or a carboxyl group-modified product thereof, having the structure consisting of formula 8:

[Chemical formula 12]

Formula 8

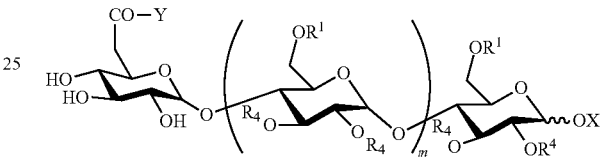

wherein m is an integer of 1 or more, and $R^1$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B:

[Chemical formula 13]

Formula 6A

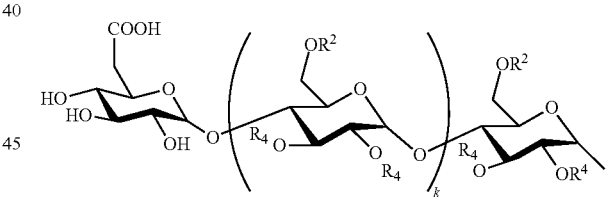

in formula 6A, k is an integer of 1 or more, and $R^2$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B:

[Chemical formula 14]

Formula 8A

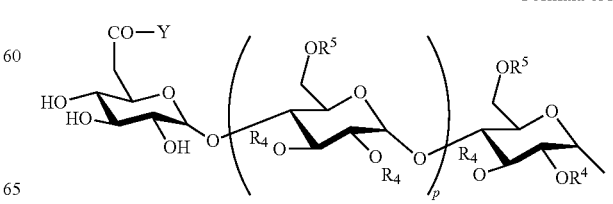

in formula 8A, p is an integer of 1 or more, and $R^5$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B:

[Chemical formula 15]

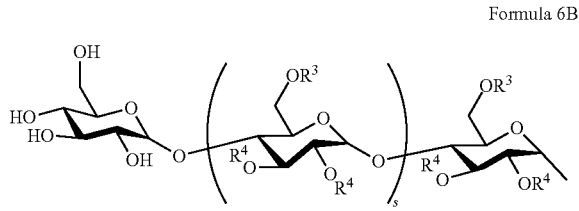

Formula 6B in formula 6B, s is an integer of 1 or more, and $R^3$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B, in formula 8, formula 6A, formula 8A, and formula 6B, $R^4$ is independently selected from the group consisting of H, a hydroxyalkyl group, an alkyl group, an acetyl group, a carboxymethyl group, a sulfuric acid group, and a phosphoric acid group, in formula 8, X is independently selected from the group consisting of a monosaccharide, a non-reducing carbohydrate, a biocompatible macromolecule, a liposome constituent component, a glycoside and an amine group-containing low-molecular-weight substance, and in formula 8 and formula 8A, Y is a substituent introduced for binding with a medically effective ingredient, Y is obtained by a reaction with a carboxyl group modifying reagent, and the carboxyl group modifying reagent has at least one amine group and at least one other functional group.
(Item 25) The glucuronic acid-containing glucan, the hydroxyl group-modified product of the glucuronic acid-containing glucan, the reducing end-modified product thereof, or the carboxyl group-modified product thereof according to Item 24, wherein the functional group is a cationic functional group or an anionic functional group.
(Item 26) The glucuronic acid-containing glucan, the hydroxyl group-modified product of the glucuronic acid-containing glucan, the reducing end-modified product thereof, or the carboxyl group-modified product according to Item 24, wherein the functional group is a hydrophobic functional group.
(Item 27) The glucuronic acid-containing glucan, the hydroxyl group-modified product of the glucuronic acid-containing glucan, the reducing end-modified product thereof, or the carboxyl group-modified product thereof according to Item 24, wherein the functional group is selected from the group consisting of a maleimide group, a thiol group and an aldehyde group.
(Item 28) The glucuronic acid-containing glucan, the hydroxyl group-modified product of the glucuronic acid-containing glucan, the reducing end-modified product thereof, or the carboxyl group-modified product thereof according to Item 24, wherein the carboxyl group modifying reagent is selected from the group consisting of N-hydroxysuccinimide, N,N-disuccinimide carbonate, 1-hydroxybenzotriazole, N-hydroxy-5-norbornene-2,3-dicarboxyimide, N-hydroxyphthalimide, isobutyl chloroformate and 4-hydroxyphenyldimethylsulfonium methylsulfate.

For example, the present invention also provides the followings:
(Item 1) A uronic acid-containing glucan in which a uronic acid residue is bound to a non-reducing end of a glucan.
(Item 2) The uronic acid-containing glucan according to Item 1, wherein the glucan is a linear glucan.
(Item 3) The uronic acid-containing glucan according to Item 2, wherein the linear glucan is selected from the group consisting of a maltooligosaccharide, an amylose and an enzymatically synthesized amylose.
(Item 4) The uronic acid-containing glucan according to Item 1, wherein the glucan is a branched glucan, and a uronic acid residue(s) is bound to at least one non-reducing end of plural of non-reducing end of the branched glucan.
(Item 5) The uronic acid-containing glucan according to Item 4, wherein the branched glucan is selected from the group consisting of a branched maltooligosaccharide, a starch, amylopectin, glycogen, dextrin, an enzymatically synthesized branched glucan and a glucan in which an amylose(s) is grafted.
(Item 6) The uronic acid-containing glucan, wherein the carboxyl group(s) of a uronic acid residue(s) at the non-reducing end is further modified.
(Item 7) The uronic acid-containing glucan according to Items 1-6, wherein the uronic acid residue is glucuronic acid residue.
(Item 8) A method for producing a uronic acid-containing glucan, characterized by allowing α-glucan phosphorylase to act on an aqueous solution comprising a glucan and glucuronic acid-1-phosphate.
(Item 9) The method for producing a uronic acid-containing glucan according to Item 8, wherein the α-glucan phosphorylase is α-glucan phosphorylase derived from *Aquifex aeolicus* VF5.
(Item 10) The utilization of the uronic acid-containing glucan according to any one of Items 1-7 in the food application.
(Item 11) The utilization of the uronic acid-containing glucan according to any one of Items 1-7 in the cosmetic application.
(Item 12) The utilization of the uronic acid-containing glucan according to any one of Items 1-7 in the medicament application.
(Item 13) The utilization of the uronic acid-containing glucan according to any one of Items 1-7 in the chemical product application.

Effects of the Invention

In the uronic acid-containing glucan, a hydroxyl group-modified product thereof, a reducing end-modified product thereof, a carboxyl group-modified product thereof and a conjugate thereof of the present invention, a uronic acid residue is bound only to a non-reducing end of the glucan. Since the present uronic acid-containing glucan, a hydroxyl group-modified product thereof, a reducing end-modified product thereof, a carboxyl group-modified product thereof and a conjugate thereof have uronic acid on a terminus, a glucan terminus comes to be negatively charged, and a physicochemical nature of the glucan is changed. The present uronic acid-containing glucan, a hydroxyl group-modified product thereof, a reducing end-modified product thereof, a carboxyl group-modified product thereof and a conjugate thereof are expected to be widely utilized in foods, cosmetics, medicaments and the like.

Since the uronic acid-containing glucan, a hydroxyl group-modified product thereof, a reducing end-modified product thereof, and a carboxyl group-modified product thereof of the present invention are degraded in a living body and have a longer half-life in blood than that of an unmodified glucan, they are useful as a modifying material for a medically effective ingredient, a clinical diagnostic agent, a contrast agent and a finely particulate carrier for DDS. In the uronic acid-containing glucan, a hydroxyl group-modified product thereof, a reducing end-modified product thereof, and a carboxyl group-modified product thereof of the present invention, since their structure can be controlled by an enzymatic reaction, they are also excellent in quality stability.

In the uronic acid-containing glucan and a modified product thereof of the present invention, since a uronic acid residue is bound only to a non-reducing end of the glucan, a site which interacts with other molecules and a site which undergoes degradation with amylase could have been structurally separated. For this reason, even when utilized as a DDS carrier in a body, the glucan or the modified product thereof is degraded with an enzyme in a body, and therefore it does not cause the problem of residues due to staying in a body for an excessively long term.

BRIEF DESCRIPTION OF THE DRAWINGS

In FIG. 2, as an example of the branched glucan, Cluster Dextrin is shown. The structure of the part shown with an asterisk is shown in the square frame.

In FIG. 3, as an example of the branched glucan, Cluster Dextrin is shown.

maltose, G4: maltotetraose, G7: maltoheptaose, GlcA: glucuronic acid, G1P: glucose-1-phosphate, GlcA1P: glucuronic acid-1-phosphate). B shows the results of analysis of enzymatic reaction products obtained by acting *Aquifex aeolicus* VF5-derived α-glucan phosphorylase on G7 and GlcA-1-P. C is the results of analysis of the same enzymatic reaction products as those of B, after glucoamylase treatment. The peaks with an asterisk in C show the glucuronic acid-containing glucans of the present invention. Since the glucuronic acid-containing glucans of the present invention, is such that a glucuronic acid residue is bound to a non-reducing end, it exhibits resistance to glucoamylase. Among the peaks shown with an asterisk in FIG. 8C, the peak on the left end shows glucuronosyl maltotriose (GlcA-G3) that is a glucuronic acid residue bound to maltotriose. The peak which is second from left shows glucuronosyl maltotetraose (GlcA-G4). Third peak from left and righter peaks, in turn, as the position goes right, the degree of polymerization increases one by one, such as, GlcA-G5, GlcA-G6 and the like. D is the results of analysis of the same enzymatic reaction products as those of B, after treatment with glucoamylase and α-amylase. The glucuronic acid-containing glucans of the present invention (the peaks with an asterisk in FIG. 8C) were degraded with α-amylase, and new two peaks were generated on a low molecular weight side. Therefore, it can be understood that when *Aquifex aeolicus* VF5-derived α-glucan phosphorylase is used, glucans containing a glucuronic acid residue(s) are obtained.

Figure 9:
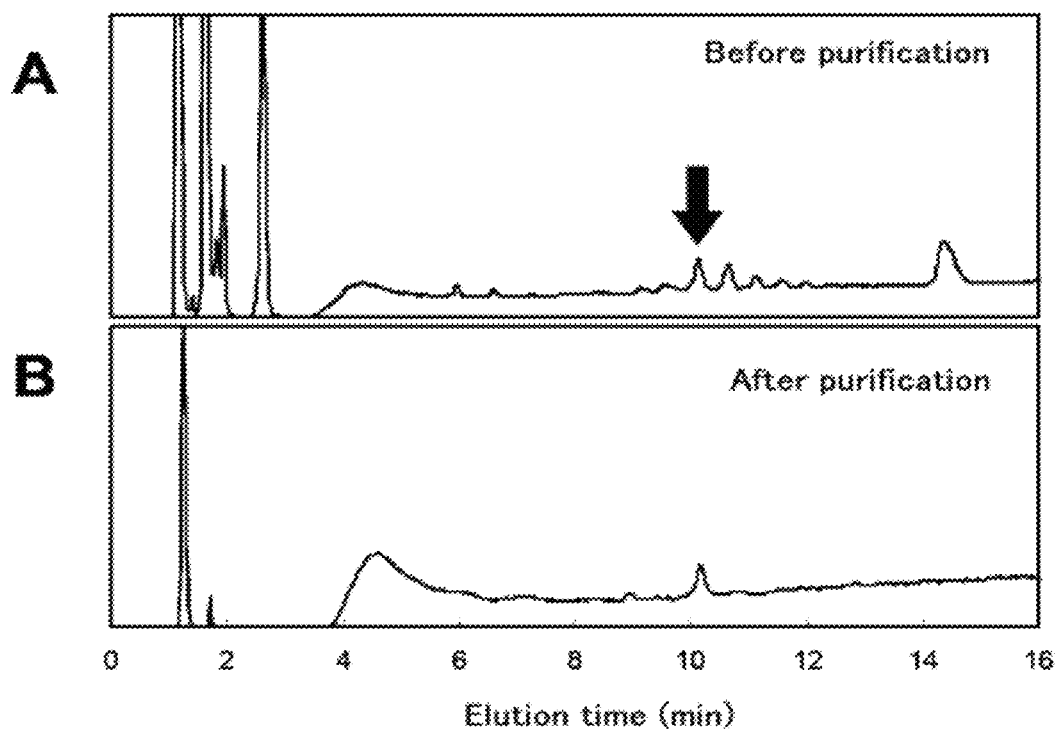
Figure 9:
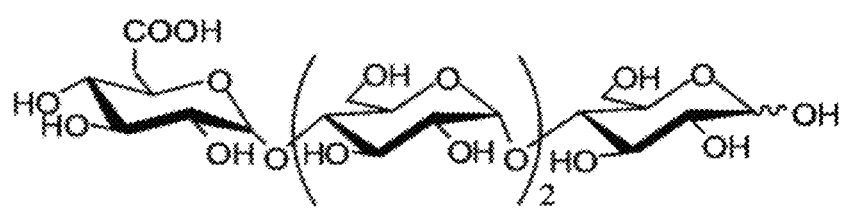

FIG. 9 is a figure showing fractionation of a product obtained by acting *Aquifex aeolicus* VF5-derived α-glucan phosphorylase on glucuronic acid-1-phosphate and maltotetraose. The peak shown with an arrow in FIG. 9A was fractionated and purified. The result of analysis of the fractionated and purified peak on an HPAEC-PAD apparatus is shown in FIG. 9B. By viewing FIG. 9B, it can be understood that only an objective peak was purified. It was found that, a sample after purification which was analyzed in FIG. 9B, further analyzed using TOF-MS, a glucan contained in a peak with the arrow is a conjugate of glucuronic acid and maltotriose (FIG. 9C).

Figure 10:
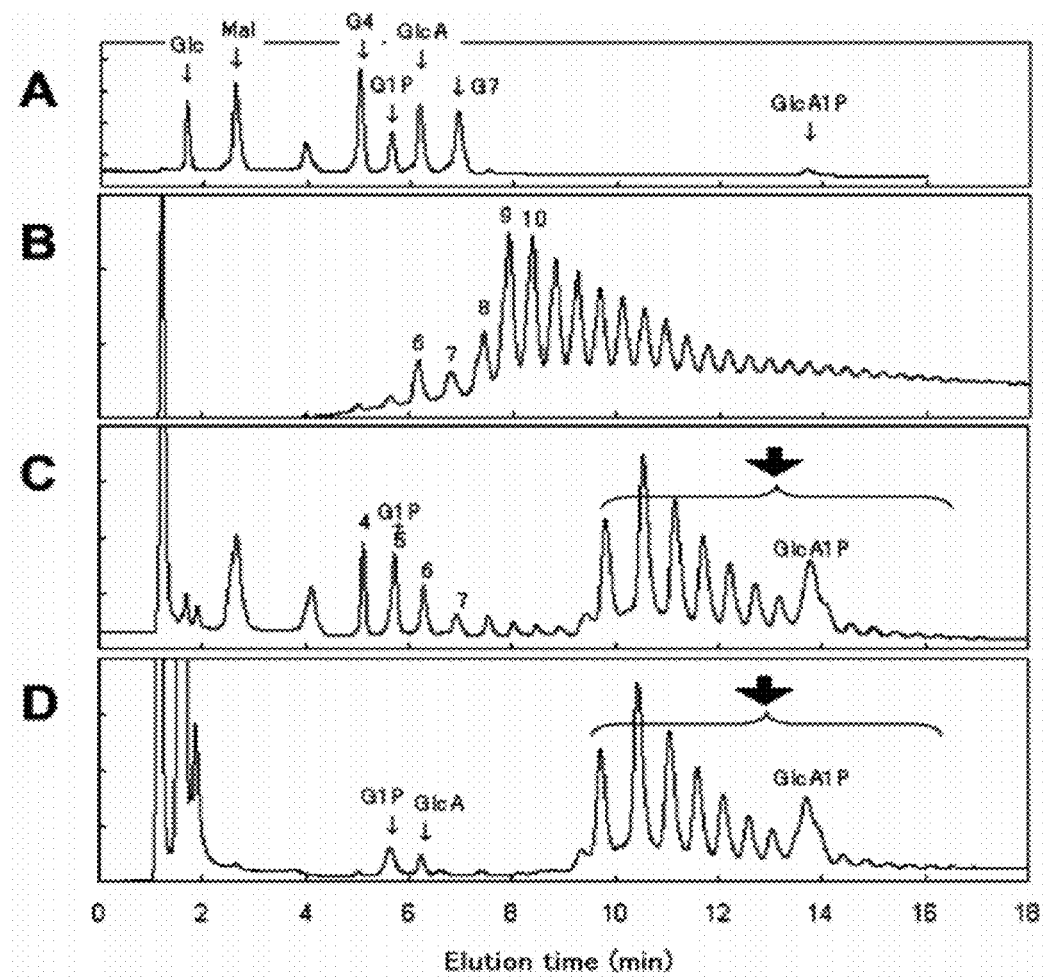

FIG. 10 is the results of analysis of the products obtained by acting *Aquifex aeolicus* VF5-derived α-glucan phosphorylase on glucuronic acid-1-phosphate and a branched glucan (Cluster Dextrin). A is a chromatogram of standard substances (Glc: glucose, Mal: maltose, G4: maltotetraose, G7: maltoheptaose, GlcA: glucuronic acid, G1P: glucose-1-phosphate, GlcA1P: glucuronic acid-1-phosphate). B shows the results of analysis of a branched glucan (Cluster Dextrin), after degradation with isoamylase. The numbers above each peak in FIGS. 10B and 10C indicate the degree of polymerization of a glucan shown by the peak. 4: maltotetraose; 5: maltopentaose; 6: maltohexaose; 7: maltoheptaose; 8: maltooctaose; 9: maltononaose; 10: maltodecaose. "G1P+5" in FIG. 10C indicates that the peak of G1P and the peak of maltopentaose are overlapped. C shows the results of analysis of enzymatic reaction products obtained by acting *Aquifex aeolicus* VF5-derived α-glucan phosphorylase on glucuronic acid-1-phosphate and a branched glucan (Cluster Dextrin), after degradation with isoamylase. D is the results of the same enzymatic reaction products as those of C, after treatment with isoamylase and glucoamylase. Peaks with the arrow in D indicate the glucuronic acid-containing glucans of the present invention. In the glucuronic acid-containing glucan of the present invention, since a glucuronic acid residue is bound to a non-reducing end, it exhibits resistance to glucoamylase. Among the peaks shown with an arrow in FIG. 10D, the peak on the left end indicates glucuronosyl maltotriose (GlcA-G3) that is a glucuronic acid residue bound to maltotriose. The peak which is second from left indicates glucuronosyl maltotetraose (GlcA-G4). Third peak from left and the peaks to its right, in turn, as the position goes right, the degree of polymerization increases one by one, such as, GlcA-G5, GlcA-G6 and the like. Therefore, it can be understood that, in FIG. 10D, glucans containing a glucuronic acid residue(s) (arrow) were obtained.

Figure 11:
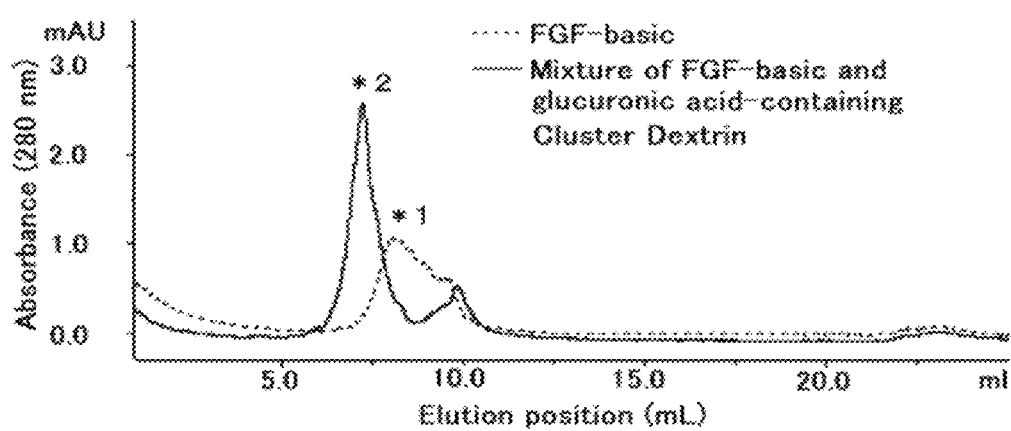

FIG. 11 is a figure showing that a glucuronic acid-containing glucan forms a complex with a protein. After 20 μg of FGF-basic and 0.5 mg of a glucuronic acid-containing glucan (BA-2) were mixed in 0.1 ml of a solution, this mixture was analyzed by FPLC analysis using a Superose 6 10/300 GL column (a column for size fractionation, manufactured by GE Company). Ion-exchanged water was used as an eluent and UV (280 nm) detection was performed. It can be understood that, as compared with the case where a glucuronic acid-containing glucan was not added to FGF-basic (peak with *1), in the case where the glucan was added (peak with *2), the elution time was early, and the molecular size was larger. Thus, it is indicated that the glucuronic acid-containing glucan can form a complex with a protein.

Figure 12:
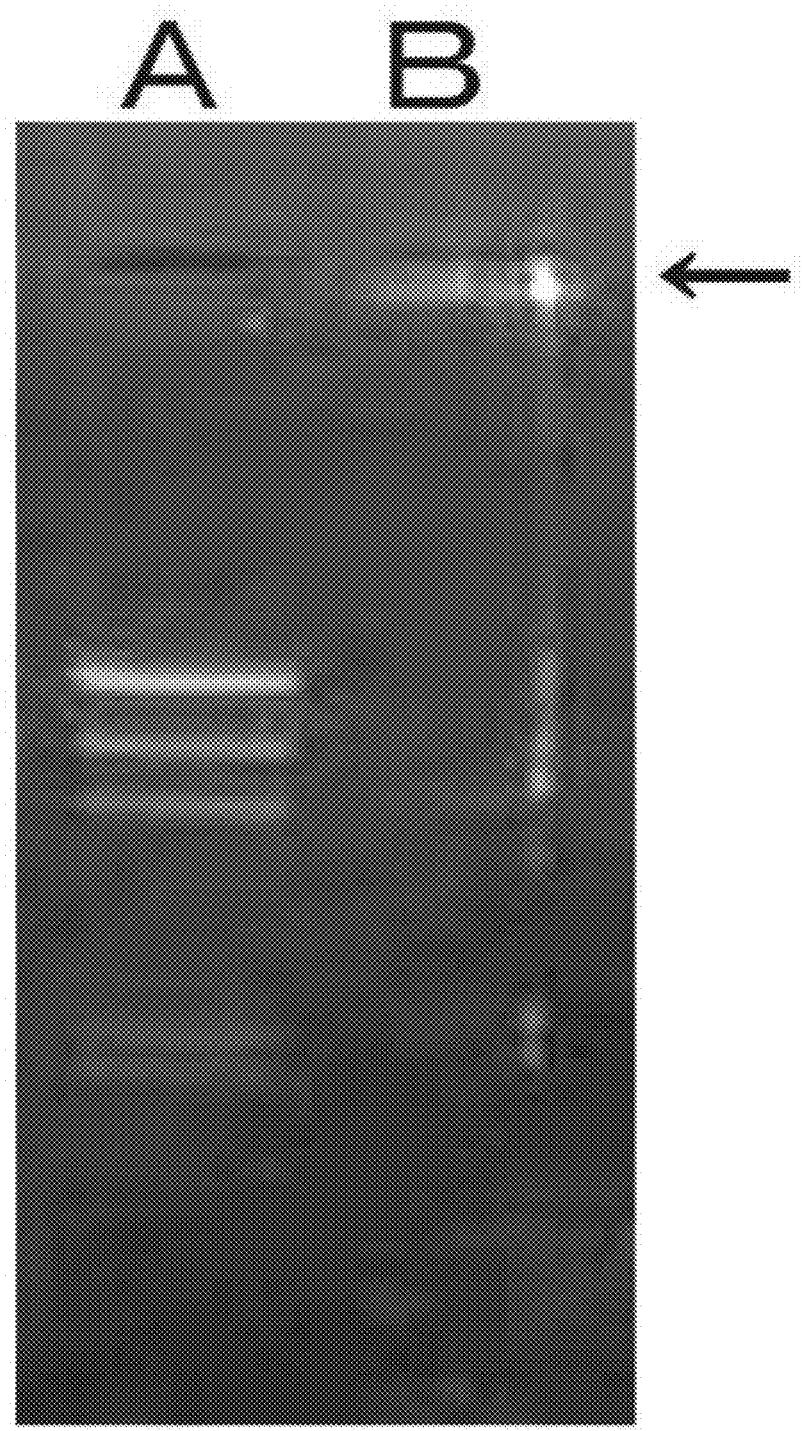

FIG. 12 is a figure showing formation of a complex of a cationized glucuronic acid-containing glucan and a DNA. After 0.2 μg of a cationized glucuronic acid-containing glucan and 0.5 μg of a lambda DNA-Hind III fragment were dissolved in 20 μl of ion-exchanged water, and this was allowed to stand at room temperature for 5 minutes, 1% agarose gel electrophoresis was performed. As compared with the case where the cationized glucuronic acid-containing glucan was not added (A), in the case where the glucan was added (B), mobility of a DNA fragment was remarkably slow. Therefore, it can be understood that the cationized glucuronic acid-containing glucan can form a complex with a DNA.

Figure 13:
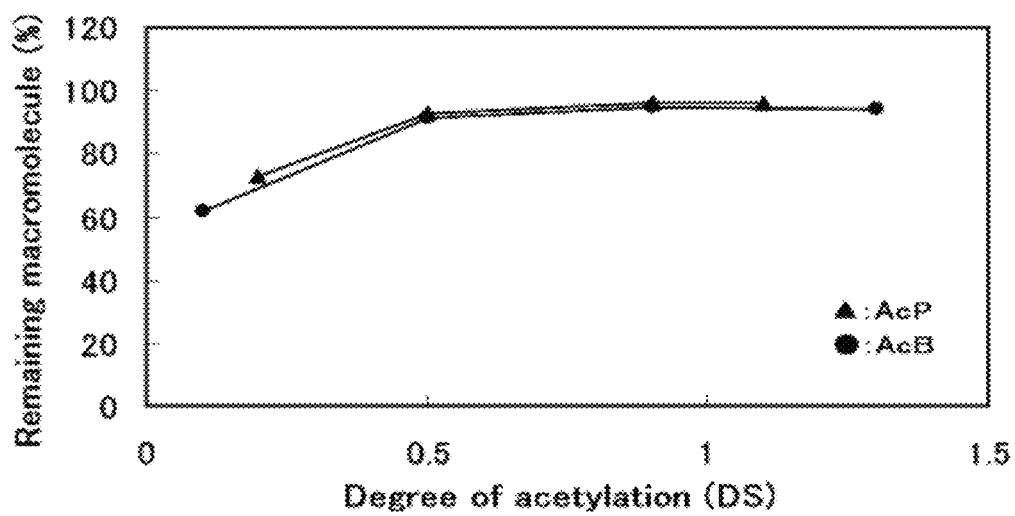

FIG. 13 shows the results of degradation of branched glucans having different degrees of acetylation (DS) (AcB1, AcB2, AcB3 or AcB4 and AcP1, AcP3, AcP4 or AcP5) with α-amylase. A black circle indicates AcB, and a black triangle indicates AcP.

Figure 14:
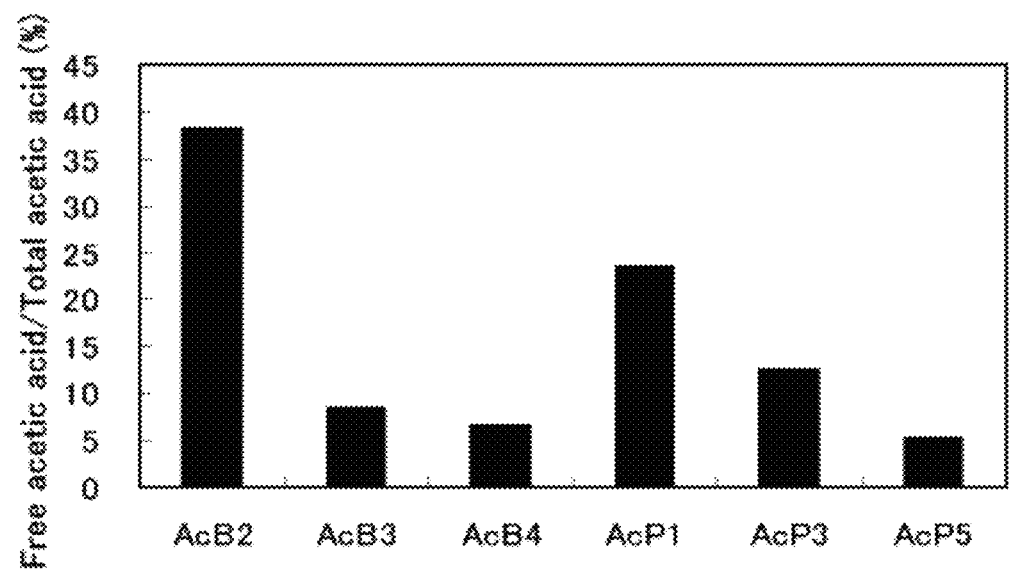

FIG. 14 shows the results after 6 hours from serum degradation of branched glucans having different degrees of acetylation (DS) (AcB2, AcB3 or AcB4 and AcP1, AcP3 or AcP5).

Figure 15:
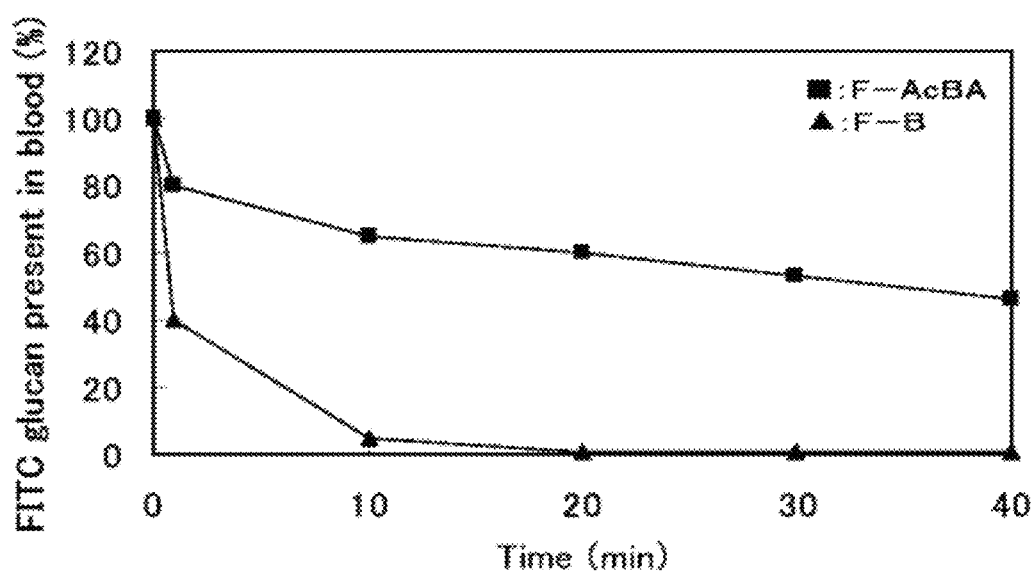

FIG. 15 shows a change with time in the amount of the glucan present in blood, of a glucuronic acid-containing acetylated glucan labeled with FITC (F-AcBA) and an unmodified glucan (F-B). A black triangle indicates F-B, and a black square indicates F-AcBA.

MODE FOR CARRYING THE INVENTION

The present invention will be explained in detail below.

Throughout the present specification, it should be understood that expression in a singular form includes a concept of a plural form thereof, unless otherwise indicated. In addition, it should be understood that a term used in the present specification is used in a sense which is usually used in the art, unless otherwise indicated.

(1. Materials)

(1.1) Glucans and Modified Products of Glucan

"Glucan", when used in the present specification, is a polysaccharide having D-glucose as a constituent unit. In the present invention, it is preferable to use, as the glucan, an α-D-glucan. In the present specification, unless otherwise indicated, the "glucan" refers to an "α-D-glucan". The α-D-glucan is a glucan in which two or more D-glucose units are connected mainly with an α-1,4-glucoside bond(s). Preferable glucans used in the present invention are a linear glucan and a branched glucan, more preferably a linear α-1,4-glucan and an α-1,4-glucan which is branched with an α-1,6-bond (also referred to as a branched α-1,4 glucan). It is preferable that the glucan used in the present invention does not contain an α-1,3-bond.

The linear α-D-1,4-glucan refers to a polysaccharide in which two or more saccharide units of D-glucose units are bound only with an α-1,4-glucoside(s). In the present specification, unless otherwise indicated, the linear α-D-1,4-glucan is referred to as a linear glucan or a linear α-1,4-glucan. Maltooligosaccharides and amylose are classified into a linear glucan and an α-1,4-glucan. The linear glucan has one non-reducing end.

Examples of the linear glucan suitably utilized in the present invention include maltooligosaccharides and amylose.

In the present specification, the term "maltooligosaccharide" refers to a substance which is produced by dehydration condensation of about 2 to about 10 D-glucoses, wherein D-glucose units are linked by α-1,4 bond(s). The degree of polymerization of a maltooligosaccharide is preferably about 3 or more, more preferably about 4 or more, and further preferably about 5 or more. The degree of polymerization of a maltooligosaccharide may be, for example, about 10 or less, about 9 or less, about 8 or less, about 7 or less, or the like. Examples of maltooligosaccharides include maltooligosaccharides such as maltose, maltotriose, maltotetraose, maltopentaose, maltohexaose, maltoheptaose, maltooctaose, maltononaose, and maltodecaose.

In the present specification, the term "amylose" refers to a linear molecule constructed of glucose units connected with α-1,4-linkages. An amylose is contained in natural starch. Amylose may be a natural amylose extracted from a natural starch, or may be an amylose synthesized by an enzymatic reaction (also referred to as "enzymatically synthesized amylose" in the present specification). Natural amylose may contain a branched part in some cases, but enzymatically synthesized amylose does not contain a branch. Further, natural amyloses have a large polydispersity and has a variation in the molecular weight, but an enzymatically synthesized amylose (particularly, an enzymatically synthesized amylose synthesized by the SP-GP method described in International Publication WO 02/097107 pamphlet) has a small polydispersity and has an extremely uniform molecular weight. For this reason, in the present invention, it is preferable to use an enzymatically synthesized amylose. The degree of polymerization of the amylose used in the present invention is preferably about 2 or more, more preferably about 3 or more, still more preferably about 10 or more, and most preferably about 30 or more. The degree of polymerization of the amylose used in the present invention is preferably about 2,000 or less, more preferably about 1,000 or less, still more preferably about 700 or less and most preferably about 500 or less.

In the present specification, the term "branched α-D-glucan" refers to a glucan in which a linear glucan, in which D-glucose units are connected with an α-1,4-glucoside bond(s), is branched with a bond other than an α-1,4-glucoside bond. In the present specification, unless otherwise indicated, the branched α-D-glucan refers to a branched glucan. A branching bond is either an α-1,6-glucoside bond, an α-1,3-glucoside bond, or an α-1,2-glucoside bond, and most preferably is an α-1,6-glucoside bond. It is preferable that a branched α-D-glucan used in the present invention does not contain an α-1,3-glucoside bond and an α-1,2-glucoside bond. The branched glucan usually has the same number of non-reducing ends as the number of branching bonds. When the branched glucan is treated with an enzyme which selectively breaks only an α-1,6-glucoside bond (for example, isoamylase, pullulanase, or the like), the branched glucan can be degraded into a mixture of linear α-1,4-glucans. These are referred to as a unit chain of the branched glucan, and the degree of polymerization thereof is referred to as a unit chain length.

Examples of the branched glucan suitably utilized in the present invention include branched maltooligosaccharides, starches, amylopectin, glycogen, dextrin, enzymatically synthesized branched glucan and highly branched cyclic dextrin.

In the present specification, the term "branched maltooligosaccharide" refers to a substance generated by dehydration condensation of about 3 to about 10 D-glucoses, in which D-glucose units are connected mainly with an α-1,4 bond(s), and which contains one or more branching bonds. The degree of polymerization of the branched maltooligosaccharide is preferably about 4 or more, more preferably about 5 or more, further preferably about 6 or more. The degree of polymerization of the branched maltooligosaccharide may be, for example, about 10 or less, about 9 or less, about 8 or less, about 7 or less, or the like.

In the present specification, the term "starch" is a mixture of amylose and amylopectin. As a starch, any starch can be used as long as it is commonly commercially available. The ratio of the amylose and amylopectin contained in a starch is different depending on the kind of plant producing the starch. Almost all starches possessed by glutinous rice, glutinous corn and the like are an amylopectin. On the other hand, a starch consisting only of amyloses, containing no amylopectin, can not be obtained from a common plant. Starch is classified into natural starch, a degraded starch and modified starch.

Natural starch is classified into tuber starch and cereal starch depending on the raw material. Examples of tuber starches include potato starch, tapioca starch, sweet potato starch, kudzu starch, bracken starch and the like. Examples of cereal starches include corn starch, wheat starch, rice starch and the like. Examples of natural starches are high amylose starches (for example, high amylose corn starch) or waxy starches. The starch can be a soluble starch. A soluble starch refers to a water-soluble starch obtained by subjecting a variety of treatment on natural starch. The starch may be selected from the group consisting of soluble starch, waxy starch and high amylose starch. The starch may be a modified starch.

The degree of polymerization of the starch used in the present invention is preferably about 1,000 or more, more preferably about 5,000 or more, still more preferably about 10,000 or more, and most preferably about 20,000 or more. The degree of polymerization of the starch used in the present invention is preferably about $1 \times 10^7$ or less, more preferably about $3 \times 10^6$ or less, still more preferably about $1 \times 10^6$ or less and most preferably about $3 \times 10^5$ or less.

An amylopectin is a branched molecule in which a glucose unit(s) is linked with an α-1,6 bond to glucose units which are linked with an α-1,4 bond(s). An amylopectin is contained in natural starch. As an amylopectin, for example, waxy corn starch, which consists of 100% amylopectin, can be used. The degree of polymerization of the amylopectin used in the present invention is preferably about 1,000 or more, more preferably about 5,000 or more, still more preferably about 10,000 or more, and most preferably about 20,000 or more. The degree of polymerization of the amylopectin used in the present invention is preferably about $1 \times 10^7$ or less, more preferably about $3 \times 10^6$ or less, still more preferably about $1 \times 10^6$ or less and most preferably about $3 \times 10^5$ or less.

A glycogen is one kind of glucan constructed of glucose, and is a glucan having a high frequency of branching. A glycogen is widely distributed as a storage polysaccharide for animals and plants in almost all cells in the granule state. In a plant, glycogen is present, for example, in the seed of corn and the like. In a glycogen, typically, sugar chains consisting of glucoses linked with an α-1,4-bond(s) which have an average degree of polymerization of 12 to 18 are linked by an α-1,6-bond(s) at a ratio of around one chain every about 3 units of glucose, to a sugar chain consisting of glucoses linked with an α-1,4-bond(s). In addition, similarly, a sugar chain consisting of glucoses linked by an α-1,4-bond(s) is linked by an α-1,6-bond to a branch linked by an α-1,6-bond(s). For this reason, glycogen forms a network structure. It is also possible to enzymatically synthesize a glycogen. The degree of polymerization of the glycogen used in the present invention is preferably about 500 or more, more preferably about 1,000 or more, still more preferably about 2,000 or more, and most preferably about 3,000 or more. The degree of polymerization of the glycogen used in the present invention is preferably about $1 \times 10^7$ or less, more preferably about $3 \times 10^6$ or less, still more preferably about $1 \times 10^6$ or less and most preferably about $3 \times 10^5$ or less.

Dextrin is one kind of glucan constructed of glucose, and is a glucan having a medium complexity between those of starch and those of maltose. Dextrin may be obtained by partially degrading starch by an acid, an alkyl or an enzyme. The degree of polymerization of the dextrin used in the present invention is preferably about 10 or more, more preferably about 20 or more, still more preferably about 30 or more, and most preferably about 50 or more. The degree of polymerization of the dextrin used in the present invention is preferably about 10,000 or less, more preferably about 9,000 or less, still more preferably about 7,000 or less and most preferably about 5,000 or less.

The enzymatically synthesized branched glucan refers to a branched glucan synthesized using an enzyme. By adding a branching enzyme to the reaction solution upon synthesis of amylose by the SP-GP method, the product can be branched. The extent of branching can be regulated by the added amount of the branching enzyme. Since the enzymatically synthesized branched glucan has a uniform structure as compared with a natural branched glucan, it is very advantageous when use as a pharmaceutical material. For example, the degree of polymerization of the enzymatically synthesized branched glucan used in the present invention is preferably about 20 or more, more preferably about 50 or more, still more preferably about 100 or more, and most preferably about 200 or more. The degree of polymerization of the enzymatically synthesized branched glucan used in the present invention is preferably about $2 \times 10^5$ or less, more preferably about $1 \times 10^5$ or less, still more preferably about $5 \times 10^4$ or less and most preferably about $3 \times 10^4$ or less.

In the present specification, the term "highly branched cyclic glucan" refers to a glucan having an internally branched cyclic structural moiety and an externally branched structural moiety and having a degree of polymerization of 50 or more. The highly branched cyclic glucan may have at least one branch as a whole molecule. The degree of polymerization of the highly branched cyclic glucan as a whole molecule that can be used in the present invention is preferably about 50 or more, more preferably about 60 or more, and still more preferably about 100 or more. The degree of polymerization of the highly branched cyclic glucan as a whole molecule that can be used in the present invention is preferably about 10,000 or less, more preferably about 7,000 or less, and still more preferably about 5,000 or less.

The degree of polymerization of the internally branched cyclic structural moiety present in the highly branched cyclic glucan is preferably about 10 or more, more preferably about 15 or more, and further preferably about 20 or more. The degree of polymerization of the internally branched cyclic structural moiety present in the highly branched cyclic glucan is preferably about 500 or less, more preferably about 300 or less, and further preferably about 100 or less.

The degree of polymerization of the externally branched structural moiety present in the highly branched cyclic glucan is preferably about 40 or more, more preferably about 100 or more, further preferably about 300 or more, and further more preferably about 500 or more. The degree of polymerization of the externally branched structural moiety present in the highly branched cyclic glucan is preferably about 3,000 or less, more preferably about 1,000 or less, further preferably about 500 or less, and further more preferably about 300 or less.

The number of α-1,6-glucoside bonds in the internally branched cyclic structural moiety present in the highly branched cyclic glucan may be at least one, and for example, can be one or more, 5 or more, 10 or more or the like; the number of α-1,6-glucoside bonds in the internally branched cyclic structural moiety can be, for example, about 200 or less, about 50 or less, about 30 or less, about 15 or less, about 10 or less or the like.

As the highly branched cyclic glucan, a highly branched cyclic glucan having one kind of a degree of polymerization may be used alone, or a mixture of highly branched cyclic glucans having a variety of degree of polymerization may be used. Preferably, the degrees of polymerization of the highly branched cyclic glucan is such that the ratio of the degrees of polymerization of the maximum degree of polymerization to the minimum degree of polymerization is about 100 or less, more preferably about 50 or less, and further more preferably about 10 or less.

The highly branched cyclic glucan is preferably a glucan having an internally branched cyclic structural moiety and an externally branched structural moiety and having a degree of polymerization in a range of 50 to 5,000, wherein the internally branched cyclic structural moiety is a cyclic structural moiety formed with an α-1,4-glucoside bond and an α-1,6-glucoside bond, and the externally branched structural moiety is a non-cyclic structural moiety bound to the internally branched cyclic structural moiety. The degree of polymerization of each unit chain of this externally branched structural moiety is, on average, preferably about 10 or more and preferably about 20 or less. The highly branched cyclic glucan and a method for producing the same are described in detail in Japanese Laid-Open Publication No. 8-134104 (Japanese Patent No. 3107358), and this glucan can be produced according to the description of it. The highly branched cyclic glucan is commercially available, for example, as "Cluster Dextrin" from Ezaki Glico Co., Ltd. The degree of polymerization of the highly branched cyclic dextrin used in the present invention is preferably about 50 or more, more preferably about 70 or more, further preferably about 100 or more, most preferably about 150 or more. The degree of polymerization of the highly branched cyclic dextrin used in the present invention is preferably about 10,000 or less, more preferably about 7,000 or less, further preferably about 5,000 or less, and most preferably about 4,000 or less.

In a specific embodiment, the branched glucan can be particulate. It is known that particles having a diameter of about 4 nm or less are excreted from kidney, particles having a diameter of about 4 nm to about 200 nm are circulated in blood for a long time, particles having a diameter of about 200 nm to about 7 ware captured by a reticuloendothelial system, and particles having a diameter of about 7 μm or more obstruct capillary blood vessels. A reticuloendothelial system is distributed in liver and spleen. For this reason, by controlling the particle size of the branched glucan, the pharmacokinetics of the glucuronic acid-containing glucan and a modified product thereof and a conjugate thereof of the present invention in vivo can be controlled. When one intends to circulate the particles in blood for a long time, the particle size of a particulate branched glucan is, as the diameter, preferably about 4 nm or more, more preferably about 10 nm or more, preferably about 200 nm or less, and more preferably about 100 nm or less. The molecular weight of the particulate branched glucan having such a particle size is preferably about $5 \times 10^5$ or more, more preferably about $1 \times 10^6$ or more, preferably about $5 \times 10^7$ or less, and more preferably about $2 \times 10^7$ or less. For example, since it is known that particles having a diameter of 20 to 50 nm are accumulated in cancer cells, when it is intended that the particles are accumulated in cancer cells, the particle size of the particulate branched glucan is, as the diameter, preferably about 10 nm or more, more preferably about 15 nm or more, preferably about 100 nm or less, and more preferably about 50 nm or less. The molecular weight of the particulate branched glucan having such a particle size is preferably about $5 \times 10^5$ or more, more preferably about $1 \times 10^6$ or more, preferably about $2 \times 10^7$ or less, and more preferably about $5 \times 10^6$ or less.

The number of branches in the α-glucan (i.e. the number of α-1,6-glucoside bonds) is preferably about 1 or more, more preferably about 10 or more, further preferably about 30 or more. The number of branches of the α-glucan (i.e. the number of α-1,6-glucoside bonds) is preferably about 5,000 or less, more preferably about 2,000 or less, further preferably about 1,000 or less.

In the branched α-glucan used in the present invention, the ratio of the number of α-1,6-glucoside bonds relative to the number of α-1,4-glucoside bonds ("number of α-1,6-glucoside bonds":"number of α-1,4-glucoside bonds") is preferably 1:1 to 1:10,000, more preferably 1:10 to 1:5,000, further preferably 1:50 to 1:1,000, and further more preferably 1:100 to 1:500.

The α-1,6-glucoside bonds may be randomly distributed in the α-glucan or may be homogeneously distributed in the α-glucan. A distribution to such an extent that a linear chain part(s) of 5 or more saccharide units can be formed in the α-glucan is preferable.

In the present invention, a modified product of the glucan may be used in place of the glucan. Examples of the modified product of the glucan include a modified starch and an esterified product of the glucan explained above. Furthermore, the modified product of the glucan may be a hydroxyl group-modified product or a reducing end-modified product. In addition, as described later, after a glucuronic acid residue is bound to at least one non-reducing end of the glucan, a glucan moiety may be modified.

The modified starch is a starch which was made to have a nature that it is easier to use by subjecting a natural starch to treatment such as hydrolysis, esterification or gelatinization. Wide variety of modified starches having a variety of combinations of a gelatinization initiation temperature, a viscosity of a starch paste, a degree of transparency of a starch paste, stability against aging and the like are available. There are various types of modified starches. An example of such a starch is a starch obtained by immersing starch granules in an acid at a gelatinization temperature or lower of the starch, thereby cutting a starch molecule but not destroying starch granules.

Examples of the modified product of the glucan other than the modified starch include a modified product in which at least one of alcoholic hydroxyl groups of an unmodified glucan is modified (hereinafter, in the present specification, referred to as a "hydroxyl group-modified product of glucan"), a modified product in which some of non-reducing ends of the glucan is modified (hereinafter, in the present specification, referred to as a "non-reducing end-modified product of glucan") and a modified product in which the reducing end of a glucan is modified (hereinafter, in the present specification, referred to as a "reducing end-modified product of glucan").

Examples of the modification at a hydroxyl group include hydroxyalkylation, alkylation, acylation, carboxymethylation, sulfation and phosphorylation. It is preferable that modification at a hydroxyl group is a modification which can be removed with an enzyme in a body. The hydroxyl group-modified product of the glucan is preferably an acylated glucan, and further preferably an acetylated glucan. The frequency of introduction of the modifying group(s) into alcoholic hydroxyl groups can be arbitrarily set at the time of a modification reaction of the glucan. The frequency of introduction of the modifying group(s) into alcoholic hydroxyl groups is expressed as DS, and DS1 means the state where one modifying group per glucose residue is introduced. DS can be calculated by DS=(number of modifying group)/(number of glucose residue). Since there is an OH group at the 2-position, the 3-position and the 6-position in an unmodified glucose residue, theoretically, maximum 3 modifying groups per glucose residue can be introduced. For this reason, the upper limit of DS is usually 3. The frequency of introduction of the modifying group(s) into alcoholic hydroxyl groups is about DS 0.01 or more, more preferably about DS 0.03 or more, further preferably about DS 0.05 or more, particularly preferably about DS 0.07 or more, and most preferably about DS 0.1 or more. The frequency of introduction of modifying group(s) is preferably about DS 1.5 or less, more preferably about DS 1.3 or less, further preferably about DS 1.1 or less, particularly preferably about DS 1.0 or less, and most preferably about DS 0.9 or less. By modifying the glucan, degradation of the glucan in blood or in a body is suppressed.

Examples of modification at a non-reducing end include binding with a targeting molecule such as a mannose residue or a galactose residue. Modification at a non-reducing end will be explained in detail in the following 2.7 and 3. A non-reducing end-modified product is preferably a conjugate with a mannose residue or a conjugate with a galactose residue.

Examples of modification at a reducing end include binding with a monosaccharide, a non-reducing carbohydrate, a biocompatible macromolecule, a liposome constituent component, a glycoside and an amine group-containing low-molecular weight substance. Modification at a non-reducing end will be explained in detail in the following 2.7 and 3.

(1.2) Uronic Acid

Uronic acid is a generic name of carboxylic acids which are derivatives obtained by oxidizing a monosaccharide and in which a hydroxymethyl group at a terminus of the main chain has been changed to a carboxyl group. Uronic acid may also be an acid obtained by oxidizing a primary alcohol group (—CH$_2$OH) farthest from the carbonyl group of a monosaccharide into a carboxyl group (—COOH). Uronic acid can be synthesized by inducing a monosaccharide into a glycoside and then oxidizing its 6-position, or reducing an aldaric acid.

Examples of representative uronic acid include glucuronic acid, galacturonic acid, mannuronic acid and the like. Glucuronic acid is an oxide of glucose, galacturonic acid is an oxide of galactose and mannuronic acid is an oxide of mannose. As uronic acid in the present invention, glucuronic acid is most preferable.

In the method of the present invention, uronic acid-1-phosphate is used. Uronic acid-1-phosphate may be a commercially available one, or may be synthesized by a chemical method, an enzymatic method, or a biological method such as fermentation. Uronic acid may be used for synthesizing uronic acid-1-phosphate.

(2. Method for Producing a Uronic Acid-Containing Glucan)

(2.1) Glucuronic Acid-1-Phosphate

As glucuronic-1-phosphate utilized in the present invention, glucuronic acid-1-phosphate synthesized by a chemical method, an enzymatic method, or a biological method such as fermentation can be used. Particularly, glucuronic acid-1-phosphate synthesized by a chemically oxidizing reaction of glucose-1-phosphate is preferable. A method of synthesizing glucuronic acid-1-phosphate by a chemically oxidizing reaction of glucose-1-phosphate is disclosed in Heeres et al., Carbohydr. Res. 1997, 299, 221-227.

As glucuronic acid-1-phosphate, any of glucuronic acid-1-phosphate not in a salt form and glucuronic acid-1-phosphate in the form of a salt can be used. For example, a metal salt of glucuronic acid-1-phosphate can be used, and an alkali metal salt of glucuronic acid-1-phosphate (for example, disodium glucuronic acid-1-phosphate and dipotassium glucuronic acid-1-phosphate) can be used.

(2.2) α-Glucan Phosphorylase

In the present specification, "α-glucan phosphorylase" and "GP" are interchangeably used unless otherwise indicated. In the present specification, the term "α-glucan phosphorylase" means an enzymes having α-glucan phosphorylase activity. α-Glucan phosphorylase is classified in EC 2.4.1.1. α-Glucan phosphorylase activity refers to an activity catalyzing a reaction producing glucose-1-phosphate and partial degraded products of an α-1,4-glucan from inorganic phosphate and the α-1,4-glucan, or the reverse reaction thereof. α-Glucan phosphorylases in some cases are also called phosphorylase, starch phosphorylase, glycogen phosphorylase, maltodextrin phosphorylase, or the like. α-Glucan phosphorylase can also catalyze an α-1,4-glucan synthesizing reaction which is the reverse reaction relative to phosphorolysis. In which direction a reaction proceeds depends on the amount of substrate. Since the amount of inorganic phosphate is abundant in vivo, α-glucan phosphorylase causes a reaction to proceed in the phosphorolysis direction. If the amount of inorganic phosphate is small, the reaction proceeds in the α-1,4-glucan synthesizing direction.

It seems that all known α-glucan phosphorylases need pyridoxal 5'-phosphate for activation, and share a similar catalytic mechanism. Although enzymes derived from different origins are different with respect to preference of substrate and form of regulation, all α-glucan phosphorylases belong to a large group including many α-glucan phosphorylases. This large group includes glycogen phosphorylase derived from bacteria, yeast and animals, starch phosphorylase derived from plants, and maltodextrin phosphorylase derived from bacteria. α-Glucan phosphorylase is believed to be universally present in various plants, animals, and microorganisms which can store starch or glycogen.

Plant α-glucan phosphorylases are classified into types L and type H, depending on their affinity for glycogen. Type L α-glucan phosphorylase refers to α-glucan phosphorylases having a low affinity for glycogen.

Generally, type L α-glucan phosphorylases prefer maltodextrin, amylose and amylopectin over glycogen as a substrate (Hiroyuki Mori, et al., "A Chimeric α-Glucan phosphorylase of Plant Type L and H Isozymes", The Journal of Biological Chemistry, 1993, vol. 268, No. 8, pp. 5574-5581). Type H α-glucan phosphorylase refers to α-glucan phosphorylases having high affinity for glycogen.

Generally, type H α-glucan phosphorylases have extremely high affinity for various glucans, including glycogen. Type L α-glucan phosphorylase and type H α-glucan phosphorylase are also different in their localization in plant cells. Type H α-glucan phosphorylase is localized in a cytosol and type L α-glucan phosphorylase is localized in plastid.

It has been reported that a minimum primer molecule for a glucan synthesizing reaction of α-glucan phosphorylase is maltotetraose. It has been also reported that a minimum substrate effective for a glucan degradation reaction is maltopentaose. Generally, it has been thought that these are characteristics common to α-glucan phosphorylases.

However, in recent years, it has been reported that α-glucan phosphorylase derived from *Thermus thermophilus* and α-glucan phosphorylase derived from *Thermococcus litoralis* have different substrate specificity from that of other α-glucan phosphorylases. Regarding these α-glucan phosphorylases, a minimum primer for glucan synthesis is maltotriose, and a minimum substrate for glucan degradation is maltotetraose. Furthermore, recently, genome analysis of various bacteria had been done, and the base sequences and amino acid sequences of α-glucan phosphorylases derived from various bacteria are reported. The base sequences and amino acid sequences of α-glucan phosphorylases derived from *Aquifex aeolicus*, α-glucan phosphorylases derived from *Thermotoga maritima*, maltodextrin phosphorylase derived from *Thermococcus zilligii*, α-glucan phosphorylases derived from *Thermoanaerobacter pseudethanolicus* and the like had been reported.

It is preferable that α-glucan phosphorylases used in the present invention is α-glucan phosphorylases derived from *Aquifex aeolicus* VF5.

The base sequence of α-glucan phosphorylases derived from *Aquifex aeolicus* VF5 is set forth in SEQ ID NO: 1, and its amino acid sequence is set forth in positions 1-692 of SEQ ID NO: 2. The amino acid sequence of α-glucan phosphorylases derived from *Aquifex aeolicus* VF5 has about 21% to about 24% sequence identity with the amino acid sequence of plant α-glucan phosphorylases, about 34% sequence identity with the amino acid sequence of α-glucan phosphorylases derived from *Thermus thermophilus*, and about 38% sequence identity with the amino acid sequence of α-glucan phosphorylases derived from *Thermococcus litoralis*. It has about 38% sequence identity with the amino acid sequence of α-glucan phosphorylases derived from *Thermotoga maritima*, about 38% sequence identity with the amino acid sequence of maltodextrin phosphorylases derived from *Thermococcus zilligii*, and about 33% sequence identity with those of *Thermoanaerobacter pseudethanolicus*.

In the present specification, an enzyme "derived from" an organism, means not only that the enzyme is directly isolated from the organism, but also refers to an enzyme obtained by utilizing the organism in any form. For example, when a gene encoding an enzyme obtained from an organism is introduced into *Escherichia coli*, and the enzyme is isolated from that *Escherichia coli*, the enzyme is referred to as being "derived from" the organism.

In the present specification, "identity" of a sequence (for example, an amino acid sequence, a base sequence and the like) refers to the degree of occurrence of the same amino acid (base when base sequences are compared) between two sequences. Identity is generally determined by comparing two amino acid sequences or two base sequences, and comparing these two sequences which are aligned in an optimal format, which can contain additions or deletions.

In the present specification, the identity of sequences is calculated using maximum matching of GENETYX-WIN Ver. 4.0 (Genetics Co., Ltd.). This program aligns sequence data to be analyzed, and sequence data to be compared so that amino acid pairs matched between sequences become greatest while substitution and deletion are considered, and thereupon, gives a score to each of Matches, Mismatches, and Gaps, calculates a sum, outputs alignment at the smallest sum, and calculates identity thereupon (Reference: Takashi, K., and Gotoh, O. 1984. Sequence Relationships among Various 4.5 S RNA Species J. Biochem. 92:1173-1177).

For example, the amino acid sequence of α-glucan phosphorylases used in the present invention can be same with SEQ ID NO: 2, i.e., it can have 100% identity. In another embodiment, as long as having activity to transfer glucuronic acid to non-reducing end of a glucan, this amino acid sequence may be altered in up to a certain number of amino acids compared with a reference amino acid sequence. Such alterations can be selected from the group consisting of a deletion, a substitution (including conservative substitution and non-conservative substitution), or an insertion of at least 1 amino acids. This alteration may occur at a position of an amino terminus or a carboxyl terminus of the amino acid sequence of SEQ ID NO: 2, or may occur at any position other than these termini. Alteration of an amino acid residue may be interspersed with one residue, or a few residues may be contiguous. For example, α-glucan phosphorylases used in the present invention may be added with amino acid residues (preferably about 20 or less residues, more preferably about 10 or less residues, and further preferably about 5 or less residues) at either terminus of the amino acid sequence of SEQ ID NO: 2, for the reasons such as to make ease of purification of the enzyme, to increase stability, or the like.

The α-glucan phosphorylase used in the present invention has an amino acid sequence which has preferably about 50% or more, more preferably about 60% or more, further more preferably about 70% or more, still more preferably about 80% or more, particularly more preferably about 90% or more, and most preferably about 95% or more identity with an amino acid sequence of SEQ ID NO: 2 and has an activity transferring a glucuronic acid to a non-reducing end of the glucan. The α-glucan phosphorylase used in the present invention can have an amino acid sequence which has about 96% or more, about 97% or more, about 98% or more, or about 99% more sequence identity with amino acid sequence of SEQ ID NO: 2.

The amount of the α-glucan phosphorylase contained in a solution at the start of the reaction is preferably about 0.01 U/ml or more, more preferably about 0.1 U/ml or more, particularly preferably about 0.5 U/ml or more, and most preferably about 1 U/ml or more. The amount of the α-glucan phosphorylase contained in a solution at the start of the reaction is preferably about 1,000 U/ml or less, more preferably about 100 U/ml or less, particularly preferably about 50 U/ml or less, and most preferably about 20 U/ml or less. If the weight of α-glucan phosphorylase is too large, it may became easy to aggregate the enzyme denatured during the reaction. If the amount used is too small, reaction itself occurred, but the yield of glucan may be lowered. It is noted that unit amount of α-glucan phosphorylase is defined as follows:

Regarding one unit of α-glucan phosphorylase, an α-glucan phosphorylase activity which produces 1 μmol inorganic phosphate (Pi) per one minute shall be one unit (U or Unit). This measurement of α-glucan phosphorylase activity quantitates free inorganic phosphate (Pi) produced from G-1-P. After 200 μl of a reaction solution (containing 12.5 mM G-1-P, 1% dextrin and an enzyme solution in a 100 mM acetate buffer (pH 6.0)) is incubated at 50° C. for 15 minutes, 800 μl of a molybdenum regent (15 mM ammonium molybdate, 100 mM zinc acetate) is added, and this is stirred to stop the reaction. 200 μl of 568 mM ascorbic acid (pH 5.8) is added, followed by mixing. After incubation at 30° C. for 15 minutes, an absorbance at 850 nm is measured using a spectrophotometer. An absorbance is measured similarly using inorganic phosphate having the known concentration, and a standard curve is produced. An absorbance value obtained for a sample is fitted to this standard curve, and the amount of inorganic phosphate in the sample is determined. Inorganic phosphate is quantitated as a phosphoric acid ion. The amount of glucose-1-phosphate is not quantitated.

The α-glucan phosphorylase may be purified or unpurified. Purified α-glucan phosphorylase is preferable. The α-glucan phosphorylase may be immobilized or may not be immobilized. It is preferable that the α-glucan phosphorylase is immobilized. As the method of immobilization, methods well-known to those skilled in the art such as a carrier binding method (for example, covalent binding method, ion binding method, or physical adsorbing method), a crosslinking method or an inclusion method (lattice type or microcapsule type) can be used. It is preferable that the α-glucan phosphorylase is immobilized on a carrier.

(2.3 Production of α-Glucan Phosphorylase)

α-Glucan phosphorylase used in the present invention can be directly isolated from an organism producing α-glucan phosphorylase, such as the aforementioned organisms, present in the natural world. Alternatively, α-glucan phosphorylase used in the present invention may be isolated from a microorganism (for example, bacteria, fungi and the like) which has been genetically modified with a gene encoding α-glucan phosphorylase isolated from the aforementioned organism.

In a preferable embodiment, α-glucan phosphorylase derived from *Aquifex aeolicus* VF5 is produced by chemically synthesizing a gene fragment of SEQ ID NO: 1, constructing an expression vector containing this gene fragment, introducing this expression vector into a microorganism to make a recombinant microorganism, culturing this recombinant microorganism to produce α-glucan phosphorylase, and recovering produced α-glucan phosphorylase. An enzymatic production method by gene recombination is well-known to those skilled in the art. A host microorganism used in the present invention includes a prokaryote and a eukaryote, and a mesophile is preferable. Examples of a particularly preferable microorganism include, but not limited to, *Escherichia coli*.

α-glucan phosphorylase used in the method of the present invention can be prepared, for example, as follows. First, a microorganism (for example, bacteria, fungi and the like) producing α-glucan phosphorylase is cultured. This microorganism may be a microorganism directly producing the α-glucan phosphorylase. Alternatively, a gene encoding the α-glucan phosphorylase may be cloned, a microorganism (for example, bacteria, fungi and the like) which is advantageous for expressing the α-glucan phosphorylase may be genetically modified with the resulting gene to obtain a recombinant microorganism, and α-glucan phosphorylase may be obtained from the resulting microorganism.

A microorganism used in genetic modification with α-glucan phosphorylase gene can be easily selected, taking various conditions such as ease of expression of the α-glucan phosphorylase, ease of culturing, proliferation speed and safety into consideration. Since the α-glucan phosphorylase preferably contains no amylase as a contaminant, it is preferable to use a microorganism (for example, bacteria, fungi and the like) which does not produce amylase or expresses amylase only at a low level, for genetic modification. For genetic modification with α-glucan phosphorylase, it is preferable to use a mesophilic microorganism such as *Escherichia coli* or *Bacillus subtilis*. α-glucan phosphorylase produced using a microorganism (for example, bacteria, fungi and the like) which does not produce amylase or expresses amylase only at a low level containing substantially no amylase is preferably used in the method of the present invention.

Genetic recombination of a microorganism (for example, bacteria, fungi and the like) with a cloned gene can be performed according to methods well-known to those skilled in the art. When a cloned gene is used, it is preferable to operably link this gene to a constitutive promoter or an inducible promoter. The "operably linked" refers to that a promoter and a gene are linked so that expression of the gene is regulated by the promoter. When an inducible promoter is used, it is preferable to perform culturing under inducing conditions. Various inducible promoters are known to those skilled in the art.

The "expression vector" refers to a vehicle that is operably linked to an objective gene so that the objective gene is transcript and translated, and optionally further having factors necessary for replication in a microorganism and selection of a recombinant. In addition, when secretion production of an expressed product (α-glucan phosphorylase) is intended, a base sequence encoding a secretion signal peptide is linked upstream of a DNA coding for the objective protein in the correct reading frame. Base sequences encoding signal peptides are known to those skilled in the art. It is well-known to those skilled in the art that the type of an expression vector can vary depending on a microbiological host cell used.

Preferable expression vectors include pTRC99A (manufactured by Pharmacia) that is also expressible in *Escherichia coli*, and the like. In order to operably link an α-glucan phosphorylase gene to factors necessary for transcription and translation in the aforementioned expression vector, an objective α-glucan phosphorylase gene should be processed in some cases. Examples include the case where the distance between a promoter and a coding region is too long, and reduction in a transcription efficiency is predicted, the case where the distance between a ribosome binding site and a translation initiation codon is not suitable, and the like. The procession means include digestion with a restriction enzyme, digestion with an exonuclease such as Bal31 and ExoIII, or introduction of site-directed mutagenesis using a single-stranded DNA such as M13 or PCR.

A base sequence encoding α-glucan phosphorylase used in the present invention can be changed in conformity with a codon usage in an organism into which the sequence is introduced for expression. Codon usage reflects the usage in a gene which is highly expressed in the organism. For example, when expression is intended in *Escherichia coli*, the sequence can be made to be optimal for expression in *Escherichia coli* according to the published codon usage table (for example, Sharp, et al., Nucleic Acids Research 16, No. 17, p. 8207 (1988)).

In order to produce an objective gene by a transformant strain into which an expression vector has been introduced, and has acquired the ability to express α-glucan phosphorylase, the condition is appropriately selected depending on a kind of a host cell to be used, and a kind of an expression regulating factor in an expression vector, as well as the expressed substance. For example, an usual shaking culture method can be used.

A medium used is not particularly limited as long as the host microorganism used is grown. In a medium, in addition to a carbon source and a nitrogen source, inorganic salts such as salts of phosphoric acid, $Mg^{2+}$, $Ca^{2+}$, $Mn^{2+}$, $Fe^{2+}$, $Fe^{3+}$, $Zn^{2+}$, $Co^{2+}$, $Ni^{2+}$, $Na^+$, $K^+$ and the like can be used alone, or by appropriately mixing them, if necessary. In addition, as necessary, various inorganic substances or organic substances necessary for growing the transformant or production of the enzyme may be added.

A temperature for culture can be selected so as to be suitable for growing a transformant used. Usually, the temperature is 15° C. to about 60° C. In a preferred embodiment of the present invention when a mesophilic microorganism is used, culturing at about 25° C. to about 40° C. is preferable. Culturing of a transformant strain is continued for a sufficient time to express α-glucan phosphorylase. In a preferred embodiment of the present invention, the culturing time is about 24 hours.

When an expression vector having an inducible promoter is used, expression can be controlled by addition of an inducer, change of a culturing temperature, and adjustment of medium components. For example, when an expression vector having a lactose inducible promoter is used, expression can be induced by adding isopropyl-β-D-thiogalactopyranoside (IPTG).

For example, in the case where the expressed α-glucan phosphorylase is accumulated in a transformed cell, after the transformed cells are cultured in an appropriate condition, the cells are recovered by centrifuging or filtering the culture, and then suspended in a suitable buffer. Then the cells are crushed using ultrasound treatment or the like, and centrifuged or filtrated to obtain a supernatant containing α-glucan phosphorylase. Alternatively, in the case where the expressed α-glucan phosphorylase is secreted out side of a transformed cell, after the transformed cells are cultured in an appropriate condition, the transformed cells are removed by centrifuging or filtering the culture to obtain a supernatant containing α-glucan phosphorylase. Both in the case of when the α-glucan phosphorylase is accumulated in a transformed cell or the case where the expressed α-glucan phosphorylase is secreted out of a transformed cell, thus-obtained supernatant that contains α-glucan phosphorylase is concentrated by a usual means (for example, salting-out, solvent precipitation, or ultrafiltration) to obtain a fraction containing the α-glucan phosphorylase. This fraction is subjected to filtration, centrifugation or desalting to obtain a crude enzyme solution. Further, a crude enzyme or a purified enzyme having improved specific activity is obtained by purifying the crude enzyme solution by a method of appropriately combining conventional enzyme purifying means such as lyophilization, isoelectric focusing, ion exchange chromatography and crystallization. When an enzyme degrading an α-glucan such as α-amylase and an enzyme degrading glucose-1-phosphate such as phosphatase is not contained, the crude enzyme as it is can be used in a reaction thereafter.

Since *Aquifex aeolicus* VF5-derived α-glucan phosphorylase is thermostable, when a gene encoding this α-glucan phosphorylase is expressed in a mesophilic microorganism such as *Escherichia coli*, the expressed α-glucan phosphorylase can be simply and easily purified. Briefly, by heat-treating an enzyme fraction containing α-glucan phosphorylase derived from *Aquifex aeolicus* VF5 at 60° C., contaminating enzymes are insolubilized. The insolubles are removed by centrifugation or the like and dialyzed to obtain a purified enzyme liquid.

(2.4) Production of Uronic Acid-Containing Glucan

The uronic-acid containing glucan of the present invention can be produced by a method including a step of allowing to react a reaction solution containing α-glucan phosphorylase (for example, α-glucan phosphorylase derived from *Aquifex aeolicus* VF5) which can catalyze a reaction of transferring glucuronic acid-1-phosphate, a glucan, and a glucuronic acid residue to a non-reducing end of a glucan. By using a glucan modified product in place of a glucan in this method, a modified product of the uronic acid-containing glucan can be produced. As an example, a method using a glucan will be explained below.

Figure 1:
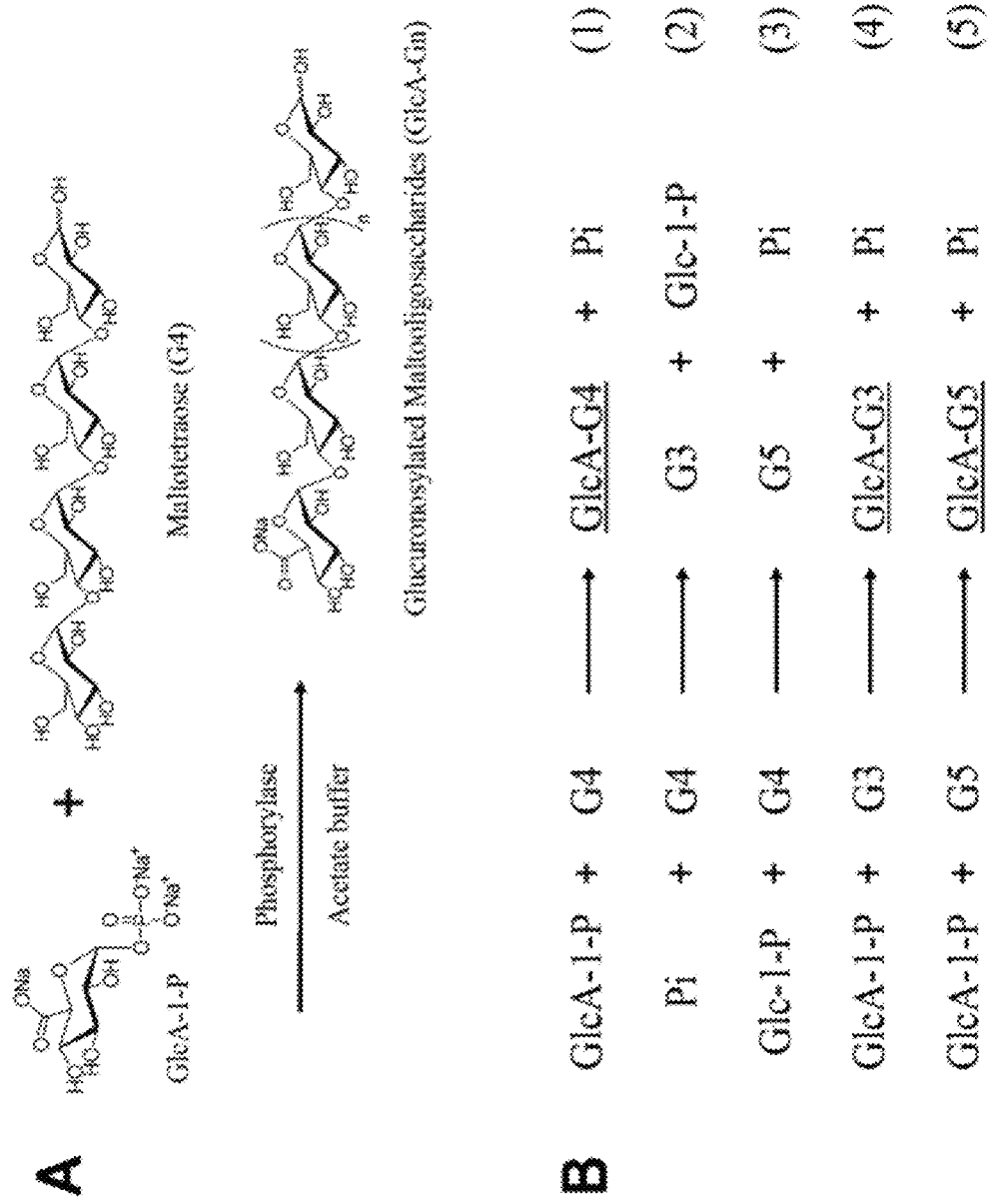
FIG. 1 is a schematic view of a reaction of transferring only one molecule of a glucuronic acid residue to a non-reducing end of a linear glucan. A: This shows a reaction in which a maltooligosaccharide in which glucuronic acid is bound to a non-reducing end (Glucuronosylated Maltooligosaccharide) is generated by allowing α-glucan phosphorylase (shown as "Phosphorylase" in FIG. 1) act on glucuronic acid-1-phosphate (GlcA-1-P) and maltotetraose (Maltotetraose). In this schematic view, as an example of the linear glucan, maltotetraose is shown. A reaction which occurs in this reaction solution will be explained in more detail in B. B: This shows the reason why not only GlcA-G4 is generated, but also GlcA-G3, GlcA-G5, and the like are generated as a byproduct, in the reaction of A. The equation (1) is a main reaction of glucan phosphorylase, and this reaction generates GlcA-G4 and Pi. The equation (2) shows a reaction in which glucan phosphorylase phosphorolyzes G4 using Pi generated by the equation (1) to generate G3 and Glc-1-P. The equation (3) shows a reaction in which glucan phosphorylase acts on Glc-1-P and G4 generated by the equation (2) to generate G5 and Pi. The equation (4) shows a reaction in which glucan phosphorylase acts on G3 and GlcA-1-P generated by the equation (2) to generate GlcA-G3 and Pi. The equation (5) shows a reaction in which glucan phosphorylase acts on G5 and GlcA-1-P generated by the equation (3) to generate GlcA-G5 and Pi. Since such a variety of reactions occurs in the reaction solution, disproportionation of the length of glucan chains occurs and, as a result, when maltotetraose having a degree of polymerization of 4 is used as a starting material, a variety of glucuronic acid-containing maltooligosaccharides having a degree of polymerization of glucose residues of 3 or more are obtained.
Figure 2:
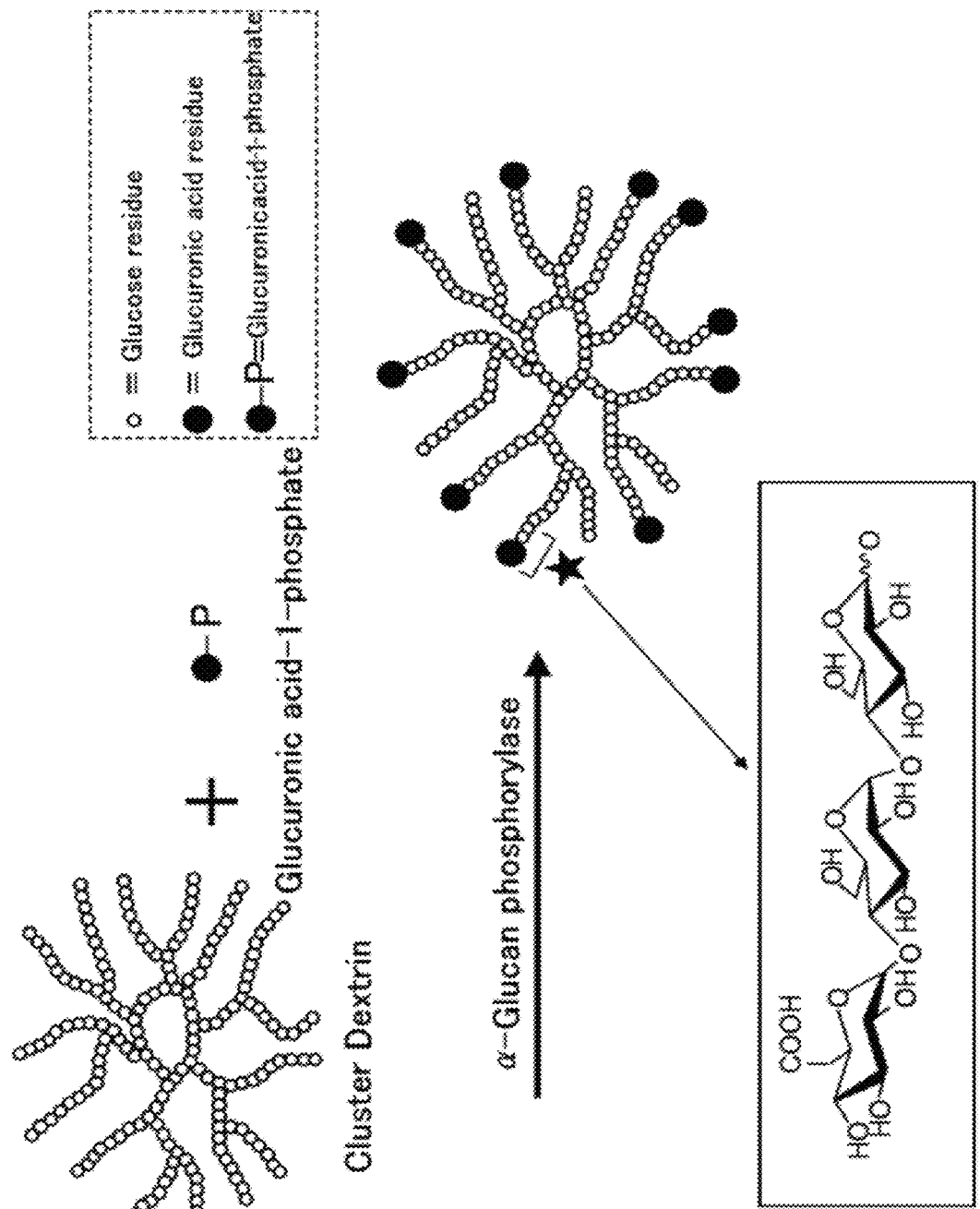
FIG. 2 is a schematic view of a reaction of transferring a glucuronic acid residue to a non-reducing end of a branched glucan.

FIG. 1 shows one example of an outline of a method for producing a uronic acid-containing glucan containing a glucuronic acid residue on a non-reducing end of a linear glucan. In the reaction shown in FIG. 1, when a linear glucan is used as a receptor, only one molecule of glucuronic acid is transferred to a non-reducing end of the linear glucan. FIG. 2 shows one example of an outline of a method for producing a uronic acid-containing glucan containing a glucuronic acid residue on non-reducing ends of a branched glucan.

Figure 3:
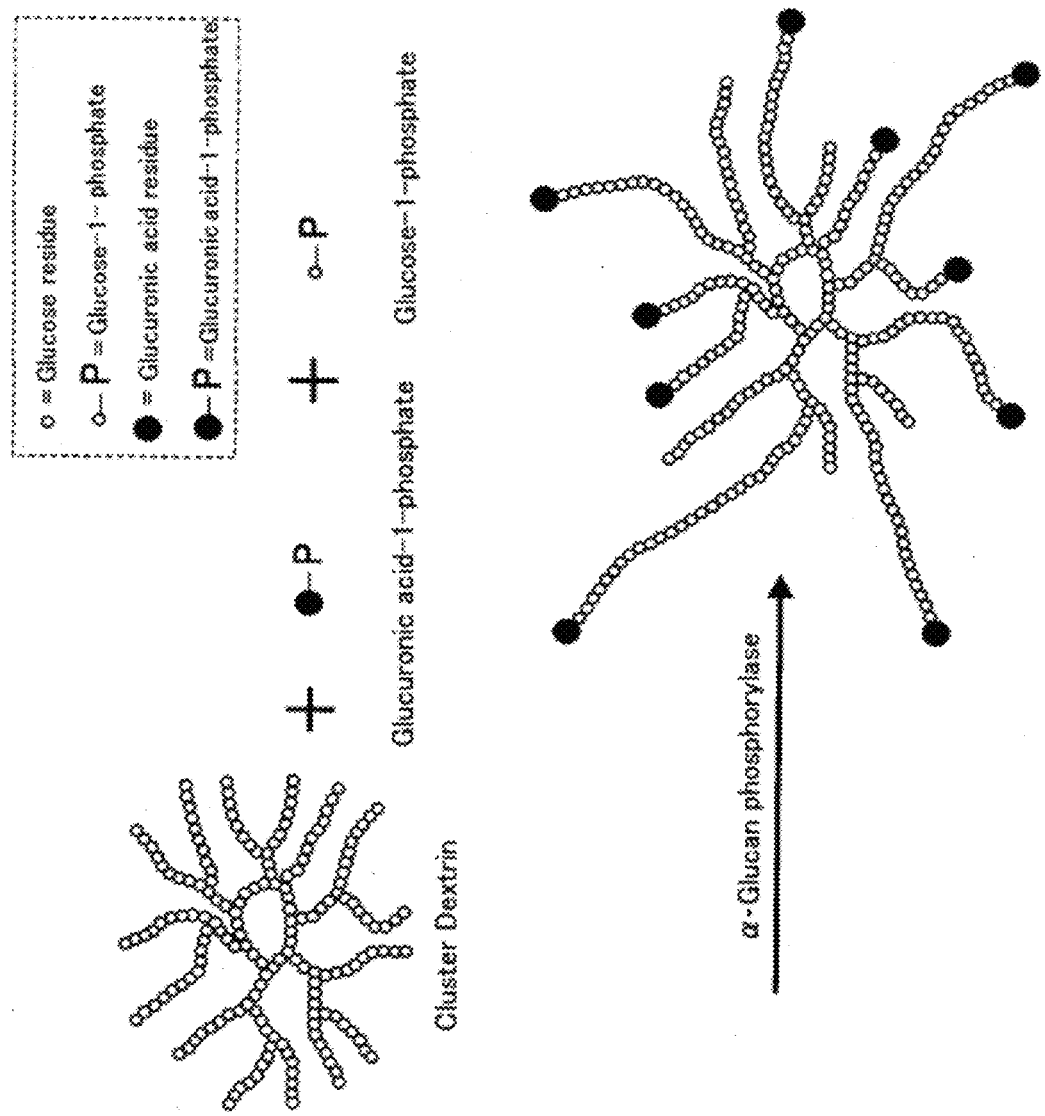
FIG. 3 is a schematic view of a reaction in which an enzymatic reaction is performed under the condition that glucuronic acid-1-phosphate and glucose-1-phosphate are coexistent, and transfer of a glucose residue to a non-reducing end of a unit chain of the branched glucan and transfer of a glucuronic acid residue occur simultaneously.

First, a reaction solution is prepared. The reaction solution can be prepared, for example, by adding glucuronic acid-1-phosphate, a glucan, and α-glucan phosphorylase to a suitable solvent. If necessary, any buffer and inorganic salts for the purpose of adjusting the pH, as far as an enzymatic reaction is not inhibited, may be added to this reaction. If necessary, glucose-1-phosphate which is an original substrate of α-glucan phosphorylase may be added to this reaction solution. In the case of a reaction where glucuronic acid-1-phosphate and glucose-1-phosphate are coexistent, a reaction of binding a glucose residue to a non-reducing end of a receptor glucan and a reaction of binding a glucuronic acid residue are simultaneously performed (for example, see FIG. 3). When a glucuronic acid residue is bound to a non-reducing end of the glucan, α-glucan phosphorylase cannot further transfer a molecule to a non-reducing end of a glucuronic acid residue. However, when a glucose residue is bound to a non-reducing end of a glucan, α-glucan phosphorylase can further transfer a glucose residue or a glucuronic acid residue to a non-reducing end of a resulting molecule. For this reason, when glucose-1-phosphate is coexistent, the chain length of the glucan can be extended. Therefore, the structure of the finally obtained uronic acid-containing glucan is controlled by a ratio between added glucuronic acid-1-phosphate and added glucose-1-phosphate. If necessary, an enzyme selected from the group consisting of a debranching enzyme, a branching enzyme, 4-α-glucanotransferase and a glycogen debranching enzyme may be added to this reaction solution.

Then, the reaction solution is reacted, if necessary, by heating by a method known in the art. The reaction temperature can be any temperature, as far as the effect of the present invention is obtained. The reaction temperature can be representatively a temperature of about 30° C. to about 90° C. It is preferable that the temperature of a solution in this reaction step is such a temperature that, after a predetermined reaction time, about 50% or more, more preferably about 80% or more activity of the activity of the α-glucan phosphorylase contained in this solution before the reaction remains. The reaction temperature is preferably about 35° C. to about 80° C., more preferably about 35° C. to about 70° C., further more preferably about 35° C. to about 65° C. α-Glucan phosphorylase derived from *Aquifex aeolicus* VF5 is a thermostable enzyme, and its optimal reaction temperature is about 80° C. to 90° C. From the viewpoint of the reaction speed, it is preferable that the reaction temperature is high to some extent. On the other hand, from the viewpoint of the optimal reaction temperature of an enzyme, a reaction at about 80° C. to 90° C. is possible. However, from the viewpoint of stability of the resulting product, stability of glucuronic acid-1-phosphate and glucose-1-phosphate, and the like, it is preferable that the reaction temperature is slightly lower than the optimal reaction temperature of the α-glucan phosphorylase derived from *Aquifex aeolicus* VF5. The reaction temperature is preferably about 30° C. or higher, more preferably about 35° C. or higher, further preferably about 40° C. or higher. In a particular embodiment, the reaction temperature may be about 45° C. or higher or about 50° C. or higher. The reaction temperature is preferably about 90° C. or lower, more preferably about 80° C. or lower, further preferably about 70° C. or lower. In a particular embodiment, the reaction temperature may be about 65° C. or lower or about 60° C. or lower.

The reaction time can be set in any time period, in view of the reaction temperature and remaining activity of an enzyme. The reaction time is representatively about 1 hour to about 100 hours, more preferably about 1 hour to about 72 hours, further more preferably about 2 hours to about 36 hours, and most preferably about 2 hours to about 24 hours. In a particular embodiment, the reaction time may be, for example, about 1 hour or longer, about 2 hours or longer, about 5 hours or longer, about 10 hours or longer, about 12 hours or longer, or about 24 hours or longer. In a particular embodiment, the reaction time may be, for example, about 100 hours or shorter, about 72 hours or shorter, about 60 hours or shorter, about 48 hours or shorter, about 36 hours or shorter, or about 24 hours or shorter.

Heating may be performed using any means, but it is preferable that heating is performed with stirring so as to homogeneously transmit the heat to the whole solution. The solution is stirred by placing it into, for example, a reaction tank made of stainless steel, provided with a warm water jacket and a stirring device.

Furthermore, in the method of the present invention, at least one of glucuronic acid-1-phosphate, a glucan, and α-glucan phosphorylase may be further added to a reaction solution at a stage where the reaction has proceeded to some extent.

As described above, a solution containing a uronic acid-containing glucan is produced.

After completion of the reaction, in the reaction solution, if necessary, an enzyme in the reaction solution can be inactivated by, for example, heating at 100° C. for 10 minutes. Alternatively, a post step may be performed without performing treatment of inactivating an enzyme. The reaction solution may be stored as it is, or may be treated in order to isolate the produced uronic acid-containing glucan.

After completion of the reaction, after the uronic acid-containing glucan is purified, or before the uronic acid-containing glucan is purified, a hydroxyl group-modified product of the uronic acid-containing glucan may be produced by modifying at least one of alcoholic hydroxyl groups of a glucan moiety of the resulting uronic acid-containing glucan. It is preferable that modification is performed after purification of the uronic acid-containing glucan. Modification can be performed according to a method known in the art. Examples of modification include hydroxyalkylation, alkylation, acylation, carboxymethylation, sulfation, and phosphorylation. Acylation is preferable, and acetylation is more preferable. By modifying a reducing end of the glucan after producing the uronic acid-containing glucan or a hydroxyl group-modified product of the uronic acid-containing glucan, a reducing end-modified product of the uronic acid-containing glucan or a hydroxyl group-modified product of the uronic acid-containing glucan may be produced. Further, a non-reducing end of these glucan moiety to which uronic acid is not bound, may be modified. Binding of a uronic acid residue to the glucan, modification of a hydroxyl group, modification of a reducing end, and modification of some of non-reducing ends with a modifying group other than a uronic acid residue may be performed in any order.

(2.5 Purification of Uronic Acid-Containing Glucan)
<Purification Method>

The produced uronic acid-containing glucan (or a modified product thereof) can be purified as necessary. Examples of the impurities removed by purification include inorganic phosphate, glucuronic acid-1-phosphate, inorganic salts and the like. Examples of a method of purifying a glucan include a method using an organic solvent (T. J. Schoch et al., J. American Chemical Society, 64, 2957 (1942)) and a method not using an organic solvent.

Examples of the organic solvent which can be used in purification using the organic solvent include acetone, n-amyl alcohol, pentazole, n-propyl alcohol, n-hexyl alcohol, 2-ethyl-1-butanol, 2-ethyl-1-hexanol, lauryl alcohol, cyclohexanol, n-butyl alcohol, 3-pentanol, 4-methyl-2-pentanol, d,l-borneol, α-terpineol, isobutyl alcohol, sec-butyl alcohol, 2-methyl-1-butanol, isoamyl alcohol, tert-amyl alcohol, menthol, methanol, ethanol and ether.

As an example of the purification method not using an organic solvent, there is a method of removing inorganic phosphate, glucuronic acid-1-phosphate, and inorganic salts by subjecting a uronic acid-containing glucan to membrane fractionation using an ultrafiltration membrane or chromatography, without precipitating the uronic acid-containing glucan dissolved in water, after the uronic acid-containing glucan production reaction.

Examples of the ultrafiltration membrane which can be used in purification include an ultrafiltration membrane of a molecular weight cut off of about 1,000 to about 100,000, preferably about 5,000 to about 50,000, more preferably about 10,000 to about 30,000 (UF membrane unit manufactured by DAICEL).

Examples of a support which can be used in chromatography include a support for gel filtration chromatography, a support for ligand exchange chromatography, a support for ion-exchange chromatography and a support for hydrophobic chromatography.

(2.6) Outline Regarding Carbohydrate Synthesis Utilizing α-Glucan Phosphorylase

Figure 4:
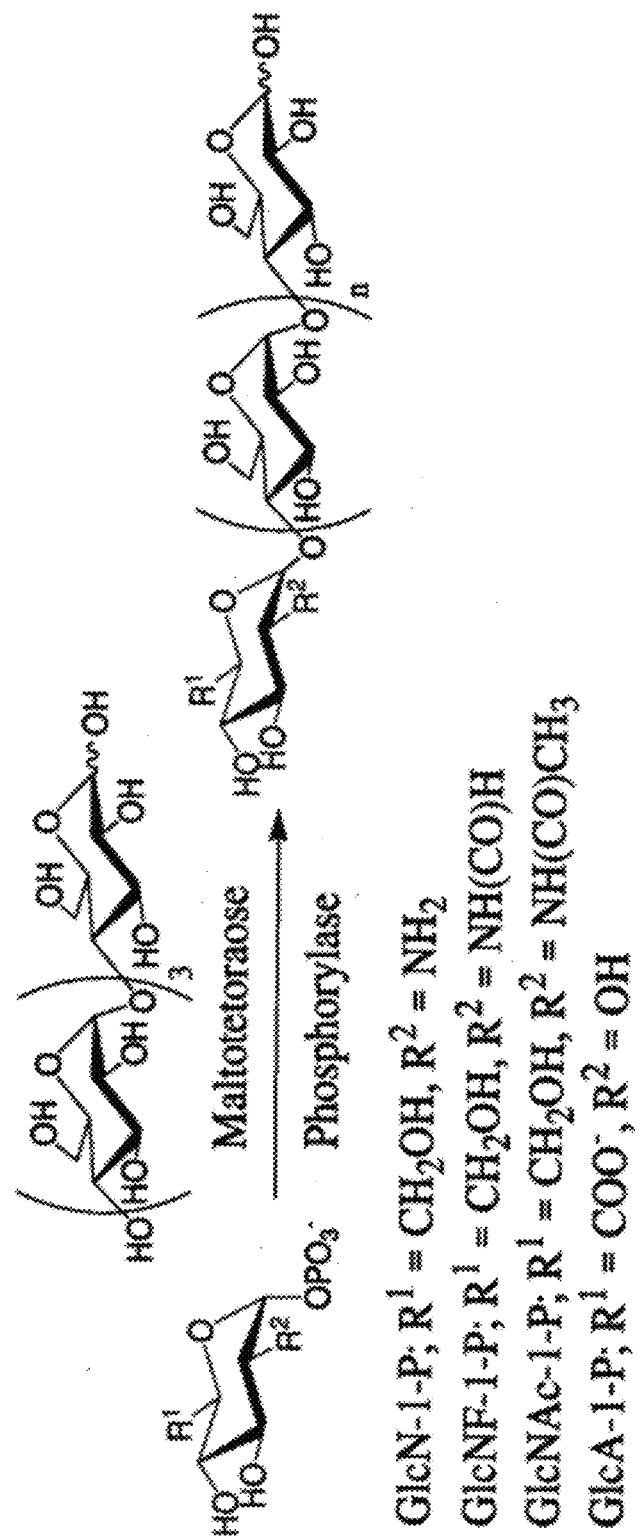
FIG. 4 is a schematic view which summarizes a reaction of α-glucan phosphorylase. This drawing also shows that as a result of disproportionation of the glucan, a mixture of saccharides having a variety of degree of polymerization is obtained as in FIG. 1.

Since a saccharide chain extending reaction using an enzyme as a catalyst proceeds under a mild condition using a non-protected substrate, and control of regioselectivity and stereoselectivity is easy, it is useful in synthesizing an oligosaccharide chain having a clear structure. It is known that phosphorylase (EC 2.4.1.1) recognizes α-D-glucose-1-phosphate (Glc-1-P) as a substrate, and catalyzes a saccharide chain extension reaction that produces an α-1,4-glucan. It is thought that, if phosphorylase can recognize more kinds of sugar phosphate esters as a substrate, this leads to new saccharide chain synthesis. From such a point of view, we have already reported that phosphorylase recognizes α-D-xylose-1-phosphate as a substrate, and catalyzes a reaction of enzymatic xylosylation of a maltooligosaccharide (Reference 1 (M. Nawaji, H. Izawa, Y. Kaneko, J. Kadokawa, J. Carbohydr. Chem., 2008, 27, 214)). In the present study, we adopted α-D-glucosamine-1-phosphate (GlcN-1-P) (Reference 2 (M. Nawaji, H. Izawa, Y. Kaneko, J. Kadokawa, Carbohydr. Res., 2008, 343, 2692)) and derivatives thereof (N-formylglucosamine-1-phosphate (GlcNF-1-P), N-acetylglucosamine-1-phosphate (GlcNAc-1-P)), and glucuronic acid-1-phosphate (GlcA-1-P) as new substrates, and studied an enzymatic reaction of saccharide chain extension on a maltooligosaccharide with phosphorylase (FIG. 4).

Figure 5:
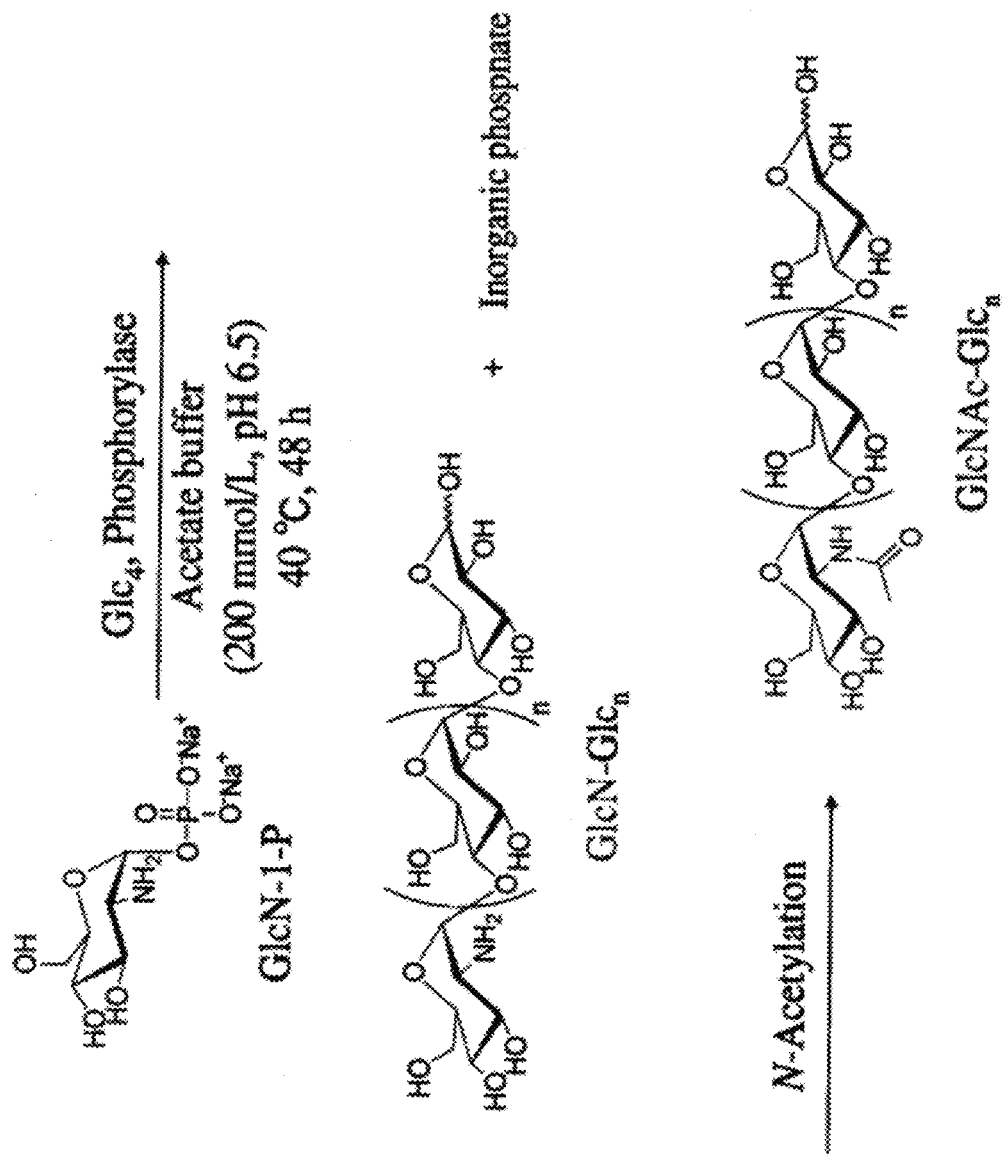
FIG. 5 is a schematic view of a reaction of transferring only one molecule of a glucosamine residue to a non-reducing end of a linear glucan. This drawing also shows that as a result of disproportionation of the glucan, a mixture of saccharides having a variety of degree of polymerization is obtained as in FIG. 1.

A reaction of extending a saccharide chain on a maltooligosaccharide using GlcN-1-P as a substrate was performed by adding a primer (maltotetraose, Glc4), GlcN-1-P and phosphorylase (60 U) to an acetate buffer (200 mmol/l, pH 6.5), and stirring the mixture at 40° C. for 48 hours (FIG. 5). After completion of the reaction, in order to make analysis by MALDI-TOF MS easy, N-acetylation of a crude product was performed. When MALDI-TOF MS measurement of the resulting acetylated product was performed, the presence of N-acetyl-α-glucosaminyl 1,4-maltooligosaccharide (GlcNAc-Glcn) having an N-acetylglucosamine residue on a non-reducing end of a maltooligosaccharide was confirmed, and proceedings of a glucosaminylation reaction on a maltooligosaccharide was suggested.

Further, a reaction of hydrolyzing the remaining maltooligosaccharide was performed using gluco-amylase (EC 3.2.1.3), and the main product was isolated by HPLC. When its structure was confirmed by 1H NMR and MALDI-TOF MS spectrum, it was found that the structure was N-acetyl-α-glucosaminyl 1,4-maltotetraose. In addition, when a reaction was performed using GlcNF-1-P, GlcNAc-1-P and GlcA-1-P as a substrate, it was made clear that GlcNF-1-P and GlcA-1-P are recognized as a substrate by phosphorylase, and an oligosaccharide in which a corresponding monosaccharide unit has been transferred to a non-reducing end is obtained.

(2.7) Uronic Acid-Containing Glucan and Modified Product and Conjugate Thereof

By further binding the uronic acid-containing glucan and a modified product thereof of the present invention with a medically effective ingredient at a carboxyl residue of a uronic acid residue, a conjugate can be obtained. A substance in which the uronic acid-containing glucan and the medically effective ingredient are bound is referred to as a "uronic acid-containing glucan-medically effective ingredient conjugate", and a substance in which a modified product of the uronic acid-containing glucan and the medically effective ingredient are bound is referred to as a "uronic acid-containing glucan modified product-medically effective ingredient conjugate". Similarly, in the case where uronic acid is glucuronic acid, a substance in which the glucuronic acid-containing glucan and the medically effective ingredient are bound is referred to as a "glucuronic acid-containing glucan-medically effective ingredient conjugate" and a substance in which a modified product of the glucuronic acid-containing glucan and the medically effective ingredient are bound is referred to as a "glucuronic acid-containing glucan modified product-medically effective ingredient conjugate".

The uronic acid-containing glucan modified product can be a hydroxyl group-modified product, a non-reducing end-modified product or a reducing end-modified product.

The hydroxyl group-modified product is as described above.

The non-reducing end-modified product will be explained. When a glucan moiety of the uronic acid-containing glucan or a modified product thereof is a branched α-1,4-glucan, and there is a non-reducing end to which a uronic acid residue is not bound, other substances can be bound to a non-reducing end to which a uronic acid residue is not bound. In a preferable embodiment, a targeting molecule is bound to a non-reducing end in which a uronic acid residue is not bound. In the present specification, the term "targeting molecule" refers to a molecule having tissue targeting function. Examples of a targeting molecule include mannose, galactose, glucosamine, xylose, fucose, galactosamine, an antibody, an antibody fragment, a receptor, a receptor fragment and a receptor ligand. Particularly, since galactose is recognized by an asialoglycoprotein receptor present on a surface of a hepatic parenchymal cell, it is effective. In addition, since mannose is recognized by a mannose receptor expressed on a variety of macrophages including a Kupffer cell and a sinusoid vascular endothelial cell of liver, it is effective. Mannose and galactose can be bound to a non-reducing end of the uronic acid-containing glucan or a modified product thereof, for example, by allowing α-glucan phosphorylase to act to mannose-1-phosphate or galactose-1-phosphate as a substrate. When bound by an enzymatic reaction, mannose and galactose are bound at the position 4 of a non-reducing terminal glucose residue to which a uronic acid residue is not bound.

The reducing end-modified product will be explained. The "reducing end-modified product of the glucuronic acid-containing glucan" refers to a substance in which another substance is bound to a reducing end present in the glucuronic acid-containing glucan of the present invention. In a preferable embodiment, as a method of binding with a different substance at a reducing end, there are the following two methods. The first method is a method of binding a reducing end of a maltooligosaccharide having a degree of polymerization of 2 or more, more preferably a degree of polymerization of 3 or more, further preferably a degree of polymerization of 4 or more to another substance by a known enzymatic procedure or a known chemical procedure and, thereafter, binding glucuronic acid to a non-reducing end of the maltooligosaccharide using the method of the present invention. The second method is a method of binding a reducing end of the glucuronic acid-containing glucan of the present invention to another substance by a known enzymatic procedure.

A method of enzymatically binding a maltooligosaccharide to a different substance in the first method is disclosed, for example, in Japanese Laid-Open Publication No. 5-276883, Japanese Laid-Open Publication No. 07-241181 and International Publication No. WO 01/073106.

The method of enzymatically binding a maltooligosaccharide to a different substance in the first method can be used for substances having an amine group. For example, as a method of chemically binding maltopentaose and a substance having an amine group, there are the following three kinds of methods:

(A) A method of binding reducing terminal aldehyde of maltopentaose and a substance having an amine group by reductive amination;
(B) A method of oxidizing reducing terminal aldehyde of maltopentaose into maltotetraosyl gluconic acid and, thereafter, dehydration-condensing this with a substance having an amine group with a condensing agent; and
(C) A method of oxidizing reducing terminal aldehyde of maltopentaose into maltotetraosyl gluconic acid and, thereafter, dehydrating this to prepare maltotetraosyl gluconolactone, and heating this and a substance having an amine group under an anhydrous solvent condition to allow binding. The three kinds of methods (A), (B) and (C) are described in detail in Japanese Patent Application No. 2008-121693.

An enzyme utilizable in the second method that is a method of binding a reducing end of the glucuronic acid-containing glucan of the present invention to a different substance by an enzymatic procedure can be applied only to carbohydrates and glycosides. As the enzyme, a so-called glucan chain transferring enzyme such as a branching enzyme, CGTase, a D enzyme, amylomaltase or the like is used. These enzymes cut an α-1,4 bond in the glucuronic acid-containing glucan, and transfer a fragment on its non-reducing end side (glucuronic acid-containing fragment) to a receptor molecule (herein, a carbohydrate or a glycoside).

Examples of a substance to be bound include monosaccharides, non-reducing carbohydrates, biocompatible macromolecules, liposome constituent components, glycosides, and amine group-containing low-molecular weight substances.

Examples of monosaccharides include monosaccharides having a functional group, such as glucosamine, N-acetylglucosamine, gluconic acid and the like. Examples of non-reducing carbohydrates include sorbitol, sucrose, trehalose, cyclodextrin, cyclic dextrin, and cyclic amylose. Examples of biocompatible macromolecules include starches, cellulose, chitin, chitosan, dextran, proteins and peptides. Examples of liposome constituent components include phospholipids, fatty acids and surfactants. Examples of glycosides include ascorbic acid glucoside, hydroquinone glucoside, hesperidin glucoside, rutin glucoside, para-nitrophenyl maltopentaose, dodecylmaltose, flavonoid glycosides, terpene glycosides, phenol glycosides, chalcone glycosides and steroid glycosides. Examples of the amine group-containing low-molecular weight substances include various amino acids and dodecylamine.

An embodiment in which a different substance is bound to a carboxyl residue of a uronic acid residue of the uronic acid-containing glucan or a modified product thereof will be described in detail in the following "3".

(3. Utilization of Uronic Acid-Containing Glucan and Modified Product Thereof)

Since in the uronic acid-containing glucan and a modified product thereof of the present invention, a uronic acid residue is bound to a non-reducing end, they have a carboxyl group on a non-reducing end and, as a result, can negatively charge the glucan. For example, the uronic acid-containing branched glucan and a modified product thereof of the present invention in which a number of uronic acids are bound to non-reducing ends of the branched glucan, can generate a state where a carboxyl group of uronic acid on a non-reducing end is dissociated and a state where the carboxyl group is not dissociated, by changing the pH of a solvent. It is thought that, in the state where a carboxyl group of a uronic acid residue on a non-reducing end is dissociated, the uronic acid-containing branched glucan, a modified product thereof and a conjugate thereof come to have an extended out structure by electrostatic repulsion and, in the state where the carboxyl group is not dissociated, the uronic acid-containing branched glucan and a modified product thereof come into a shrunk state. Such a pH dependent change in conformation of a branched polysaccharide microgel can be utilized for medicament delivery.

The uronic acid-containing glucan and a modified product thereof of the present invention have a carboxyl group on a non-reducing end, and a cation can be chelated on this carboxyl group. When a divalent cation such as calcium is further added to a solution containing the uronic acid-containing glucan or a modified product thereof of the present invention, crosslinking formation via calcium occurs, and a microgel and a macrogel of the uronic acid-containing glucan and a modified product thereof can be obtained. Such a microgel and macrogel of the uronic acid-containing glucan and a modified product thereof can be utilized in a wide range of industrial fields such as cosmetics, medicaments, foods and daily articles.

The uronic acid-containing glucan and a modified product thereof of the present invention have a carboxyl group, which is a reactive group, on a non-reducing end. For this reason, via this carboxyl group, a glucan chain can be bound to a different substance (for example, a medically effective ingredient) directly or indirectly via a suitable spacer. As a result, physical properties of the substance can be altered, and a function can be imparted to the substance. A different substance referred to herein may be any of a low-molecular weight organic compound, a high-molecular weight organic compound, a finely particulate carrier for a DDS (a macromolecule micelle, virus particles, a liposome or the like), and an inorganic substance (for example, magnetic microparticles) may be used. The different substance is preferably a medically effective ingredient. For example, the uronic acid-containing glucan and a modified product thereof of the present invention can be easily bound to a substance having an amino group, by reacting with the substance having an amino group, in the presence of a suitable condensing agent such as carbodiimide. When the substance having an amino group is a medically effective ingredient having an amino group such as a peptide or a protein, the resulting compound is a conjugate in which the uronic acid-containing glucan or a modified product thereof and the medically effective ingredient are directly bound. Alternatively, the medically effective ingredient can be bound to the uronic acid-containing glucan or a modified product thereof via a spacer. In this case, a compound having a functional group which can be utilized in binding of an amine group and the medically effective ingredient can be bound to a carboxyl group of the uronic acid-containing glucan or a modified product thereof. Binding of a different compound to a carboxyl group for binding with the medically effective ingredient or the like is referred to as "modification of a carboxyl group". As the effect of altering physical properties by impartation of a glucan chain, improvement in water solubility, impartation of bioaffinity due to formation of a hydration layer and the like can be expected.

For modifying a carboxyl group, a modifying reagent having an amino group (i.e. a primary amine group) or a secondary amine group and a different functional group can be used. In the present specification, a substance having an amine group which is used for modifying a carboxyl group of the glucuronic acid-containing glucan and a modified product of the glucuronic acid-containing glucan is also referred to as a "carboxyl group modifying reagent". The carboxyl group modifying reagent has at least one amine group and at least one different function group. Examples of this functional group include a cationic functional group, an anionic functional group, a hydrophobic group, a maleimide group, a thiol group and an aldehyde group. Examples of the cationic functional group include an amino group, a dimethylamino group, a diethylamino group, a trimethylamino group, an ammonium group, and a pyridinium group. Examples of the modifying reagent having a cationic functional group include ethylenediamine, diethylenetriamine, dimethylaminoethylamine, diethylaminoethylamine, and N,N-dimethyl-4-aminopyridine. Examples of the anionic functional group include a phosphoric acid group, a sulfonic acid group, and a sulfuric acid group. Examples of the modifying reagent having an anionic functional group include 4-amino-3,5-dichlorobenzoic acid, O-phosphoethanolamine, and aminoethylsulfonic acid. Examples of the hydrophobic group include alkyl groups such as a stearyl group, a palmityl group, a methyl group, a propyl group, and a butyl group, and aryl groups such as a phenyl group, a benzyl group, and a tolyl group. Examples of the modifying reagent having a hydrophobic group include stearylamine, methylamine, benzylamine, isobutylamine, and 2,4,6-trimethylanililne. Examples of the modifying reagent having a maleimide group include N-(4-aminophenyl)maleimide. The thiol group is also called mercapto group. Examples of the modifying reagent having a thiol group include mercaptoamine and mercaptoethylamine. Examples of the aldehyde group include a saturated acyclic aldehyde group, an unsaturated acyclic aldehyde group, a saturated alicyclic aldehyde group, and an aromatic aldehyde group. Examples of the modifying reagent having an aldehyde group include 2-amino-3,5-dibromobenzaldehyde, and 4-dimethylaminobenzaldehyde. The carboxyl group modifying reagent can also be selected from the group consisting of N-hydroxysuccinimide, N,N-disuccinimide carbonate, 1-hydroxybenzotriazole, N-hydroxy-5-norbornene-2,3-dicarboxyimide, N-hydroxyphthalimide, isobutyl chloroformate and 4-hydroxyphenyldimethylsulfonium methylsulfate. When these reagents are used, succinimidyl ester is formed between a carboxyl group and a carboxyl group modifying reagent. By modifying a carboxyl group as described above, a spacer moiety for binding the uronic acid-containing glucan and a modified product thereof of the present invention to another molecule can be formed.

For example, in the case where the substance having an amino group is chitosan, it becomes possible to graft (i.e. bind) many uronic acid-containing glucans of the present invention to a main chain of chitosan, and thereby, the physical properties of chitosan can be greatly changed. In this case, a conjugate of the uronic acid-containing glucan or a modified product thereof and chitosan is formed. In this conjugate, the uronic acid-containing glucan or a modified product thereof and chitosan are directly bound.

In addition, when the substance having an amino group is a phospholipid, a phospholipid to which the uronic acid-containing glucan or a modified product thereof of the present invention is bound can be obtained. Such a phospholipid is also referred to as a conjugate of a uronic acid-containing glucan or a modified product thereof and a phospholipid. In this conjugate, the uronic acid-containing glucan or a modified product thereof and a phospholipid are directly bound. By producing a liposome using such a glucan-bound phospholipid, a glucan chain-bound liposome which can be utilized in delivery of medicaments can be easily obtained.

When the substance having an amino group is a proteinaceous medically effective ingredient such as a protein or a peptide, the proteinaceous medically effective ingredient such as a protein or a peptide to which a glucan chain is bound can be obtained. Such a protein or peptide is also referred to as a conjugate of a uronic acid-containing glucan or a modified product thereof and a protein or a peptide. In this conjugate, the uronic acid-containing glucan or a modified product thereof and a protein or a peptide are directly bound. This technique can be utilized in improving the pharmacokinetics of a proteinaceous medically effective ingredient (medicament).

When the substance having an amino group is a magnetic microparticle, a magnetic microparticle with a glucan chain bound thereto can be obtained, and this can be utilized as a contrast agent for clinical diagnosis. In this case, a conjugate of the uronic acid-containing glucan or a modified product thereof and the magnetic microparticle is formed. In this conjugate, the uronic acid-containing glucan or a modified product thereof and the magnetic microparticle are directly bound.

When the substance having an amino group is a metal ligand (chelating agent), a metal ligand with a glucan chain bound thereto can be obtained, and this can be utilized as a contrast agent for clinical diagnosis by coordination with a radioactive metal element. In this case, a conjugate of the uronic acid-containing glucan or a modified product thereof and the metal ligand is formed. In this conjugate, the uronic acid-containing glucan or a modified product thereof and the metal ligand are directly bound.

The glucuronic acid-containing glucan of the present invention has a carboxyl group, which is a reactive group, on a non-reducing end. The carboxyl group is charged negatively under a neutral condition. On the other hand, by chemically modifying this carboxyl group, a cationic functional group or a hydrophobic group can be introduced into an end of the glucan. On the other hand, glucans having a variety of structures and molecular weights can be utilized in a glucan moiety of the present invention. When these techniques are combined, for example, an anionic functional group, a cationic functional group, a hydrophobic group and the like can be controllably introduced into a terminus of a branched glucan having a molecular weight to such an extent that a protein can be enclosed. An end of such a modified glucan can be flexibly transferred, performs electrostatic interaction with a charged part present on a protein surface, and performs hydrophobic interaction with a hydrophobic region and, as a result, the glucan of the present invention forms a complex via a non-covalent bond with a protein. Therefore, by mixing the uronic acid-containing glucan or a modified product thereof of the present invention and a protein, a peptide or the like in a solution, a complex of the uronic acid-containing glucan or a modified product thereof of the present invention and a protein, a peptide, or the like can be formed. Similarly, the terminal structure of the glucan which can effectively form a non-covalently bound complex with a nucleic acid, a liposome, a virus particle, a macromolecule micelle, or a low-molecular weight compound can also be designed. As described above, the glucan and an terminal derivative thereof of the present invention can effectively form a complex with a protein, a nucleic acid, a low-molecular weight compound, or a finely particulate carrier for a DDS (for example, a liposome, a macromolecule micelle, or virus particles), and can influence on stability, physical properties, absorbability, pharmacokinetics (for example, organ accumulating property, tissue targeting property, or blood retention property) and the like of them. As described above, the glucan of the present invention can be effectively utilized as a DDS carrier of the medically effective ingredient of medicaments or as an agent for modifying a finely particulate carrier for a DDS.

When the uronic acid-containing glucan of the present invention is utilized as the modifying material of the medically effective ingredient of medicaments, it is necessary to control degradation of the modifying material in a body. When the glucan is a linear α-1,4-glucan, it undergoes rapid degradation with α-amylase, and the time of existence in a body may be too short. In such a case, there is a possibility that an object as the modifying material cannot be attained. Then, by modifying some or all of hydroxyl groups of glucose constituting a glucan, the necessary time for degradation can be controlled. A hydroxyl group-modified product of such a uronic acid-containing glucan is preferable in the present invention. Modification is etherification or esterification. Etherification is preferably etherification with alkyl halide or an alcohol. The number of carbon atoms of alkyl halide or an alcohol used in etherification is preferably 1 to 10, more preferably 1 to 5, further preferably 1 to 3. The halogen group can be preferably fluoro, chloro, bromo or iodo. Esterification is preferably esterification with carboxylic acid or acyl halide. The number of carbon atoms of carboxylic acid or acyl halide used in esterification is preferably 1 to 10, more preferably 1 to 5. Modification is desirably esterification. Esterification is more preferably acylation, further preferably acetylation.

As described above, the uronic acid-containing glucan and a modified product thereof and a conjugate thereof of the present invention (preferably, a glucuronic acid-containing glucan and a modified product thereof and a conjugate thereof) can be freely designed for their structure of the glucan and the structure of its non-reducing end and, by utilizing this, the pharmacokinetics of the medically effective ingredient of medicaments can be arbitrary controlled. This is the modifying material of the medically effective ingredient of medicaments, which has a structure completely degradable in a body, and can be safely utilized without anxiety for toxicity due to accumulation.

Therefore, according to the present invention, a medicament containing the uronic acid-containing glucan or a modified product thereof of the present invention (preferably, a glucuronic acid-containing glucan and a modified product thereof) and the medically effective ingredient is provided. In the medicament of the present invention, the medically effective ingredient is preferably selected from the group consisting of a low-molecular weight organic compound, a protein, a peptide, an antibody, an antibody fragment, a receptor, a receptor fragment, a DNA, an RNA, a siRNA and an RNA aptamer.

According to a particular embodiment of the present invention, there is provided a conjugate of a medically effective ingredient and the glucuronic acid-containing glucan, a hydroxyl group-modified product thereof, a reducing end-modified product thereof, or a carboxylic acid group-modified product thereof of the present invention, wherein the medically effective ingredient is covalently bound with at least one of carboxyl groups of the glucuronic acid residue directly, or is bound with at least one of carboxyl groups of the glucuronic acid residue via a spacer. The medically effective ingredient is preferably selected from the group consisting of a low-molecular weight organic compound, a protein, a peptide, an antibody, an antibody fragment, a receptor, a receptor fragment, a DNA, an RNA, a siRNA and an RNA aptamer.

According to a particular embodiment, the present invention provides a composition for clinical diagnosis, containing the uronic acid-containing glucan, a hydroxyl group-modified product thereof, a reducing end-modified product thereof, or a carboxylic acid group-modified product of the present invention thereof (preferably, a glucuronic acid-containing glucan, a hydroxyl group-modified product thereof, a reducing end-modified product thereof, or a carboxylic acid group-modified product thereof).

According to a particular embodiment, the present invention provides a finely particulate carrier for a DDS, containing the uronic acid-containing glucan, a hydroxyl group-modified product thereof, a reducing end-modified product thereof, or a carboxylic acid group-modified product thereof of the present invention (preferably, a glucuronic acid-containing glucan, a hydroxyl group-modified product thereof, a reducing end-modified product thereof, or a carboxylic acid group-modified product thereof). This finely particulate carrier for a DDS is preferably selected from the group consisting of a liposome, a virus particle, a macromolecule micelle and a nanogel composed of macromolecule bearing hydrophobic groups.

According to a particular embodiment, the present invention provides a finely particulate carrier for a DDS, containing the uronic acid-containing glucan, a hydroxyl group-modified product thereof, a reducing end-modified product thereof, or a carboxylic acid group-modified product thereof of the present invention (preferably, a glucuronic acid-containing glucan, a hydroxyl group-modified product thereof, a reducing end-modified product thereof, or a carboxylic acid group-modified product thereof).

(4. Uronic Acid-Containing Glucan and Modified Product Thereof and Conjugate Thereof of the Present Invention)

The uronic acid-containing glucan of the present invention is preferably a glucuronic acid-containing glucan. In the present specification, a glucan in which a uronic acid residue is bound to at least one non-reducing end of a glucan, but there is no uronic acid residue at the positions other than the non-reducing end is referred to as a "uronic acid-containing glucan". In the present specification, a glucan in which a glucuronic acid residue is bound to at least one non-reducing end of a glucan, but there is no glucuronic acid residue at the positions other than the non-reducing end is referred to as a "uronic acid-containing glucan".

The glucuronic acid-containing glucan of the present invention is a glucuronic acid-containing glucan in which a glucuronic acid residue is bound to at least one non-reducing end of a glucan, but there is no glucuronic acid residue at the positions other than the non-reducing end, wherein the glucan is a branched α-1,4 glucan or a linear α-1,4 glucan.

When a glucan moiety of the glucuronic acid-containing glucan is a linear glucan, since the number of non-reducing end is one, one glucuronic acid residue is bound to the non-reducing end. When a glucan moiety of the glucuronic acid-containing glucan is a branched glucan, since there are two or more non-reducing ends, a glucuronic acid residue is bound to one or more non-reducing ends of them. In the glucuronic acid-containing glucan of the present invention, there is no glucuronic acid residue at the positions other than a non-reducing end. Absence of the glucuronic acid residue at the positions other than a non-reducing end can be confirmed, for example, by treating the glucuronic acid-containing glucan with α-amylase and isoamylase. α-Amylase acts on an α-1,4 glucan to generate maltose and glucose, and a glucuronidated α-1,4 glucan chain exhibits resistance to α-amylase. The glucan containing the glucuronic acid residue only on a non-reducing end generates glucuronosyl maltose, maltose and glucose by treatment with α-amylase and isoamylase. On the other hand, the glucan containing a glucuronic acid residue also on a position other than a non-reducing end generates saccharides other than glucuronosyl maltose, maltose and glucose by treatment with α-amylase and isoamylase. This method can confirm that the glucuronic acid residue is not bound to a position other than a non-reducing end.

(4.1) Branched Glucan with Glucuronic Acid Residue Bound Thereto, Modified Product Thereof and Conjugate Thereof When a glucan moiety contained in the glucuronic acid-containing glucan of the present invention is a branched α-1,4 glucan, in the glucuronic acid-containing glucan, a glucuronic acid residue is bound to at least one of a plurality of non-reducing ends possessed by this branched α-1,4 glucan. According to the present invention, a modified product of the branched glucan with a glucuronic acid residue bound thereto is also provided. According to the present invention, a conjugate of the branched glucan with a glucuronic acid residue bound thereto or a modified product thereof is also provided. Modification of the modified product is as described above in detail. The substance to be bound in a conjugate is as described above in detail.

A branched glucan moiety contained in the glucuronic acid-containing branched glucan, a modified product thereof and a conjugate thereof of the present invention is preferably selected from the group consisting of a branched maltooligosaccharide, a starch, amylopectin, glycogen, dextrin, an enzymatically synthesized branched glucan and highly branched cyclic dextrin. A preferable range of these branched glucan moieties is as explained in "(1.1) Glucans and modified products of glucan".

The molecular weight of the glucuronic acid-containing branched glucan of the present invention is preferably about 1,000 or more, more preferably about 3,000 or more, and further preferably about 5,000 or more. The molecular weight of the glucuronic acid-containing branched glucan of the present invention is preferably about $1\times10^9$ or less, more preferably about $3\times10^8$ or less, and further preferably about $1\times10^8$ or less.

The molecular weight of the modified product of the glucuronic acid-containing branched glucan of the present invention is preferably about 1,000 or more, more preferably about 3,000 or more, and further preferably about 5,000 or more. The molecular weight of the modified product of the glucuronic acid-containing branched glucan of the present invention is preferably about $1\times10^9$ or less, more preferably about $3\times10^8$ or less, and further preferably about $1\times10^8$ or less.

In the conjugate of the present invention, it is preferable that another substance (for example, targeting molecule, medically effective ingredient, or the like) is bound to the aforementioned glucuronic acid-containing branched glucan having a suitable molecular weight.

In the present invention, the glucuronic acid-containing branched glucan modified product is preferable. Modification is preferably acylation or etherification, and more preferably acetylation. The acylation degree is preferably about 0.1 or more, further preferably about 0.2 or more, and particularly preferably about 0.3 or more. The acylation degree is calculated by quantification of acetic acid released by heating under an alkali condition. The etherification degree is preferably about 0.1 or more, further preferably about 0.2 or more, and particularly preferably about 0.3 or more. The etherification degree is calculated by NMR.

The number of glucuronic acid residues bound to the glucuronic acid-containing branched glucan, a modified product thereof and a conjugate thereof of the present invention is preferably 1 or more, more preferably 2 or more, and further preferably 3 or more, per one molecule. The number of glucuronic acid residues bound to the glucuronic acid-containing branched glucan or a modified product thereof of the present invention is not limited to them, and for example, may be 5 or more, 10 or more, 15 or more, 20 or more, 50 or more, or 100 or more, per one molecule. The number can be suitably adjusted according to the purpose. The upper limit of the number of glucuronic acid residues bound to the glucuronic acid-containing branched glucan or a modified product thereof of the present invention is the number of non-reducing ends of the branched glucan moiety. The number of glucuronic acid residues bound to the glucuronic acid-containing branched glucan or a modified product thereof of the present invention can be, for example, about 1,000 or less, about 800 or less, about 700 or less, about 600 or less, about 500 or less, about 400 or less, about 300 or less, about 200 or less, about 100 or less, about 50 or less, or the like, per one molecule.

In a particular embodiment, the number of glucuronic acid residues bound to the glucuronic acid-containing branched glucan, a modified product thereof and a conjugate thereof of the present invention is preferably about 10% or more, more preferably about 20% or more, particularly preferably about 30% or more and, for example, can be about 40% or more, about 50% or more or about 60% or more of the number of non-reducing ends possessed by the branched glucan moiety. In a particular embodiment, the number of glucuronic acid residues bound to the glucuronic acid-containing branched glucan, a modified product thereof and a conjugate thereof of the present invention is preferably about 100% or less, more preferably about 90% or less, particularly preferably about 80% or less and, for example, can be about 70% or less, about 60% or less, or about 50% or less of the number of non-reducing ends possessed by the branched glucan moiety.

(4.2) Linear Glucan with Glucuronic Acid Residue Bound Thereto, Modified Product Thereof and Conjugate Thereof In the glucuronic acid-containing linear glucan of the present invention, a glucuronic acid residue is bound to a non-reducing end of the linear glucan moiety. Since the linear glucan has only one non-reducing end, the glucuronic acid-containing linear glucan of the present invention contains only one glucuronic acid residue. According to the preset invention, there is also provided a modified product of the linear glucan with a glucuronic acid residue bound thereto. According to the present invention, there is also provided a conjugate of the linear glucan with a glucuronic acid residue bound thereto or a modified product thereof. Modification of the modified product is as described above in detail. The substance to be bound in a conjugate is as described above in detail.

The linear glucan moiety contained in the glucuronic acid-containing linear glucan or a modified product thereof of the present invention is preferably selected from the group consisting of a maltooligosaccharide, amylose (for example, natural amylose or enzymatically synthesized amylose) and a derivative thereof. A preferable range of these linear glucan moieties is as explained in "(1.1) Glucans and modified products of glucan".

The molecular weight of the glucuronic acid-containing linear glucan of the present invention is preferably about 450 or more, more preferably about 600 or more, and further preferably about 1,000 or more. The molecular weight of the glucuronic acid-containing linear glucan of the present invention is preferably about 200,000 or less, more preferably about 150,000 or less, and further preferably about 100,000 or less.

The molecular weight of a modified product of the glucuronic acid-containing linear glucan of the present invention is preferably about 450 or more, more preferably about 600 or more, and further preferably about 1,000 or more. The molecular weight of the modified product of the glucuronic acid-containing linear glucan of the present invention is preferably about 200,000 or less, more preferably about 150,000 or less, and further preferably about 100,000 or less.

In the conjugate of the present invention, it is preferable that another substance (for example, targeting molecule, medically effective ingredient, or the like) is bound to the glucuronic acid-containing linear glucan having such a suitable molecular weight as mentioned before.

In the present invention, a modified product of the glucuronic acid-containing linear glucan is preferable. Modification is preferably acylation or etherification, more preferably acetylation. The acylation degree is preferably about 0.1 or more, further preferably about 0.2 or more, and particularly preferably about 0.3 or more. The acylation degree is calculated by quantification of acetic acid released by heating under an alkali condition. The etherification degree is preferably about 0.1 or more, further preferably about 0.2 or more, and particularly preferably about 0.3 or more. The etherification degree is calculated by NMR.

The glucuronic acid-containing linear glucan of the present invention can be represented, for example, by the following formula 1:

[Chemical formula 16]

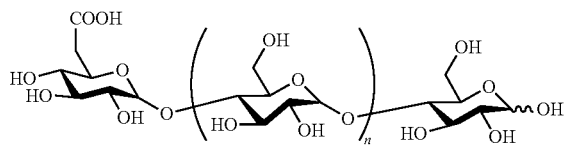

Formula 1 wherein n is an integer of 1 or more. n is preferably about 1 or more, more preferably about 2 or more, and further preferably about 3 or more. n is preferably about 1200 or less, more preferably about 900 or less, and further preferably about 600 or less.

The glucuronic acid-containing linear glucan and the reducing end-modified product thereof of the present invention can be represented, for example, by the following formula 2:

[Chemical formula 17]

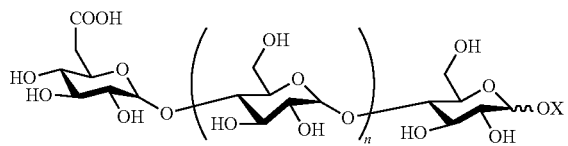

Formula 2 wherein n is an integer of 1 or more. n is preferably about 1 or more, more preferably about 2 or more, and further preferably about 3 or more. n is preferably about 1200 or less, more preferably about 900 or less, and further preferably about 600 or less. X is selected from the group consisting of hydrogen, monosaccharides, non-reducing carbohydrates, biocompatible macromolecules, liposome constituent components, glycosides, and amine group-containing low-molecular weight substances. X is preferably hydrogen, glucosamine, N-acetylglucosamine, gluconic acid, sorbitol, sucrose, trehalose, cyclodextrin, cyclic dextrin, cyclic amylose, starches, cellulose, chitin, chitosan, dextran, proteins, peptides, phospholipids, fatty acids, surfactants, ascorbic acid glucosides, hydroquinone glucosides, hesperidin glucosides, rutin glucosides, para-nitrophenyl maltopentaose, dodecylmaltose, flavonoid glycosides, terpene glycosides, phenol glycosides, chalcone glycosides, steroid glycosides, amino acids and dodecylamine. When X is hydrogen, this molecule is a glucuronic acid-containing linear glucan; when X is a substance other than hydrogen, this molecule is a reducing end-modified product of a glucuronic acid-containing linear glucan.

The glucuronic acid-containing linear glucan, hydroxyl group-modified product of a glucuronic acid-containing linear glucan, and the reducing end-modified product thereof of the present invention can be represented, for example, by the following formula 3:

[Chemical formula 18]

Formula 3

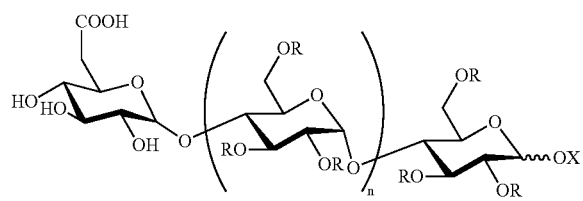

wherein n is an integer of 1 or more. n is preferably about 1 or more, more preferably about 2 or more, and further preferably about 3 or more. n is preferably about 1200 or less, more preferably about 900 or less, and further preferably about 600 or less. X is preferably selected from the group consisting of hydrogen, monosaccharides, non-reducing carbohydrates, biocompatible macromolecules, liposome constituent components, glycosides, and amine group-containing low-molecular weight substances. X is preferably hydrogen, glucosamine, N-acetylglucosamine, gluconic acid, sorbitol, sucrose, trehalose, cyclodextrin, cyclic dextrin, cyclic amylose, starches, cellulose, chitin, chitosan, dextran, proteins, peptides, phospholipids, fatty acids, surfactants, ascorbic acid glucosides, hydroquinone glucosides, hesperidin glucosides, rutin glucosides, para-nitrophenyl maltopentaose, dodecylmaltose, flavonoid glycosides, terpene glycosides, phenol glycosides, chalcone glycosides, steroid glycosides, amino acids and dodecylamine. Wherein R is preferably independently selected from the group consisting of hydrogen, hydroxyalkyl group, an alkyl group, an acetyl group, a carboxymethyl group, a sulfuric acid group and a phosphoric acid group. When X and all of R are hydrogen, this molecule is a glucuronic acid-containing linear glucan; when X is hydrogen, and R is each independently hydrogen or another group, provided that at least one of R is a group other than hydrogen, this molecule is a hydroxyl group-modified product of a glucuronic acid-containing linear glucan; when X is a substance other than hydrogen, and all R is hydrogen, this molecule is a reducing end-modified product of a glucuronic acid-containing linear glucan; when X is a substance other than hydrogen, and each R is independently hydrogen or another group, provided that at least one of R is a group other than hydrogen, this molecule is a reducing end-modified product of a hydroxyl group-modified product of a glucuronic acid-containing linear glucan.

The glucuronic acid-containing linear glucan, hydroxyl group-modified product of a glucuronic acid-containing linear glucan, and the reducing end-modified product thereof and the carboxyl group-modified product thereof of the present invention can be represented, for example, by the following formula 4:

[Chemical formula 19]

Formula 4

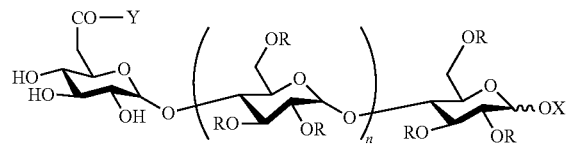

Wherein n is an integer of 1 or more. n is preferably about 1 or more, more preferably about 2 or more, and further preferably about 3 or more. n is preferably about 1200 or less, more preferably about 900 or less, and further preferably about 600 or less. X is selected from the group consisting of hydrogen, monosaccharides, non-reducing carbohydrates, biocompatible macromolecules, liposome constituent components, glycosides, and amine group-containing low-molecular weight substances. X is preferably hydrogen, glucosamine, N-acetylglucosamine, gluconic acid, sorbitol, sucrose, trehalose, cyclodextrin, cyclic dextrin, cyclic amylose, starches, cellulose, chitin, chitosan, dextran, proteins, peptides, phospholipids, fatty acids, surfactants, ascorbic acid glucosides, hydroquinone glucosides, hesperidin glucosides, rutin glucosides, para-nitrophenyl maltopentaose, dodecylmaltose, flavonoid glycosides, terpene glycosides, phenol glycosides, chalcone glycosides, steroid glycosides, amino acids and dodecylamine. Wherein R is preferably independently selected from the group consisting of hydrogen, hydroxyalkyl group, an alkyl group, an acetyl group, a carboxymethyl group, a sulfuric acid group and a phosphoric acid group. Wherein, Y is preferably selected from the group consisting of hydroxyl group, a cationic substituent, a hydrophobic group, a maleimide group and a succinimide group. When X and all of R are hydrogen and Y is hydroxyl group, this molecule is a glucuronic acid-containing linear glucan; when X and all of R are hydrogen and Y is a group other than hydroxyl group, this molecule is a carboxyl group-modified product of glucuronic acid-containing linear glucan; when X is hydrogen and R is each independently hydrogen or another group, provided that at least one of R is a group other than hydrogen and Y is hydroxyl group, this molecule is a hydroxyl group-modified product of a glucuronic acid-containing linear glucan; when X is hydrogen and R is each independently hydrogen or another group, provided that at least one of R is a group other than hydrogen and Y is a group other than hydroxyl group, this molecule is a carboxyl group-modified product of a hydroxyl group-modified product of a glucuronic acid-containing linear glucan; when X is a substance other than hydrogen, all R is hydrogen, and Y is hydroxyl group, this molecule is a reducing end-modified product of a glucuronic acid-containing linear glucan; when X is a substance other than hydrogen, all R is hydrogen, and Y is group other than hydroxyl group, this molecule is a reducing end-modified product of a carboxyl group-modified product of a glucuronic acid-containing linear glucan; when X is a substance other than hydrogen, each R is independently hydrogen or another group, provided that at least one of R is a group other than hydrogen and Y is hydroxyl group, this molecule is a reducing end-modified product of a hydroxyl group-modified product of a glucuronic acid-containing linear glucan; and when X is a substance other than hydrogen, each R is independently hydrogen or another group, provided that at least one of R is a group other than hydrogen and Y is a group other than hydroxyl group, this molecule is a carboxyl group-modified product of hydroxyl group-modified product a glucuronic acid-containing linear glucan.

The glucuronic acid-containing of the present invention can be represented, for example, by the following formula 5:

[Chemical formula 20]

Formula 5

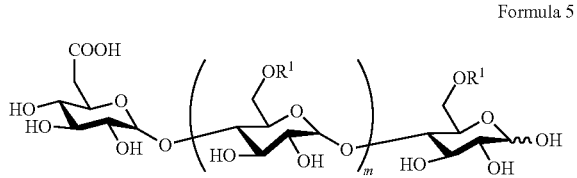

wherein m is an integer of 1 or more. m is preferably about 1 or more, more preferably about 2 or more, and further preferably about 3 or more, and m is preferably about 1200 or less, more preferably about 900 or less, and further preferably about 600 or less. $R^1$ is independently H, a glucan chain having the structure of formula A or a glucan chain having the structure of formula B. When all of $R^1$ is H, the glucan shown by formula 5 is a linear glucan. When at least one of $R^1$ has the structure of formula A or formula B, the glucan shown by formula 5 is a branched glucan.

[Chemical formula 21]

Formula A

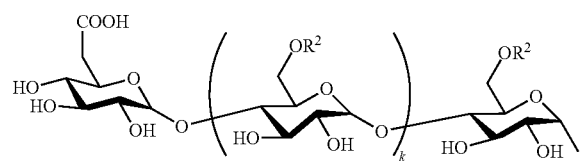

in formula A, k is an integer of 1 or more. k is preferably about 1 or more, more preferably about 2 or more, and further preferably about 3 or more, and k is preferably about 100 or less, more preferably about 25 or less, and further preferably about 20 or less. In formula A, each $R^2$ is independently H, a glucan chain having the structure of formula A or a glucan chain having the structure of formula B.

[Chemical formula 22]

Formula B

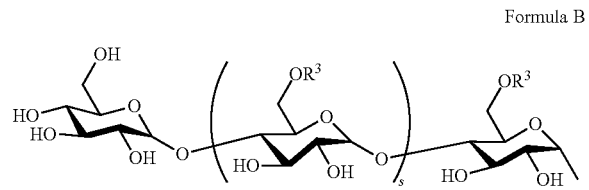

In formula B, s is an integer of 1 or more. s is preferably about 1 or more, more preferably about 2 or more, and further preferably about 3 or more, and s is preferably about 100 or less, more preferably about 25 or less, and further preferably about 20 or less. In formula B, $R^3$ is independently H, a glucan chain having the structure of formula A or a glucan chain having the structure of formula B.

As explained above, in formula 5, $R^1$ can have a structure in which the position of $R^2$ of a group having the structure of formula A or $R^3$ of a group having the structure of formula B is substituted with a group having the structure of formula A or a group having the structure of formula B several times. The total of times of substitutions with formula A and formula B is equal to the number of unit chains of the branched glucan molecule represented by formula 5. The number of unit chain of branched glucan molecule is preferably about 1 or more, more preferably about 10 or more, and further more preferably about 30 or more. The number of unit chain of branched glucan molecule is preferably about 5,000 or less, more preferably about 2,000 or less, and further more preferably about 1,000 or less.

The glucuronic acid-containing glucan or the hydroxyl group-modified product of a glucuronic acid-containing glucan of the present invention can be represented, for example, by the following formula 6:

[Chemical formula 23]

Formula 6

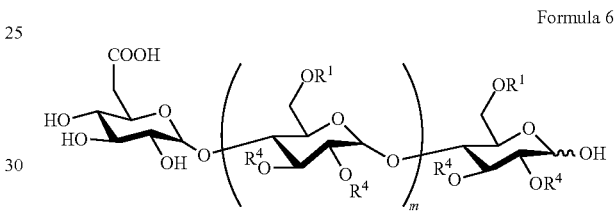

wherein m is an integer of 1 or more. m is preferably about 1 or more, more preferably about 2 or more, and further preferably about 3 or more, and m is preferably about 1200 or less, more preferably about 900 or less, and further preferably about 600 or less. $R^1$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B.

[Chemical formula 24]

Formula 6A

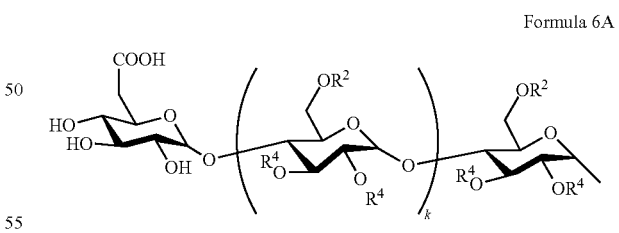

in formula 6A, k is an integer of 1 or more. k is preferably about 1 or more, more preferably about 2 or more, and further preferably about 3 or more, and k is preferably about 100 or less, more preferably about 25 or less, and further preferably about 20 or less. In formula 6A, each $R^2$ is independently H, a hydroxyalkyl group, an alkyl group, an acetyl group, a carboxymethyl group, a sulfuric acid group, a phosphoric acid group, a glucan chain having the structure of formula 6A or a glucan chain having the structure of formula 6B.

[Chemical formula 25]

Formula 6B

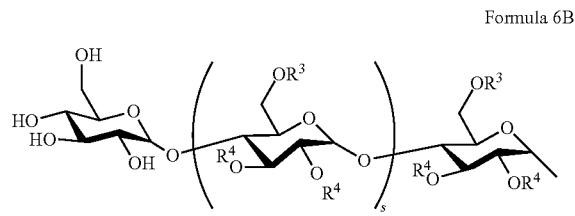

in formula 6B, s is an integer of 1 or more. s is preferably about 1 or more, more preferably about 2 or more, and further preferably about 3 or more, and s is preferably about 100 or less, more preferably about 25 or less, and further preferably about 20 or less. In formula 6A, each $R^3$ is independently H, a hydroxyalkyl group, an alkyl group, an acetyl group, a carboxymethyl group, a sulfuric acid group and a phosphoric acid group, a glucan chain having the structure of formula 6A or a glucan chain having the structure of formula 6B.

In formula 6, formula 6A and formula 6B, each $R^4$ is independently selected from the group consisting of H, a hydroxyalkyl group, an alkyl group, an acetyl group, a carboxymethyl group, a sulfuric acid group and a phosphoric acid group.

The glucuronic acid-containing glucan, a hydroxyl group-modified product of a glucuronic acid-containing glucan and a reducing end-modified product thereof of the present invention can be represented, for example, by the following formula 7:

[Chemical formula 26]

Formula 7

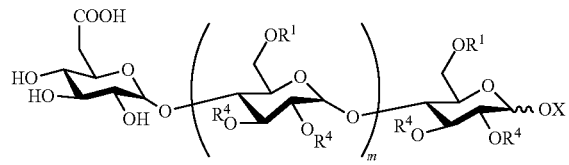

wherein m is an integer of 1 or more. m is preferably about 1 or more, more preferably about 2 or more, and further preferably about 3 or more, and m is preferably about 1200 or less, more preferably about 900 or less, and further preferably about 600 or less. $R^1$ is independently H, a glucan chain having the structure of formula 6A or a glucan chain having the structure of formula 6B. Formula 6A and formula 6B are same with the definition for the aforementioned formula 6.

In formula 7, formula 6A and formula 6B, $R^4$ is independently selected from the group consisting of hydrogen, a hydroxyalkyl group, an alkyl group, an acetyl group, a carboxymethyl group, a sulfuric acid group and a phosphoric acid group, in formula 7, X is preferably independently selected from the group consisting of monosaccharides, non-reducing carbohydrates, biocompatible macromolecules, liposome constituent components, glycosides, and amine group-containing low-molecular weight substances. X is more preferably selected from the group consisting of glucosamine, N-acetylglucosamine, gluconic acid, sorbitol, sucrose, trehalose, cyclodextrin, cyclic dextrin, cyclic amylose, starches, cellulose, chitin, chitosan, dextran, proteins, peptides, phospholipids, fatty acids, surfactants, ascorbic acid glucosides, hydroquinone glucosides, hesperidin glucosides, rutin glucosides, para-nitrophenyl maltopentaose, dodecylmaltose, flavonoid glycosides, terpene glycosides, phenol glycosides, chalcone glycosides, steroid glycosides, amino acids and dodecylamine.

The glucuronic acid-containing glucan, a hydroxyl group-modified product of a glucuronic acid-containing glucan, a reducing end-modified product thereof, or a carboxyl group-modified product thereof of the present invention can be represented, for example, by the following formula 8:

[Chemical formula 27]

Formula 8

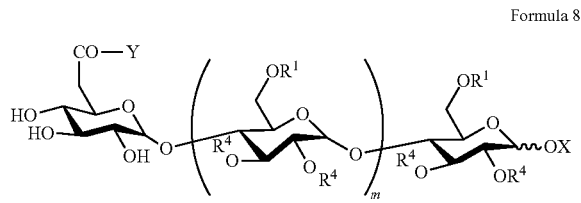

wherein m is an integer of 1 or more. m is preferably about 1 or more, more preferably about 2 or more, and further preferably about 3 or more, and m is preferably about 1200 or less, more preferably about 900 or less, and further preferably about 600 or less. $R^1$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A or a glucan chain having the structure of formula 6B.

[Chemical formula 28]

Formula 6A

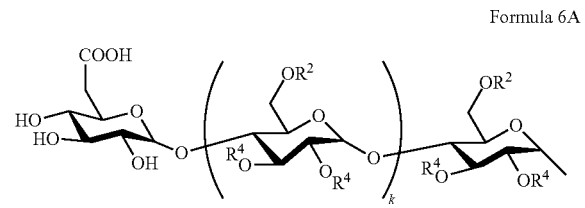

in formula 6A, k is an integer of 1 or more. k is preferably about 1 or more, more preferably about 2 or more, and further preferably about 3 or more, and k is preferably about 100 or less, more preferably about 25 or less, and further preferably about 20 or less. In formula 6A, each $R^2$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A or a glucan chain having the structure of formula 6B.

[Chemical formula 29]

Formula 8A

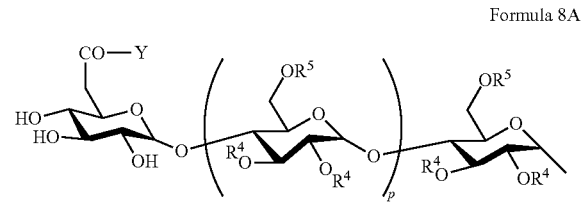

in formula 8A, p is an integer of 1 or more. p is preferably about 1 or more, more preferably about 2 or more, and further preferably about 3 or more, and p is preferably about 100 or less, more preferably about 25 or less, and further preferably about 20 or less. In formula 8A, $R^5$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B:

[Chemical formula 30]

Formula 6B

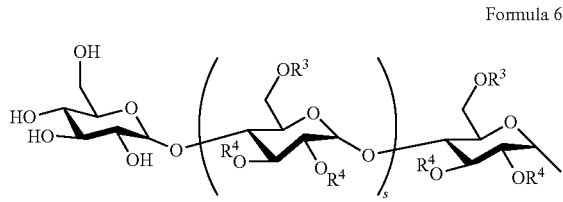

in formula 6B, s is an integer of 1 or more. s is preferably about 1 or more, more preferably about 2 or more, and further preferably about 3 or more, and s is preferably about 100 or less, more preferably about 25 or less, and further preferably about 20 or less. In formula 6B, each $R^3$ is independently H, a hydroxyalkyl group, an alkyl group, an acetyl group, a carboxymethyl group, a sulfuric acid group, a phosphoric acid group, a glucan chain having the structure of formula 6A, a glucan chain having the structure of formula 8A, or a glucan chain having the structure of formula 6B.

In formula 8, formula 6A, formula 8A and formula 6B, $R^4$ is independently selected from the group consisting of hydrogen, a hydroxyalkyl group, an alkyl group, an acetyl group, a carboxymethyl group, a sulfuric acid group and a phosphoric acid group, in formula 8, X is independently selected from the group consisting of monosaccharides, non-reducing carbohydrates, biocompatible macromolecules, liposome constituent components, glycosides, and amine group-containing low-molecular weight substances.

in formula 8 and formula 8A, Y is a substituent introduced for binding with a medically effective ingredient, Y is obtained by a reaction with a carboxyl group modifying reagent, and the carboxyl group modifying reagent has at least one amine group and at least one other functional group.

Examples of modification of the glucuronic acid-containing glucan of the present invention and the purpose of the modification are summarized in the following Table 1. The structure in the table is merely an example.

TABLE 1

Examples of modification and use of glucuronic acid-containing glucan

| Modification site | Specific example and structure | Purpose of modification |
|---|---|---|
| Unmodified | Formula 4 (Y = OH, R = H, X = H) | — |
| Hydroxyl group (R) | Substitution on acetyl group (Y = OH, R = Ac, X = H) | Degradation with α-amylase is suppressed, and blood retention is improved. |

TABLE 1-continued

Examples of modification and use of glucuronic acid-containing glucan

Formula 4

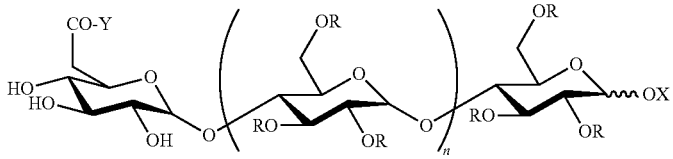

| Modification site | Specific example and structure | Purpose of modification |
|---|---|---|
| Carboxyl group (Y) | Substitution on dimethylaminoethyl group (Y = dimethylaminoethyl group, R = H, X = H) | A positive charge is imparted. Can participate in electrostatic interaction with a medically effective ingredient (for example, a nucleic acid or a protein). Can be utilized in covalent binding with a medically effective ingredient. |
| Carboxyl group (Y) | Substitution on phenyl group (Y = phenyl group, R = H, X = H) | Impartation of hydraphobicity. Can participate in hydrophobic interaction with a medically effective ingredient (for example, a protein or a hydrophobic small molecule). |
| Carboxyl group (Y) | Substitution on maleimide group (Y = maleimide group, R = H, X = H) | Can form selectively a covalent bond with a thiol group in a medically effective ingredient (for example, a protein). |

TABLE 1-continued

Examples of modification and use of glucuronic acid-containing glucan

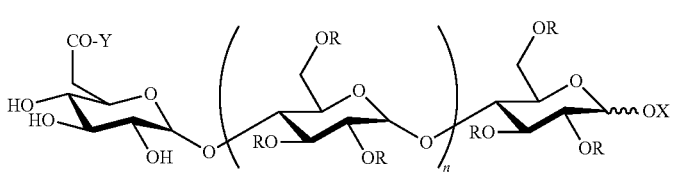

Formula 4

| Modification site | Specific example and structure | Purpose of modification |
|---|---|---|
| Carboxyl group (Y) | Substitution on succinimide group (Y = succinimide group, R = H, X = H) | Can form selectively a covalent bond with an amine group in a medically effective ingredient (for example, a protein). |

EXAMPLES

The present invention will be explained below based on examples, but the present invention is not limited to the examples. α-Glucan phosphorylase derived from *Aquifex aeolicus* VF5 used in the examples is *Aquifex aeolicus* VF5-derived α-glucan phosphorylase prepared by the following Production Example 1.

Production Example 1

Preparation of *Aquifex aeolicus* VF5-Derived α-Glucan Phosphorylase (A) Making of *Aquifex aeolicus* VF5-Derived α-Glucan Phosphorylase Gene A nucleic acid (also referred to as an "α-glucan phosphorylase gene") having a base sequence (base sequence of $491380^{th}$ to $493458^{th}$ of ACCESSION No. AE000657 of GenBank base sequence database) encoding the amino acid sequence for *Aquifex aeolicus* VF5-derived α-glucan phosphorylase gene (the amino acid sequence described in SEQ ID NO:2 of Sequence Listing; the amino acid sequence obtained by translating the base sequence of $491380^{th}$ to $493458^{th}$ of ACCESSION No. AE000657 of GenBank base sequence database of National Center for Biotechnology Information (NCBI) in the USA) was chemically synthesized by a method well-known to those skilled in the art. It is noted that a base sequence of a gene encoding α-glucan phosphorylase derived from *Aquifex aeolicus* VF5 was registered as ACCESSION No. AE000704, $86^{th}$ to $2164^{th}$ at the time of the filing date of the application to which the present application claims the priority, but ACCESSION No. and their positions were changed on Mar. 9, 2010. An NdeI site was created upstream of a translation initiation codon of this α-glucan phosphorylase gene. In addition, a BamHI site was created downstream of a translation stop codon, and this synthetic gene was cut with NdeI and BamHI, and inserted into plasmid pET11c (manufactured by Novagen) which had been previously cut with NdeI and BamHI to make a plasmid pET-AqGP having an *Aquifex aeolicus* VF5-derived α-glucan phosphorylase gene.

(B) Expression of *Aquifex aeolicus* VF5-Derived α-Glucan Phosphorylase Gene in *Escherichia coli*

*Escherichia coli* BL21 (DE3) was transformed with this plasmid pET-AqGP according to a conventional method to obtain a transformant. A liquid containing the transformant was diluted and applied on an ampicillin-containing LB agar medium (100 μg/ml ampicillin, 1% tryptone manufactured by Difco, 0.5% yeast extract manufactured by Difco, 0.5% NaCl, 1.5% agar, pH 7.3) so that independent colonies were obtained, and this was cultured at 37° C. overnight. *Escherichia coli* grown on this ampicillin-containing LB agar medium is a transformant which harbors an introduced plasmid, and can express the introduced plasmid. In such a way, *Escherichia coli* expressing an α-glucan phosphorylase gene was successfully made.

(C) Preparation of *Aquifex aeolicus* VF5-Derived α-Glucan Phosphorylase Enzyme

*Escherichia coli* expressing the *Aquifex aeolicus* VF5-derived α-glucan phosphorylase gene, made in the aforementioned (B), was inoculated with a LB medium (50 μg/ml ampicillin, 1% tryptone manufactured by Difco, 0.5% yeast extract manufacture by Difco, 0.5% NaCl, pH 7.3), and cultured at 37° C. for 5 hours. Then, IPTG (isopropyl-β-D-thiogalactopyranoside) and pyridoxine hydrochloride were added to this culture so that the final concentration became 0.1 mM IPTG and 1 mM pyridoxine hydrochloride and, further, this was cultured at 37° C. for 24 hours. Then, bacterial cells were recovered by centrifugation of the culture, and washed with 20 mM citrate buffer (pH 6.7) to remove medium components. The bacterial cells after washing were suspended in 20 mM citrate buffer (pH 6.7), crushed with a sonicator, and centrifuged, and the supernatant was used as a bacterial cell extract. The resulting bacterial cell extract was heated at 60° C. for 30 minutes. Then, this bacterial cell extract was loaded on a Q-Sepharose FF column which had been previously equilibrated, and this was eluted at a concentration gradient of from 0.1 M to 0.3 M NaCl, in a 20 mM citrate buffer (pH 6.7), to recover a GP-purified enzyme-containing active fraction.

Using about 1 μg of the resulting purified enzyme-containing active fraction, native PAGE (Native polyacrylamide gel electrophoresis) was performed. As a result, in a fraction obtained from Escherichia coli expressing α-glucan phosphorylase, a single band was recognized at the position of the molecular weight of about 150 kDa and, at other places, no band was found. Since the molecular weight of the α-glucan phosphorylase derived from Aquifex aeolicus VF5 is predicted to be about 75 kDa as calculated from their amino acid sequence, as a result of this native PAGE, it is thought that this α-glucan phosphorylase takes a dimer structure. In this manner, it was demonstrated that the α-glucan phosphorylase derived from Aquifex aeolicus VF5 was homogeneously purified.

Production Example 2

Recombination Production of Recombinant Potato α-Glucan Phosphorylase

Type L potato α-glucan phosphorylase was recombination-produced by the following method shown in Japanese Laid-Open Publication No. 2004-526463.

BamHI site was created at the N-terminus and the C-terminus of a potato glucan phosphorylase gene (Nakano et al., Journal of Biochemistry (Tokyo) 106 (1989) 691), this gene was cut with BamHI, and was incorporated into an expression vector pET3d (manufactured by STRATAGENE) that had been previously cut with BamHI to obtain the plasmid pET-PGP113. In this plasmid, a glucan phosphorylase gene was operably linked under control of an isopropyl-β-D-thiogalactopyranoside (IPTG) inducible promoter. This plasmid was introduced into Escherichia coli TG-1 (manufactured by STRATAGENE) by the competent cell method. This Escherichia coli was plated on a plate containing LB medium (1% tryptone (manufactured by Difco), 0.5% yeast extract (manufactured by Difco), 1% sodium chloride, and 1.5% agar)) containing the antibiotic ampicillin, and this was cultured at 37° C. overnight. Escherichia coli grown on this plate was selected to obtain Escherichia coli in which a potato-derived glucan phosphorylase gene had been introduced. It was confirmed by analyzing the sequence of the introduced gene that the resulting Escherichia coli contains the glucan phosphorylase gene. In addition, it was confirmed by activity measurement that the resulting Escherichia coli expresses the glucan phosphorylase.

This Escherichia coli was inoculated in 1 liter of LB medium (1% tryptone (manufactured by Difco), 0.5% yeast extract (manufactured by Difco) and 1% sodium chloride) containing the antibiotic ampicillin, and this was cultured at 37° C. for 3 hours with shaking at 120 rpm. Thereafter, IPTG was added to this medium to 0.1 mM, and pyridoxine was added to this medium to 1 mM, and this was cultured with shaking at 22° C. for a further 20 hours. Then, this culture was centrifuged at 5,000 rpm for 5 minutes to collect the Escherichia coli cells. The resulting cells were suspended in 50 ml of 20 mM Tris-HCl buffer (pH 7.0) containing 0.05% Triton X-100 and, then, this was crushed by sonication to obtain 50 ml of a crushed cell liquid. This crushed liquid contained 4.7 U/mg glucan phosphorylase.

This crushed cell liquid was heated at 55° C. for 30 minutes. After heating, this was centrifuged at 8,500 rpm for 20 minutes to remove insoluble proteins and the like, to obtain the supernatant. The resulting supernatant was applied to an anion exchange resin Q-Sepharose which had been pre-equilibrated, allowing glucan phosphorylase to be adsorbed onto the resin. The resin was washed with a buffer containing 200 mM sodium chloride to remove impurities. Subsequently, the protein was eluted with a buffer containing 300 mM sodium chloride, to obtain the recombinant potato glucan phosphorylase enzyme solution.

Production Example 3

Preparation of Three Kinds of α-Glucan Phosphorylases Derived from Microorganism Using a nucleic acid having a base sequence (base sequence of $76^{th}$ to $544^{th}$ described in ACCESSION No. AJ001088 of GeneBank base sequence database) encoding an amino acid sequence of Thermotoga maritima MSB8-derived α-glucan phosphorylase, a nucleic acid having a base sequence (base sequence of $1^{st}$ to $2151^{th}$ described in ACCESSION No. AJ318499 of GeneBank base sequence database) encoding an amino acid sequence of Thermococcus zilligii AN1-derived α-glucan phosphorylase, or a nucleic acid having a base sequence (base sequence of $1^{st}$ to $1626^{th}$ described in ACCESSION No. CP000924 of GeneBank base sequence database) encoding an amino acid sequence of Thermoanaerobacter pseudethanolicus ATCC33223-derived α-glucan phosphorylase in place of an Aquifex aeolicus VF5-derived α-glucan phosphorylase gene, each α-glucan phosphorylase liquid was obtained in the same manner with the Production Example 1.

Comparative Example 1

Enzymatic Reaction Employing Potato-Derived α-Glucan Phosphorylase

Figure 6:
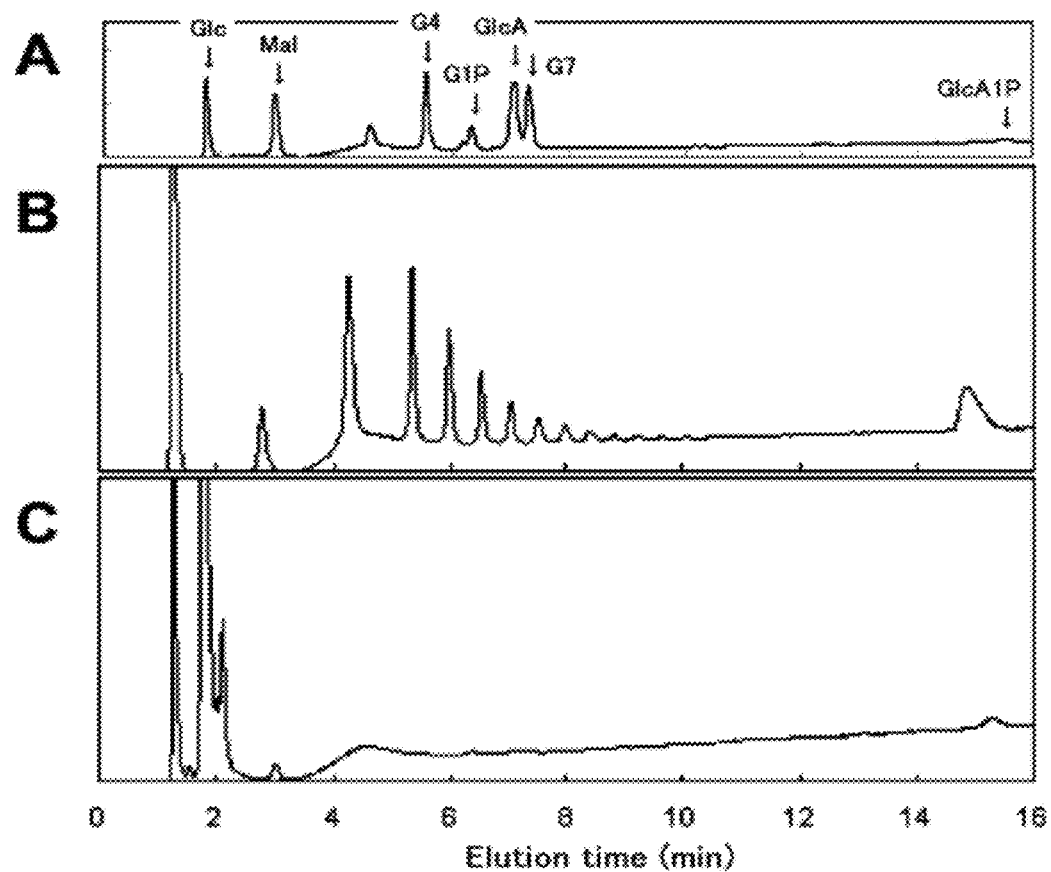
FIG. 6 is the results of analysis of products obtained by acting potato α-glucan phosphorylase on glucuronic acid-1-phosphate and maltotetraose. A is a chromatogram of standard substances (Glc: glucose, Mal: maltose, G4: maltotetraose, G7: maltoheptaose, GlcA: glucuronic acid, G1P: glucose-1-phosphate, GlcA1P: glucuronic acid-1-phosphate). B shows the result of analysis of enzymatic reaction products obtained by acting potato-derived α-glucan phosphorylase on G4 and GlcA-1-P. C shows the result of analysis of reaction products when the enzymatic reaction product (B) obtained using potato-derived α-glucan phosphorylase which was analyzed in B was treated with glucoamylase. In C, since all peaks seen in B disappeared, it can be understood that the enzymatic reaction products obtained using potato-derived α-glucan phosphorylase do not contain a glucan containing a glucuronic acid residue, that is, when potato-derived α-glucan phosphorylase was used, a glucan containing a glucuronic acid residue was not obtained.

After a reaction solution containing 50 mM glucuronic acid-1-phosphate, a 100 mM citrate buffer (pH 6.7), 10 mM maltotetraose, and purified potato-derived α-glucan phosphorylase (type L, 12 Units/ml) produced in Production Example 2 was incubated at 37° C. for 40 hours, the saccharide composition of the reaction solution was analyzed with a HPAEC-PAD apparatus manufactured by DIONEX (pumping system: DX300, detector: PAD-2, analysis column: CarboPacPA100), as it was, or after glucoamylase digestion. Elution was performed under the conditions of flow rate: 1 ml/min, NaOH concentration: 150 mM, sodium acetate concentration: 0 min—50 mM, 2 min—50 mM, 23 min—350 mM (Gradient curve No. 3), 28 min—850 mM (Gradient curve No. 7), 30 min—850 mM. The results are shown in FIG. 6. FIG. 6A confirms an elution position using a sample obtained by adding 100 mM maltotriose (G4) and 100 mM maltoheptaose (G7) as a standard sample of a maltooligosaccharide to a mixture of 100 mM glucose (Glc), 100 mM maltose (Mal), 100 mM glucose-1-phosphate (G1P), 200 mM glucuronic acid (GlcA), and 200 mM glucuronic acid-1-phosphate (GlcA1P) as a standard sample. As shown in FIG. 6B, as a result of analysis of enzymatic reaction products using potato-derived α-glucan phosphorylase, a plurality of peaks including maltooligosaccharides were confirmed. Glucoamylase is an enzyme which degrades maltooligosaccharides starting from a non-reducing end, but when glucuronic acid is bound to a non-reducing end, it cannot digest maltooligosaccharides. When the products of FIG. 6B were digested using this glucoamylase (0.1 mg/ml), as shown in FIG. 6C, all peaks disappeared, and no glucan with a glucuronic acid residue bound thereto was detected, and it was found that a glucan with a glucuronic acid residue bound thereto cannot be synthesized in the case of potato-derived α-glucan phosphorylase.

Comparative Examples 2 to 4

Enzymatic Reactions Using Another Microorganism-Derived α-Glucan Phosphorylase

The saccharide composition of a reaction solution containing 50 mM glucuronic acid-1-phosphate, a 100 mM citrate buffer (pH 6.7), 10 mM maltotetraose, and *Thermotoga maritima*-derived α-glucan phosphorylase (3 Units/ml) produced in Production Example 3 after allowed to react at 37° C. for 40 hours was analyzed with a HPAEC-PAD apparatus manufactured by DIONEX, as it was, or after glucoamylase digestion. This analysis condition is the same as that of Comparative Example 1. No glucan with a glucuronic acid residue bound thereto was detected, and it was found that a glucan with a glucuronic acid residue bound thereto cannot be synthesized, in the case of *Thermotoga maritima*-derived α-glucan phosphorylase. Similar enzymatic reactions were performed using *Thermococcus zilligii*-derived α-glucan phosphorylase (43 Units/ml) or *Thermoanaerobacter pseudethanolicus*-derived α-glucan phosphorylase (19 Units/ml) in place of *Thermotoga maritima*-derived α-glucan phosphorylase, but a glucan with a glucuronic acid residue bound thereto could not be synthesized.

Example 1

Figure 7:
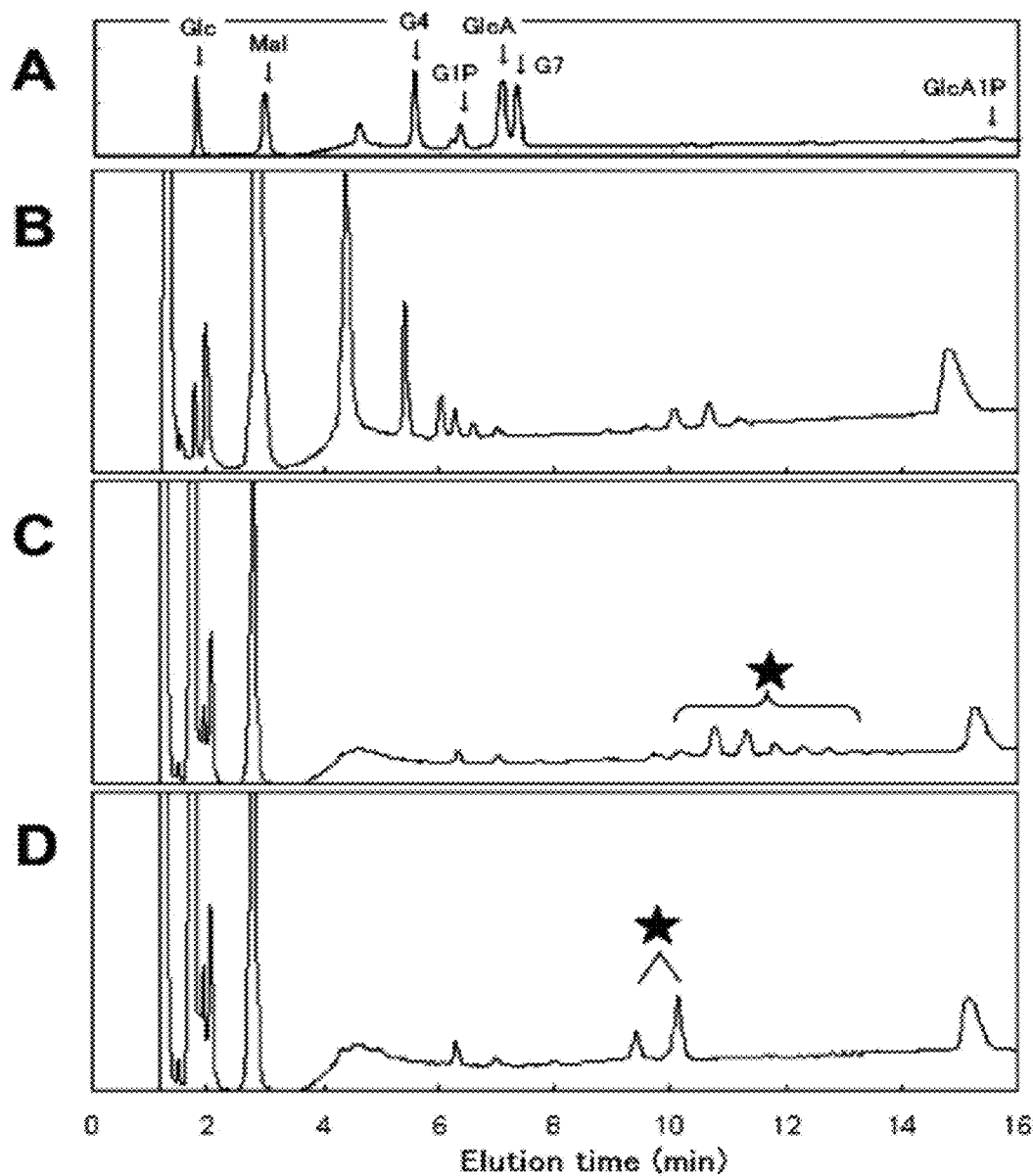
FIG. 7 is the results of analysis of enzymatic reaction products obtained by acting *Aquifex aeolicus* VF5-derived α-glucan phosphorylase on glucuronic acid-1-phosphate and maltotetraose. A is a chromatogram of standard substances (Glc: glucose, Mal: maltose, G4: maltotetraose, G7: maltoheptaose, GlcA: glucuronic acid, G1P: glucose-1-phosphate, GlcA1P: glucuronic acid-1-phosphate). B shows the results of analysis of enzymatic reaction products obtained by acting *Aquifex aeolicus* VF5-derived α-glucan phosphorylase on maltotetraose (G4) and GlcA-1-P. C is the result of analysis of the same enzymatic reaction products as those of B, after glucoamylase treatment. The peaks with an asterisk in C show the glucuronic acid-containing glucans of the present invention. In the glucuronic acid-containing glucans of the present invention, since a glucuronic acid residue is bound to a non-reducing end, it exhibits resistance to glucoamylase. Among the peaks shown with an asterisk in FIG. 7C, a small peak on the left end shows glucuronosyl maltose (GlcA-G2) that is a glucuronic acid residue bound to maltose. A relatively large peak which is second from left is glucuronosyl maltotriose (GlcA-G3). Third peak from left and righter peaks, in turn, as the position goes right, the degree of polymerization increases one by one, such as, GlcA-G4, GlcA-G5 and the like. D is the results of analysis of the same enzymatic reaction products as those of B, after treatment with glucoamylase and α-amylase. The glucuronic acid-containing glucans of the present invention (the peaks with an asterisk in FIG. 7C) were degraded with α-amylase, and new two peaks were generated on a low molecular weight side. Therefore, it can be understood that when *Aquifex aeolicus* VF5-derived α-glucan phosphorylase is used, glucans containing glucuronic acid residue(s) are obtained.

Production of Glucuronic Acid-Containing Glucan Using Maltotetraose as Raw Material After a reaction solution containing 50 mM glucuronic acid-1-phosphate, a 100 mM citrate buffer, 10 mM maltotetraose and *Aquifex aeolicus* VF5-derived α-glucan phosphorylase (37.5 Units/ml) was incubated at 37° C. for 40 hours, the saccharide composition of the reaction solution was analyzed with a HPAEC-PAD apparatus manufactured by DIONEX, as it was, or after glucoamylase digestion. This analysis condition is the same as that of Comparative Example 1. The results are shown in FIG. 7. FIG. 7A is a diagram confirming elution positions of the standard sample. As shown in FIG. 7B, as a result of analysis of enzymatic reaction products using Aquifex-derived α-glucan phosphorylase, a plurality of peaks including maltooligosaccharides were confirmed. As a result of digestion of the products of Aquifex-derived α-glucan phosphorylase of FIG. 7B using glucoamylase (0.1 mg/ml), as shown in FIG. 7C, since peaks indicated with an asterisk were not degraded, it was found that these peaks indicated with an asterisk are glucan compounds containing a glucuronic acid residue on a non-reducing end. Further, when this product was digested using α-amylase being an enzyme which randomly degrades an α-1,4 glucosyl bond by a maltose unit, as shown in FIG. 7D, since all peaks shifted to the 2 peaks indicated with a mark, it was confirmed that a glucan containing a glucuronic acid residue is an α-1,4 glucan. A glucan in which one molecule of a glucuronic acid residue is bound to a non-reducing end of a maltooligosaccharide was obtained. As a result, it was confirmed that a glucuronic acid-containing glucan (FIG. 7C, asterisk) can be produced using *Aquifex aeolicus* VF5-derived α-glucan phosphorylase.

Example 2

Figure 8:
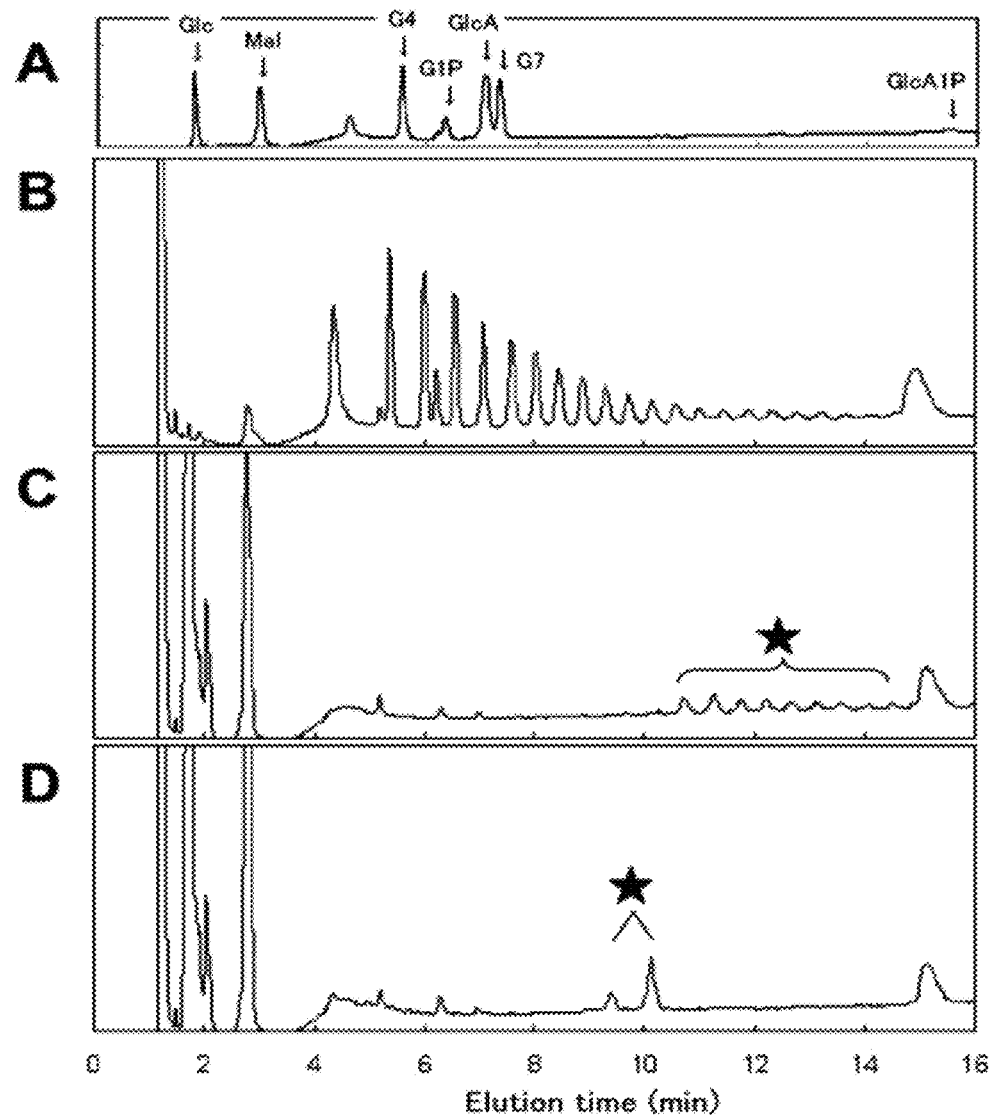
FIG. 8 is the results of analysis of products obtained by acting *Aquifex aeolicus* VF5-derived α-glucan phosphorylase on glucuronic acid-1-phosphate and maltoheptaose. A is a chromatogram of standard substances (Glc: glucose, Mal.

Production of Glucuronic Acid-Containing Glucan Using Maltoheptaose as Raw Material After a reaction solution containing 50 mM glucuronic acid-1-phosphate, a 100 mM citrate buffer, 10 mM maltoheptaose, and *Aquifex aeolicus* VF5-derived α-glucan phosphorylase (37.5 Units/ml) was incubated at 37° C. for 40 hours, the saccharide composition of the reaction solution was analyzed with a HPAEC-PAD apparatus manufactured by DIONEX, as it was, or after glucoamylase digestion. This analysis condition is the same as that of Comparative Example 1. The results are shown in FIG. 8. FIG. 8A is a diagram confirming elution positions of the standard sample. As shown in FIG. 8B, as a result of analysis of enzymatic reaction products using Aquifex-derived α-glucan phosphorylase, a plurality of peaks including maltooligosaccharides were confirmed. The average degree of polymerization of the products was greater than that when maltotetraose was used. When the products of Aquifex-derived α-glucan phosphorylase of FIG. 8B were digested using glucoamylase (0.1 mg/ml), as shown in FIG. 8C, since peaks indicated with an asterisk were not degraded, it was found that these are glucan compounds containing a glucuronic acid residue on a non-reducing end. Further, when this product was digested using α-amylase, as shown in FIG. 8D, since all peaks shifted to the 2 peaks indicated with a mark, it was confirmed that a glucan containing a glucuronic acid residue is assuredly an α-1,4 glucan. A glucan with one molecule of glucuronic acid added to a non-reducing end of a maltooligosaccharide, having a greater molecular size than that when maltotetraose was used was obtained (FIG. 8C, asterisk).

Example 3

Measurement of Molecular Weight and Identification of Structure of Glucuronic Acid-Containing Glucan In order to determine the structure of the glucuronic acid-containing glucan obtained in Example 1, a peak indicated with an arrow in the chromatogram of FIG. 9A (the same diagram as in FIG. 7C) was fractionated. Fractionation was performed by providing a branch to a tube between a column and a detector of a HPAEC-PAD apparatus, and performing flow path switching to a fractionation side at elution of an objective peak. The results of analysis of a sample after fractionation, with the HPAEC-PAD apparatus are shown in FIG. 9B. These analysis conditions are the same as those of Comparative Example 1. When this sample was desalted using a Sephadex G-10 column (volume 20 ml), and lyophilized and, thereafter, the molecular weight was obtained by TOF-MS (Voyager Biospectrometry Workstation Ver. 5.1 manufactured by Shimadzu), a value of 703.22 was obtained. This molecular weight was consistent with a theoretical value of maltotriose having a glucuronic acid on an terminus. The structure of the substance of FIG. 9B (the same as the substance with an arrow of FIG. 9A) is shown in FIG. 9C.

Example 4

Production of Glucuronic Acid-Containing Glucan Using Branched Dextrin as Raw Material A reaction solution containing 50 mM glucuronic acid-1-phosphate, a 100 mM citrate buffer, 2% branched dextrin (trade name: Cluster Dextrin; molecular weight 190 KDa:

manufactured by EZAKI GLICO CO., LTD.) and *Aquifex aeolicus* VF5-derived glucan phosphorylase (37.5 Units/ml) was incubated at 37° C. for 18 hours to allowed to occur an enzymatic reaction. Cluster Dextrin is a dextrin having lower molecular weight obtained by allowing a branching enzyme to react to corn-derived waxy corn starch, and is a high-molecular weight branched dextrin containing branched chains bound with an α-1,6 bond. The results of analysis of the structure of enzymatic reaction products with a HPAEC-PAD apparatus manufactured by DIONEX are shown in FIG. 10. This analysis condition is the same as that of Comparative Example 1. FIG. 10A is a diagram confirming elution positions of the standard sample. FIG. 10B shows analysis of branched parts of Cluster Dextrin before an enzymatic reaction after digestion with isoamylase, with a HPAEC-PAD apparatus, and shows a distribution of lengths of glucan linear chain parts of a Cluster Dextrin molecule. FIG. 10C is the results of analysis of enzymatic reaction products using Aquifex-derived α-glucan phosphorylase, after digestion with isoamylase. A plurality of peaks including maltooligosaccharides were confirmed, and a great peak group was seen, particularly, at a part indicated with an arrow on 9 minutes and thereafter. When the isoamylase digest of FIG. 10C was digested using glucoamylase (0.1 mg/ml), as shown in FIG. 10D, the peak group indicated with an arrow was not degraded with glucoamylase, and it was found that these are glucan compounds containing a glucuronic acid residue on a non-reducing end. From these results, it was confirmed that a high-molecular weight branched dextrin in which each one molecule of glucuronic acid residue is bound to many non-reducing ends was obtained. When the ratio of introduction of glucuronic acid into a non-reducing end was obtained, it was confirmed that glucuronic acid residues have been introduced into about 70% of non-reducing ends. In this manner, the glucuronic acid-containing glucan (shown in FIG. 2) of the present invention, having a structure in which a glucuronic acid residue is bound to many non-reducing ends, was produced.

Production Example 4

Production of Various Glucans Having Different Structures

Production Example 4-1

Production of Branched Glucan (B)

50 g of a waxy corn starch (manufactured by SANWA CORNSTARCH CO., LTD) was suspended into 1,000 ml of a 10 mM sodium phosphate buffer (pH 7.0), and the suspension was heated to about 100° C. to gelatinize the starch. 200,000 units of a highly thermostable branching enzyme prepared according to the method described in Example 1 of Japanese Laid-Open Publication No. 2000-316581 to prepare a reaction solution was added to the starch paste which had been cooled to about 70° C., and then which was allowed to react at 70° C. for 16 hours. After the reaction solution was heated at 100° C. for 20 minutes, the supernatant after centrifuging it at 6,500 rpm for 10 minutes was filtered with a membrane having a pore diameter of 0.8 μm. Then, the filtrate was desalted using a gel filtration chromatography (AKTA purifier) system (column: HiPrep™ 26/10 Desalting manufactured by GE Healthcare) to remove low-molecular weight polysaccharides. About 1,000 ml of the filtrate was divided into 7.5 ml of aliquots, and applied to a gel filtration chromatography system, and elution fractions of from 2.7 minutes to 3.7 minutes at a flow rate of 10 ml/min were fractionated, respectively. The elution fractions obtained from 1,000 ml of the filtrate were combined, the combined elution fractions was filtered with a membrane having a pore diameter of 0.2 μm, and then lyophilized to obtain about 35 g of a powder of a branched glucan (B). The weight average molecular weight of the branched glucan (B) was investigated using a high performance liquid chromatography (HPLC) system (column: OHPAKSB-806 MHQ, manufactured by SHOWA DENKO K.K.) equipped with a multiangle laser light scattering detector (DAWN DSP, manufactured by Wyatt Technology Corporation) and a differential refractometer (Shodex RI-71, manufactured by SHOWA DENKO K.K.). 20 mg of a powder of the branched glucan (B) was dissolved in 10 ml of a 100 mM aqueous sodium nitrate solution, and the solution was filtered with a membrane having a pore diameter of 0.45 μm to obtain a filtrate. 100 μl of the resulting filtrate was injected into the aforementioned HPLC system. It was shown that the weight average molecular weight of the branched glucan (B) is about 110 K (about 670 in terms of the degree of polymerization).

When isoamylase was allowed to act on the aforementioned branched glucan (B), and the reducing power was investigated by the modified Park-Johnson method (Hizukuri et al., Starch, Vol., 35, pp. 348-350, (1983)), it was shown that the average unit chain length of branching was about 17, and the number of branching was about 40.

Production Example 4-2

Production of Branched Glucan (P)

An aqueous sugar solution (prepared by dissolving 150 g of sugar in 1,000 ml of distilled water, and filtering the solution with a membrane having a pore diameter of 0.2 μm) (800 ml), 20 ml of a 5% aqueous branched glucan (B) solution (prepared by filtering a 5% aqueous solution of the branched glucan (B) produced by the aforementioned Production Example 4-1 of branched glucan, with a membrane having a pore diameter of 0.2 μm), 4 ml of a 1 M sodium phosphate buffer (pH 7.0), 1,800 U of recombinant *Streptococcus mutans* sucrose phosphorylase prepared by the method as described in Example 2.5 of International Publication WO 02/097107 pamphlet, 1,200 U of glucan phosphorylase produced in Production Example 1 of the present application, and 600,000 U of the branching enzyme described in Japanese Laid-Open Publication No. 2000-316581 used in Production Example 4-1 were mixed, and the liquid volume was adjusted to 1,000 ml with distilled water, followed by allowing reaction at 55° C. for 24 hours. After the reaction solution was heated at 100° C. for 20 minutes and centrifuged at 6,500 rpm for 20 minutes, the supernatant was filtered with a membrane having a pore diameter of 0.8 μm. Further, the resulting filtrate was desalted using a gel filtration chromatography (AKTA purifier) system (column: HiPrep™ 26/10 Desalting, manufactured by GE Healthcare) to remove low-molecular weight polysaccharides. About 1,000 ml of the filtrate was divided into 7.5 ml of aliquots, and applied to a gel filtration chromatography system, and elution fractions of from 2.7 minutes to 3.7 minutes at a flow rate of 10 ml/min were fractionated, respectively. The elution fractions obtained from 1,000 ml of the filtrate were combined, the combined elution fractions was filtered with a membrane having a pore diameter of 0.2 μm, and then lyophilized to obtain about 40 g of the branched glucan (P). When the weight average molecular weight of the glucan was similarly investigated as the branched glucan in Production Example 4-1, it was shown that the weight average molecular weight of the branched glucan (P) was about 4,000 K (about 25,000 in terms of the degree of polymerization). In addition, it was shown that the average unit chain length of the branching was about 15, and the number of branching was about 1,600. Further, when the average particle size of the branched glucan (P) was measured with a concentrated system particle size analyzer (FPAR-1000, manufactured by Otsuka Electronics Co., Ltd.), the average particle size was about 37 μm.

Example 5

Production of Various Glucuronic Acid-Containing Branched Glucans Having Different Glucuronic Acid Transfer Ratios

*Aquifex aeolicus* VF5-derived α-glucan phosphorylase (14 Units/ml) prepared in Production Example 1 was allowed to act on a reaction solution containing the branched glucan (B) produced in Production Method 4-1, glucuronic acid 1-phosphate, and a 100 mM sodium acetate buffer (pH 5.5) at 50° C. for 18 hours to produce three kinds of glucuronic acid-containing branched glucans (BA1, BA2 and BA3) having different glucuronic acid transfer ratios. The reaction conditions of the various glucuronic acid-containing branched glucans (branched glucan (B) concentration, glucuronic acid-1-phosphate concentration, and addition ratio between branched glucan (B) and glucuronic acid-1-phosphate), and the glucuronic acid transfer ratio of the resulting glucuronic acid-containing branched glucan are shown in Table 3.

The transfer ratio of glucuronic acid to the branched glucan (B) was calculated by quantifying the amount of free inorganic phosphate in the reaction solution, and using the following equation:

(the number of inorganic phosphate generated in the reaction solution/the average number of unit chains in the reaction solution)×100(%)

The amount of inorganic phosphate was obtained as follows: a molybdenum reagent (15 mM ammonium molybdate, and 100 mM zinc acetate) (800 μl) was mixed with an aqueous solution (200 μl) containing inorganic phosphate, subsequently, 200 μl of a 568 mM aqueous ascorbic acid solution (pH 5.0) was added, and the mixture was stirred to obtain a reaction system. After this reaction system was retained at 30° C. for 20 minutes, absorbance at 850 nm was measured using a spectroscopic photometer. Using inorganic phosphate having a known concentration, absorbance was measured similarly, and a standard curve was produced. Absorbance obtained in a sample was fitted on this standard curve to obtain inorganic phosphate in the sample.

By changing the addition ratio of the branched glucan (B) to glucuronic acid-1-phosphate ("the concentration of the branched glucan (B)":"the concentration of glucuronic acid-1-phosphate" (molar ratio)) to 1:0.5, 1:1, or 1:2 as shown in Table 3, thereby, the transfer ratio of glucuronic acid to a non-reducing end of the branched glucan was regulated to 25%, 50% and 70%, respectively. In this manner, glucuronic acid-containing branched glucans (BA1, BA2, and BA3) were produced.

TABLE 3

Production of glucuronic acid-containing branched glucans (BA1, BA2 and BA3)

|  |  | BA1 | BA2 | BA3 |
|---|---|---|---|---|
| Reaction condition | Branched glucan (B) concentration | 10 mM | 10 mM | 10 mM |
|  | Glucuronic acid-1-phosphate concentration | 5 mM | 10 mM | 20 mM |
|  | Glucuronic acid-1-phosphate addition ratio *[1] | 1:0.5 | 1:1 | 1:2 |
| Transfer ratio of glucuronic acid to non-reducing end of branched glucan |  | 25% | 50% | 70% |

*[1] = (glucuronic acid-1-phosphate/branched glucan (B))

Example 6

Production of Glucuronic Acid-Containing Branched Glucan Using Branched Glucans Having Different Unit Chain Lengths

*Aquifex aeolicus* VF5-derived α-glucan phosphorylase (1 Unit/ml) was allowed to act on a reaction solution containing the branched glucan (B) produced in Production Method 4-1, glucose 1-phosphate, and a 100 mM sodium acetate buffer (pH 5.5) at 50° C. for 18 hours to elongate a unit chain, thereby, two kinds of branched glucans having different unit chain lengths (B2 and B3) were synthesized. The unit chain length of branched glucans (B2 and B3) was calculated by quantifying the amount of inorganic phosphate in the reaction solution. The amount of inorganic phosphate in the reaction solution corresponds to the amount of elongated glucose, and the number of glucose residues elongated to a non-reducing end of the branched glucan (average unit chain length) was obtained from the amount of glucose and the number of non-reducing ends (40) of the branched glucan. Since the number of glucose residues elongated to a non-reducing end of the branched glucans B2 and B3 is 20 and 40, respectively, and the average unit chain length of the branched glucans B2 and B3 is the total of the unit chain length 17 of the branched glucan (B) before the reaction and the number of elongated glucose residues, the unit chain length was 37 and 57, respectively.

The reaction condition for elongating the branched glucans (B2 and B3) (the concentration of the branched glucan (B) and the concentration of glucose 1-phosphate), the number of glucose residues elongated to a non-reducing end, and the unit chain length of the branched glucans (B2 and B3) are shown in Table 4.

TABLE 4

Production of branched glucans (B2 and B3)

|  | B2 | B3 |
|---|---|---|
| Branched glucan (B) concentration | 10 mM | 5 mM |
| Glucose-1-phosphate concentration | 200 mM | 200 mM |
| Number of glucose residues elongated to non-reducing end (Average unit chain length) | 20 | 40 |
| Unit chain length of each branched glucan | 37 | 57 |

Then, a synthesis reaction solution of these branched glucans (B2 and B3) was heated at 100° C. for 10 minutes, the supernatant of the reaction solution was recovered after centrifugation at 12,000 rpm, and this was desalted using a PD-10 column to remove a low-molecular weight molecule, thereby, branched glucans having different unit chains (B2 and B3) were produced.

*Aquifex aeolicus* VF5-derived α-glucan phosphorylase (14 Units/ml) was allowed to act on the branched glucan B, B2 or B3, glucuronic acid 1-phosphate, and a 100 mM sodium acetate buffer (pH 5.5) at 50° C. for 20 hours to produce glucuronic acid-containing branched glucans (BA4 to BA9). The glucuronic acid transfer ratio of BA4 to BA9 was obtained by the method of Example 5, and is shown in Table 5.

TABLE 5

Production of glucuronic acid-containing branched glucans (BA4 to BA9)

| | Synthesized glucuronic acid-containing branched glucan | | | | | |
|---|---|---|---|---|---|---|
| | BA4 | BA5 | BA6 | BA7 | BA8 | BA9 |
| Branched glucan used in glucuronic acid binding and its concentration (mM) | B 7 | B 7 | B2 7 | B2 7 | B3 7 | B3 7 |
| Glucuronic acid-1-phosphate concentration (mM) | 3.5 | 14 | 3.5 | 14 | 3.5 | 14 |
| Glucuronic acid transfer ratio (%) | 25 | 70 | 25 | 70 | 25 | 70 |

Example 7

Elongation of Unit Chain of Glucuronic Acid-Containing Branched Glucan

*Aquifex aeolicus* VF5-derived α-glucan phosphorylase (5 Units/ml) was allowed to act on a reaction solution containing the glucuronic acid-containing branched glucan (BA1 or BA3) obtained in Example 5, glucose-1-phosphate and a 100 mM sodium acetate buffer (pH 5.5) at 50° C. for 18 hours, thereby, various glucuronic acid-containing branched glucans (BA10 to BA17) having different unit chain lengths were synthesized. The reaction conditions are shown in Table 6.

TABLE 6

Reaction conditions in elongation of glucuronic acid-containing branched glucan (amounts of BA1 or BA3 and Glucose-1-phosphate)

| | Synthesized glucuronic acid-containing branched glucan | | | | | | | |
|---|---|---|---|---|---|---|---|---|
| | BA10 | BA11 | BA12 | BA13 | BA14 | BA15 | BA16 | BA17 |
| Branched glucan (BA1 or BA3) and its concentration (mM) | BA1 5.7 | BA1 5.7 | BA1 5.7 | BA1 5.7 | BA3 5.7 | BA3 5.7 | BA3 5.7 | BA3 5.7 |
| Glucose-1-phosphate (mM) | 22 | 43 | 60 | 86 | 8 | 16 | 32 | 60 |

The average unit chain length of the glucuronic acid-containing branched glucans (BA10 to BA17) was obtained by the same method as that of Example 6, by quantifying the amount of inorganic phosphate in the reacting solution. Further, from the unit chain length, the average molecular weight of a unit chain of the branched glucan was obtained. In this manner, the glucuronic acid-containing branched glucans (BA10 to BA17) shown in Table 7 were produced.

TABLE 7

Unit chain length of various glucuronic acid-containing branched glucans, and average molecular weight of unit chain

| | B | BA10 | BA11 | BA12 | BA13 | BA14 | BA15 | BA16 | BA17 |
|---|---|---|---|---|---|---|---|---|---|
| Average unit chain length | 17 | 27 | 37 | 45 | 57 | 27 | 37 | 57 | 60 |
| Average molecular weight of unit chain | 2800 | 4400 | 6000 | 7300 | 9200 | 4400 | 6000 | 9200 | 1500 |

After each glucuronic acid-containing branched glucan (BA10 to BA17) was digested with isoamylase by the same method as that of Example 4, this was further digested with glucoamylase, and it was confirmed that these glucans are a glucan containing a glucuronic acid residue.

In addition, each 10 μl of reaction solutions of these glucuronic acid-containing branched glucans (BA10 to BA17) were added to 1 ml of 0.05 mol of an iodine solution, respectively, to perform iodine staining; and the iodine inclusion ability was compared. Regarding the iodine inclusion ability, absorbance at 660 nm was measured using a spectroscopic photometer. The results are shown in Table 8. As the value of absorbance becomes greater, the higher the iodine inclusion ability. The value of absorbance of water is 0.01, the value of absorbance of the branched glucan (B) is 0.04, and it is shown that these molecules have no inclusion ability. On the other hand, as the unit chain length is greater, the value of absorbance is greater, thereby their high inclusion ability was shown. By elongating a unit chain of the glucuronic acid-containing branched glucan to which glucuronic acid is not bound, the inclusion ability was imparted to the glucan of the present invention.

TABLE 8

Average unit chain length and absorbance at 660 nm of various glucuronic acid-containing branched glucans (BA10 to BA17) after iodine staining

| | B | BA10 | BA11 | BA12 | BA13 | BA14 | BA15 | BA16 | BA17 |
|---|---|---|---|---|---|---|---|---|---|
| Average unit chain length | 17 | 27 | 37 | 45 | 57 | 27 | 37 | 57 | 60 |
| Absorbance at 660 nm | 0.04 | 0.15 | 0.44 | 0.82 | 0.74 | 0.07 | 0.11 | 0.33 | 1.26 |

In addition, when an elongated branched glucan having an average unit chain length of 15,000 (a control with no glucuronic acid added thereto) and the glucuronic acid-containing branched glucan of BA17 were frozen and stored and, thereafter, thawed at room temperature, both were precipitated due to aging, but the glucuronic acid-containing branched glucan of BA17 was easily dissolved by heating. On the other hand, the elongated branched glucan having an average unit chain length of 15,000 could not be dissolved. By binding glucuronic acid to a non-reducing end, solubility of the elongated branched glucan was enhanced.

Example 8

Production of Mannose-Containing Branched Glucan Using Glucuronic Acid-Containing Branched Glucan (BA1)

*Aquifex aeolicus* VF5-derived α-glucan phosphorylase (14 Units/ml) was allowed to act on a reaction solution containing the glucuronic acid-containing branched glucan (10 mM BA1) obtained in Example 5, 10 mM mannose 1-phosphate, and a 100 mM sodium acetate buffer (pH 5.5) at 50° C. for 18 hours, thereby, a mannose-containing branched glucan was synthesized. The mannose transfer ratio in the branched glucan was obtained by the same method as that of Example 5. In this manner, a branched glucan having a content of glucuronic acid of 25% and a mannose transfer ratio of 44% was produced. Further, it was confirmed by analysis with a HPAEC-PAD apparatus after glucoamylase digestion of the branched glucan which had been isoamylase-digested similar to as in Example 4 that the mannose-containing branched glucan of the present example has a glucan containing a glucuronic acid residue and a glucan containing a mannose residue.

Example 9

Production of Galactose-Containing Branched Glucan Using Glucuronic Acid-Containing Branched Glucan (BA1)

*Aquifex aeolicus* VF5-derived α-glucan phosphorylase (14 Units/ml) was allowed to act on a reaction solution containing the glucuronic acid-containing branched glucan (10 mM BA1) obtained in Example 5, 10 mM galactose 1-phosphate, and a 100 mM sodium acetate buffer (pH 5.5) at 50° C. for 18 hours, thereby, a galactose-containing branched glucan was synthesized. The galactose transfer ratio in the branched glucan was obtained by the same method as that of Example 5. In this manner, the branched glucan having a content of glucuronic acid of 25% and a galactose transfer ratio of 39% was produced. Further, it was confirmed by analysis with a HPAEC-PAD apparatus after glucoamylase digestion of the branched glucan which had been isoamylase-digested similar to as in Example 4 that the galactose-containing branched glucan of the present example has a glucan containing a glucuronic acid residue and a glucan containing a galactose residue.

Example 10

Production of Various Glucuronic Acid-Containing Branched Glucans (PA1, PA2 and PA3) Having Different Glucuronic Acid Transfer Ratios

*Aquifex aeolicus* VF5-derived α-glucan phosphorylase (14 Units/ml) was allowed to act on a reaction solution containing the branched glucan (P) produced in Production Method 4-2, glucuronic acid 1-phosphate, and a 100 mM sodium acetate buffer (pH 5.5) at 50° C. for 18 hours, thereby, three kinds of glucuronic acid-containing branched glucans (PA1, PA2 and PA3) having different glucuronic acid transfer ratios were produced. The reaction conditions of various glucuronic acid-containing branched glucans (branched glucan (P), glucuronic acid-1-phosphate concentration, (addition ratio of branched glucan (P) and glucuronic acid 1-phosphate), and the glucuronic acid transfer ratio of the resulting glucuronic acid-containing branched glucan are shown in Table 9.

The transfer ratio to the branched glucan (P) of glucuronic acid was calculated by the method of Example 5. As shown in Table 9, by changing the addition ratio of glucuronic acid-1-phosphate relative to the branched glucan (P) to 1:0.5, 1:1, and 1:3, respectively, glucuronic acid-containing branched glucans (PA1, PA2 and PA3), in which the content of glucuronic acid to a non-reducing end of the branched glucan was regulated to 30%, 40% and 70%, respectively, were produced.

TABLE 9

Production of various glucuronic acid-containing branched glucans (PA1, PA2 and PA3)

|  | PA1 | PA2 | PA3 |
| --- | --- | --- | --- |
| Branched glucan concentration | 10 mM | 10 mM | 10 mM |
| Glucuronic acid-1-phosphate concentration | 5 mM | 10 mM | 30 mM |
| Glucuronic acid-1-phosphate addition ratio (Glucuronic acid-1-phosphate/branched glucan) | 1:0.5 | 1:1 | 1:3 |
| Transfer ratio of glucuronic acid to non-reducing end of branched glucan | 30% | 40% | 70% |

Example 11

Cationization of Glucuronic Acid-Containing Glucan (BC)

Using the glucuronic acid-containing glucan (BA2) obtained in Example 5, a 2 wt % aqueous solution was prepared. 1 ml of the prepared aqueous solution and 2 μl of 1 N hydrochloric acid were added to a test tube, and the mixture was stirred at 10° C. to obtain an aqueous solution having a pH of 5. 2 μl of N,N-diethylethylenediamine was added to this aqueous solution, the mixture was stirred, 2 mg of 1-ethyl-3-(3-dimethylaminopropyl)carbodiimide (EDC) was further added, and stirring was continued at 10° C. for 3 hours. After 3 hours, 1 ml of the reaction solution was placed on a gel filtration column (PD-10), 1.5 ml of ultrapure water was passed therethrough and, thereafter, 2 ml was recovered with ultrapure water to obtain a cationized product (BC) of a glucuronic acid-containing glucan.

Example 12

Use Example 1: Making Protein to be a Macromolecule (Dehydration Condensation of BA and Insulin)

Two mg of albumin (derived from bovine serum) and 2 mg of the glucuronic acid-containing glucan (BA2) of Example 5 were dissolved in 700 μl of a 0.1M 2-[N-morpholino]ethane sulfonic acid (MES) buffer (pH 5.0). After 1 mg of 1-ethyl-3-(3-dimethylaminopropyl)carbodiimide (EDC) was added and allowed to react at room temperature for 2 hours, the reaction solution was diluted to ¼ with water, and desalted using a PD-10 column (manufactured by GE). The resulting solution was analyzed by FPLC analysis using a Superose 6 10/300 GL column (a column for size fractionation, manufactured by GE). Using an eluent (a 50 mM phosphate buffer (pH 7.0), 150 mM sodium chloride), elusion was performed at 0.5 ml/min, and the product was detected with UV (280 nm). The product of a sample obtained by a condensation reaction of the glucuronic acid-containing glucan and albumin had an early elution time and, it was shown that the molecular size is great. Therefore, it was shown that the glucuronic acid-containing glucan and a protein can be dehydration-condensed to prepare a macromolecule.

Example 13

Use Example 2: Stabilization of Protein and Complex Formation (BA)

After 20 μg of FGF-basic (manufactured by Pepro Tech Ec, Inc.) which is a basic protein, and 0.5 mg of the glucuronic acid-containing glucan (BA2) of Example 5 were mixed in 0.1 ml of ion-exchanged water, it was analyzed by FPLC analysis using a Superose 6 10/300 GL column (a column for size fractionation, manufactured by GE). Using ion-exchanged water as an eluent, elution was performed at 0.5 ml/min, and the product was detected with UV (280 nm). It was shown that, as compared with the case where the glucuronic acid-containing glucan was not added to a FGF-basic solution, the elution time of the product was early, and the molecular size is greater, in the case where it was added. Therefore, it was shown that the glucuronic acid-containing glucan can form a complex with a basic protein. The results are shown in FIG. 11.

Example 14

Use Example 3: Stabilization of Nucleic Acid and Complex Formation (BC)

The cationized glucan (BC) obtained in Example 11 (0.2 μg) and 0.5 μg of lambda DNA-HindIII fragment (manufactured by TAKARA BIO INC.) were dissolved in 20 μl of ion-exchanged water, the solution was allowed to stand at room temperature for 5 minutes, and it was subjected to 1% agarose gel electrophoresis. When the cationized glucan was added, mobility of the DNA fragment was remarkably slow, as compared with the case where the cationized glucan was not added. Therefore, the cationized glucan can form a complex with a DNA. The results are shown in FIG. 12.

Example 15

Acetylation of Various Glucans (B and P) (AcB and AcP)

The glucans (B and P) obtained in Production Example 4 were dissolved in DMSO, respectively, mixing was performed according to formulation of Table 10, and stirring was performed at 25° C. for 1 hour. The resulting solution was diluted 2-fold with ultrapure water, and 1 ml of the diluted solution was placed on a gel filtration column (PD-10), and 1.5 ml of ultrapure water was passed therethrough and, thereafter, 2 ml was recovered with ultrapure water to perform purification. 200 μl of a 5 N aqueous sodium hydroxide solution was added to 300 μl of the sample after purification, this was heated at 55° C. for 30 minutes to perform a deacetylation reaction. 300 μl of a 1 N Tris buffer (pH 7) was added to this reaction solution, and 200 μl of 5 N hydrochloric acid was further added to perform neutralization. When using the solution after neutralization, glucose was quantified by a phenol sulfuric acid method, and free acetic acid was quantified with a free acetic acid quantification kit, thereby, the degree of acetylation was obtained, acetylated glucans (AcB1 to AcB5 and AcP1 to AcP5) having a degree of acetylation of 0.1 to 1.3 were obtained (Table 11). Each sample aqueous solution was lyophilized to obtain a powder of an acetylated glucan.

TABLE 10

| B | | | | | |
|---|---|---|---|---|---|
| SAMPLE NAME | AcB1 | AcB2 | AcB3 | AcB4 | AcB5 |
| 1.87 wt % B in DMSO (μl) | 800 | 800 | 800 | 800 | 800 |
| DMSO (μl) | 143 | 139 | 132 | 128 | 123 |
| 4% $Na_2CO_3$ in $H_2O$ (μl) | 50 | 50 | 50 | 50 | 50 |
| 5M vinyl acetate in DMSO (μl) | 7 | 11 | 18 | 22 | 27 |

| P | | | | | |
|---|---|---|---|---|---|
| SAMPLE NAME | AcP1 | AcP2 | AcP3 | AcP4 | AcP5 |
| 2.55 wt % P in DMSO (μl) | 800 | 800 | 800 | 800 | 800 |
| DMSO (μl) | 140 | 135 | 125 | 120 | 113 |
| 4% $Na_2CO_3$ in $H_2O$ (μl) | 50 | 50 | 50 | 50 | 50 |
| 5M vinyl acetate in DMSO (μl) | 10 | 15 | 25 | 30 | 37 |

TABLE 11

| SAMPLE NAME | AcB1 | AcB2 | AcB3 | AcB4 | AcB5 |
|---|---|---|---|---|---|
| Degree of acetylation (DS) | 0.1 | 0.5 | 0.9 | 1.3 | 1.3 |
| SAMPLE NAME | AcP1 | AcP2 | AcP3 | AcP4 | AcP5 |
| Degree of acetylation (DS) | 0.2 | 0.3 | 0.5 | 0.9 | 1.1 |

Example 16

Amylase Degradability of Various Acetylated Glucans

Using powders of acetylated glucans (AcB1, AcB2, AcB3, AcB4 and AcP1, AcP3, AcP4, AcP5) having different degrees of acetylation obtained in Example 15, respectively, 0.2 wt % aqueous solutions were prepared. 4 μl of a 1 M acetate buffer, respectively was added to 200 μl of these aqueous solutions, 2 μl of pig pancreas-derived α-amylase which had been adjusted to 94 units/ml was further added, and degradability with α-amylase was confirmed. The results are shown in FIG. 13. In FIG. 13, a black circle indicates AcB and a black triangle indicates AcP. As shown in FIG. 13, it was found that the acetylated glucan having a degree of acetylation of 0.5 or more is suppressed in degradation with α-amylase.

Example 17

Serum Acetylase Degradability of Various Acetylated Glucans

Whole blood of a human was allowed to stand at room temperature for 1 hour, and centrifugation was performed at 5,000 rpm for 15 minutes. The supernatant was recovered as serum, and 200 μl of the resulting serum and 200 μl of a 0.2 wt %-adjusted aqueous solution of the acetylated glucan (AcB2, AcB3, AcB4 and AcP1, AcP3, AcP5) obtained in Example 15 were mixed. At 2, 4 and 6 hours at 37° C., each 80 μl of the mixture was sampled, and free acetic acid was quantified with a free acetic acid quantification kit. The results at 6 hours of sampling are shown in FIG. 14. It was found that, in any of the acetylated glucans, acetyl was released by acetylase in serum.

Example 18

Addition of Glucuronic Acid to Various Acetylated Glucans (AcBA)

A reaction solution containing 30 mM glucuronic acid-1-phosphate, a 50 mM acetate buffer (pH 5.5) and *Aquifex aeolicus* VF5-derived glucan phosphorylase (18 Units/ml), containing 160 mg of the acetylated glucan (AcB2) obtained in Example 15 was allowed to react at 60° C. for 16 hours to perform an enzymatic reaction. When the content of inorganic phosphate was measured by the method described in Example 5, it was found that glucuronic acid was introduced into 41.7% of non-reducing ends of the acetylated glucan.

Example 19

Fluorescent Labeling of Glucuronic Acid-Containing Glucan (F-B, F-AcBA)

Each glucan of B obtained in Production Example 4-1 and AcBA2 obtained in Example 18 was prepared into a 2 wt % DMSO solution. 2 ml of each glucan in DMSO solution was placed into a test tube, and the solution was stirred at 90° C. 20 μl of a DMSO solution which had been adjusted to 1.25 M fluorescein isothiocyanate (FITC) were added to this, one droplet of pyridine and one droplet of di-n-butyltin dilaurate were added, and the mixture was stirred at 90° C. for 2 hours. After completion of the reaction, 5 ml of ethanol was added to the reaction solution, this was centrifuged at 10,000 rpm for 5 minutes, and the precipitate was recovered. Ethanol was further added, washing was performed, this was dissolved in 1 ml of ultrapure water, 1 ml of the solution was placed on a gel filtration column (PD-10), 1.5 ml of ultrapure water was passed therethrough and, thereafter, 2 ml was recovered with ultrapure water to perform purification. The resulting sample was lyophilized to obtain a fluorescently labeled product of the glucuronic acid-containing glucan (F-B, F-AcBA). Regarding a part of the resulting sample, UV absorption at 490 nm was measured. When each FITC introduction amount was obtained using uranine as a standard substance, introduction of FITC shown in Table 12 was confirmed.

TABLE 12

| SAMPLE NAME | B | AcBA2 |
| --- | --- | --- |
| FITC/Poly (M) | 2.1 | 1.4 |

Example 20

Use Example 3: Pharmacokinetic Test of Glucuronic Acid-Containing Acetylated Glucan (F-B, F-AcBA)

The concentration of the FITC-labeled glucan obtained in Example 19 (F-B, F-AcBA) was adjusted with a physiological saline to 2.6 wt %. Through a catheter part of a rat (SD, 10 week old, male) weighing around 350 g, in which a jugular vein was cannulated, 400 μl of an adjusted aqueous sample solution was injected and, thereafter, 100 μl of a physiological saline was further injected to wash the catheter. The time of sample administration was set to be 0 hour. After 1, 10, 20, 30 and 40 minutes, blood was collected through the cannula. Blood was centrifuged at 12,000 rpm for 1 minute to obtain serum of the supernatant. 10 μl of 30% trichloroacetic acid was added to 100 μl of the resulting serum to prepare a mixture. Centrifugation at 10,000 rpm for 5 minutes was performed, and 50 μl of the supernatant was recovered. This supernatant was neutralized with a 1 M phosphate buffer of pH 7, and a 5 N aqueous sodium hydroxide solution. Each sample after the neutralization was subjected to fluorescent analysis using gel filtration, and the fluorescent intensity was measured at Ex=490 nm and Em=518 nm. The results are shown in FIG. 15. A black triangle indicates F-B and a black square indicates F-AcBA. From FIG. 15 showing a change in the amount of the glucan present in blood over time, it was found that the blood retention time of the glucuronic acid-containing acetylated glucan (F-AcBA) is considerably extended as compared with an unmodified glucan (F-B).

Example 21

Production of (Three Kinds of) Reducing End-Modified Products of Glucuronic Acid-Containing Glucan

*Aquifex aeolicus* VF5-derived α-phosphorylase (14 Units/ml) produced in Production Example 1 was allowed to act on a reaction solution containing (A) reducing end-modified maltooligosaccharide (maltotriosyl α-cyclodextrin, paranitrophenylmaltopentaoside or maltosylsucrose), (B) glucuronic acid 1-phosphate, and a 100 mM sodium acetate buffer (pH 5.5) at 50° C. for 18 hours to produce (three kinds of) reducing end-modified products of a glucuronic acid-containing glucan. The reaction conditions are shown in Table 13.

The transfer ratio of glucuronic acid to three kinds of reducing end-modified maltooligosaccharides was obtained by the same method as that of Example 5. The results are shown in Table 13. As shown in Table 13, reducing end-modified products of a glucuronic acid-containing glucan were produced.

TABLE 13

Production of reducing end-modified products of glucuronic acid-containing glucan

| Kind of reducing end-modified maltooligosaccharide | Maltotriosyl α cyclodextrin | Paranitrophenylmaltopentaoside | Maltosylsucrose |
| --- | --- | --- | --- |
| Reducing end-modified maltooligosaccharide concentration (mM) | 10 | 10 | 10 |
| Glucuronic acid-1-phosphate concentration (mM) | 10 | 10 | 10 |
| Glucuronic acid-1-phosphate addition ratio (Glucuronic acid-1-phosphate/ reducing end-modified maltooligosaccharide) | 1:1 | 1:1 | 1:1 |
| Transfer ratio (%) of glucuronic acid to reducing end-modified maltooligosaccharide | 35 | 33 | 38 |

As described above, the present invention has been exemplified using preferable embodiments of the present invention, but the present invention should not be construed so as to be limited to these embodiments. It is understood that the scope of the present invention should be construed only by claims. It is understood that those skilled in the art can carry out an equivalent scope based on the description of the present invention and common technical knowledge, from the description of specific preferable embodiments of the present invention. It is understood that the content of patents, patent applications and references cited in the present specification should be incorporated herein by reference, as if the content itself is specifically described in the present specification.

INDUSTRIAL APPLICABILITY

In the novel uronic acid-containing glucan of the present invention, a uronic acid residue is bound only to a non-reducing end. Since the present uronic acid-containing glucan has uronic acid on a terminus, terminal of the glucan is charged negatively, and a physicochemical property of the glucan is changed. The present uronic acid-containing glucan can be widely utilized in foods, cosmetics, medicaments and the like.

SEQUENCE LISTING FREE TEXT

SEQ ID NO:1: Base sequence of the α-glucan phosphorylase derived from *Aquifex aeolicus* VF5.

SEQ ID NO: 2: Amino acid sequence of the α-glucan phosphorylase derived from *Aquifex aeolicus* VF5.

---

The invention claimed is:

1. A glucuronic acid-containing glucan in which a glucuronic acid residue is bound to at least one non-reducing end of a glucan, but there is no glucuronic acid residue at the positions other than the non-reducing end, wherein the glucan is a branched α-1,4 glucan or a linear α-1,4 glucan.

2. The glucuronic acid-containing glucan according to claim 1, wherein the glucan is a branched α-1,4 glucan, and a glucuronic acid residue is bound to at least one non-reducing end of a plurality of non-reducing ends of the branched α-1,4-glucan.

3. The glucuronic acid-containing glucan according to claim 2, wherein the branched α-1,4 glucan is selected from the group consisting of a branched maltooligosaccharide, a starch, amylopectin, glycogen, dextrin, an enzymatically synthesized branched glucan and highly branched cyclic dextrin.

4. A hydroxyl group-modified product of the glucuronic acid-containing glucan according to claim 1, wherein the modification is a modification on some or all of alcoholic hydroxyl groups of the glucan, and the modification is independently selected from the group consisting of hydroxyalkylation, alkylation, acetylation, carboxymethylation, sulfation and phosphorylation.

5. A reducing end-modified product of the glucuronic acid-containing glucan according to claim 1 or a hydroxyl group-modified product thereof; wherein the reducing end-modification is a modification in which a reducing end present in the glucan is bound to a substance selected from the group consisting of monosaccharides, non-reducing carbohydrates, biocompatible macromolecules, liposome constituent components, glycosides, and amine group-containing low-molecular weight substances, the hydroxyl group-modification is a modification on some or all of the alcoholic groups of the glucan, and the hydroxyl group-modification is independently selected from the group consisting of hydroxyalkylation, alkylation, acetylation, carboxymethylation, sulfation and phosphorylation.

6. A carboxyl group-modified product of the glucuronic acid-containing glucan according to claim 1, a hydroxyl group-modified product thereof or a reducing end-modified product thereof, wherein the carboxyl group-modification is a modification on some or all of carboxyl groups of the glucuronic acid residues, wherein the carboxyl group is bound to a substance selected from the group consisting of low-molecular weight organic compound, a high-molecular weight organic compound, a finely particulate carrier for a drug delivery system (DDS), and an inorganic substance; the carboxyl group-modification is attained by a reaction of the carboxyl group and a carboxyl group modifying reagent, and the carboxyl group modifying reagent has at least one amine group and at least one functional group selected from the group consisting of a cationic functional group, an anionic functional group, a hydrophobic functional group, a maleimide group, a thiol group and an aldehyde group; wherein the reducing end-modification is a modification in which a reducing end present in the glucan is bound to a substance selected from the group consisting of monosaccharides, non-reducing carbohydrates, biocompatible macromolecules, liposome constituent components, glycosides, and amine group-containing low-molecular weight substances, the hydroxyl group-modification is a modification on some or all of alcoholic hydroxyl groups of the glucan, and the hydroxyl group-modification is independently selected from the group consisting of hydroxyalkylation, alkylation, acetylation, carboxymethylation, sulfation and phosphorylation.

7. The carboxyl group-modified product according to claim 6, wherein the functional group is a cationic functional group selected from the group consisting of an amino group, a dimethylamino group, a diethylamino group, a trimethylamino group, an ammonium group, and a pyridinium group, or an anionic functional group selected from the group consisting of a phosphoric acid group, a sulfonic acid group, and a sulfuric acid group.

8. The carboxyl group-modified product according to claim 6, wherein the functional group is a hydrophobic functional group selected from the group consisting of an alkyl group and an aryl group.

9. The carboxyl group-modified product according to claim 6, wherein the functional group is selected from the group consisting of a maleimide group, a thiol group and an aldehyde group.

10. The carboxyl group-modified product according to claim 6, wherein the carboxyl group modifying reagent is selected from the group consisting of N-hydroxysuccinimide, N,N-disuccinimide carbonate, 1-hydroxybenzotriazole, N-hydroxy-5-norbornene-2,3-dicarboxylmide, N-hydroxyphthalimide, isobutyl chloroformate and 4-hydroxyphenyldimethylsulfonium methylsulfate.

11. A method for producing a glucuronic acid-containing glucan, characterized by allowing α-glucan phosphorylase to act on an aqueous solution comprising a glucan and glucuronic acid-1-phosphate.

12. The method according to claim 11, wherein the α-glucan phosphorylase has 95% or more sequence identity with an amino acid sequence of α-glucan phosphorylase derived from *Aquifex aeolicus* VF5, and has activity of transferring glucuronic acid to a non-reducing end of a glucan.

13. A medicament comprising the glucuronic acid-containing glucan according to claim 1, a hydroxyl group-modified product thereof, a reducing end-modified product thereof, or a carboxylic acid group-modified product thereof, and a medically effective ingredient.

14. The medicament according to claim 13, wherein the medically effective ingredient is selected from the group consisting of a low-molecular weight organic compound, a protein, a peptide, an antibody, an antibody fragment, a receptor, a receptor fragment, a DNA, an RNA, a siRNA and an RNA aptamer.

15. A conjugate of a medically effective ingredient and the glucuronic acid-containing glucan according to claim 1, a hydroxyl group-modified product thereof, a reducing end-modified product thereof, or a carboxylic acid group-modified product thereof, wherein the medically effective ingredient is covalently bound to at least one of carboxyl groups of the glucuronic acid residue directly.

16. A finely particulate carrier for a drug delivery system (DDS), comprising the glucuronic acid-containing glucan according to claim 1, a hydroxyl group-modified product thereof, a reducing end-modified product thereof, or a carboxylic acid group-modified product thereof.

17. The carrier according to claim 16, wherein the finely particulate carrier for a drug delivery system (DDS) is selected from the group consisting of a liposome, a virus particle, a macromolecule micelle and a nanogel composed of macromolecule bearing hydrophobic groups.

* * * * *

SEQUENCE LISTING

```
<160> NUMBER OF SEQ ID NOS: 2

<210> SEQ ID NO 1
<211> LENGTH: 2079
<212> TYPE: DNA
<213> ORGANISM: Aquifex aeolicus
<220> FEATURE:
<221> NAME/KEY: CDS
<222> LOCATION: (1)..(2079)

<400> SEQUENCE: 1 atg gaa gaa gaa aaa gta aaa gag gga ttg tgg gag tta gct tac aac      48
Met Glu Glu Glu Lys Val Lys Glu Gly Leu Trp Glu Leu Ala Tyr Asn
1               5                   10                  15 ctg tgg tgg acg tgg aat ccg ccg gct aag gaa tta ttc aga agc att      96
Leu Trp Trp Thr Trp Asn Pro Pro Ala Lys Glu Leu Phe Arg Ser Ile
            20                  25                  30 gac ccg ctt ttg tgg aag gaa act aag gaa aac ccc att gag tta ttg    144
Asp Pro Leu Leu Trp Lys Glu Thr Lys Glu Asn Pro Ile Glu Leu Leu
        35                  40                  45 agg aaa acc aaa ctc ctt gaa aac aag ctc aaa gac gaa gat ttt ata    192
Arg Lys Thr Lys Leu Leu Glu Asn Lys Leu Lys Asp Glu Asp Phe Ile
    50                  55                  60 tct cac ttc aag tac gtt tat tcc ctt tac aaa acc tac atg aac agg    240
Ser His Phe Lys Tyr Val Tyr Ser Leu Tyr Lys Thr Tyr Met Asn Arg
65                  70                  75                  80 cat tcg aaa tac gag gat acg tat aag aag cct ata gtt ttc ctg tct    288
His Ser Lys Tyr Glu Asp Thr Tyr Lys Lys Pro Ile Val Phe Leu Ser
                85                  90                  95 ccc gag tac gga ctt cac cac aca cta ctt ata tac gcg ggg gga ctg    336
Pro Glu Tyr Gly Leu His His Thr Leu Leu Ile Tyr Ala Gly Gly Leu
            100                 105                 110 ggc ttt tta gca gga gat ata ctc aag gag agc agt gac ttg gga ttt    384
Gly Phe Leu Ala Gly Asp Ile Leu Lys Glu Ser Ser Asp Leu Gly Phe
        115                 120                 125 ccg ctt ata ggt gtc ggg ttt atg tac cct cag ggc tac gta aag cag    432
Pro Leu Ile Gly Val Gly Phe Met Tyr Pro Gln Gly Tyr Val Lys Gln
    130                 135                 140 agg ata agg gtt gac gga tgg cag gaa gac ctt gac gca caa aat caa    480
Arg Ile Arg Val Asp Gly Trp Gln Glu Asp Leu Asp Ala Gln Asn Gln
145                 150                 155                 160 aag gaa tta atg ccc gtt aaa aaa gtt ctg gac aaa gaa gga aaa tgg    528
Lys Glu Leu Met Pro Val Lys Lys Val Leu Asp Lys Glu Gly Lys Trp
                165                 170                 175 ctc aag tgc tac gtt tac gta agg gat gaa aag gtt tac ttt gga gtc    576
Leu Lys Cys Tyr Val Tyr Val Arg Asp Glu Lys Val Tyr Phe Gly Val
            180                 185                 190 tgg gaa gtt aac gtg gga aag aca aag ctc tac ctt ctt gac acg aac    624
Trp Glu Val Asn Val Gly Lys Thr Lys Leu Tyr Leu Leu Asp Thr Asn
        195                 200                 205
```

```
gta gag gaa aat act ccc tgg aac agg gaa ata tcc tca aga ctc tac      672
Val Glu Glu Asn Thr Pro Trp Asn Arg Glu Ile Ser Ser Arg Leu Tyr
    210                 215                 220 gtt ccg gac aaa gac ctg agg tta aga caa cag ata gtt ctt ggt ttt      720
Val Pro Asp Lys Asp Leu Arg Leu Arg Gln Gln Ile Val Leu Gly Phe
225                 230                 235                 240 ggc acc gta ata ctc ctt gaa aag ctg ggc att gat gca gga ggt ttt      768
Gly Thr Val Ile Leu Leu Glu Lys Leu Gly Ile Asp Ala Gly Gly Phe
                245                 250                 255 cac ata aac gaa gat tat ccc tcg ttc gtg ttc ctt gca gaa ata ttt      816
His Ile Asn Glu Asp Tyr Pro Ser Phe Val Phe Leu Ala Glu Ile Phe
            260                 265                 270 aaa ctt cta aaa aaa ggt ctg acc tgg gat aag gcg ata gaa gaa gta      864
Lys Leu Leu Lys Lys Gly Leu Thr Trp Asp Lys Ala Ile Glu Glu Val
        275                 280                 285 aga aag att tct ctc ttt acc acg cac aca cca cta cgg gtt gcc gta      912
Arg Lys Ile Ser Leu Phe Thr Thr His Thr Pro Leu Arg Val Ala Val
    290                 295                 300 aat act tat ccc ttc cac atg ata gag gaa cag ttt cta ttc gtt aag      960
Asn Thr Tyr Pro Phe His Met Ile Glu Glu Gln Phe Leu Phe Val Lys
305                 310                 315                 320 gat gtt tac gga ata gac gta aag aaa gtt ctg gaa ctc gga acg aat     1008
Asp Val Tyr Gly Ile Asp Val Lys Lys Val Leu Glu Leu Gly Thr Asn
                325                 330                 335 cct gaa gac cct tcg gag ggt ttt aac agt acg att atg tcc ctc aga     1056
Pro Glu Asp Pro Ser Glu Gly Phe Asn Ser Thr Ile Met Ser Leu Arg
            340                 345                 350 ctc gca aag tac gta aac gca gtg agt aaa aga cat caa gaa gtt tca     1104
Leu Ala Lys Tyr Val Asn Ala Val Ser Lys Arg His Gln Glu Val Ser
        355                 360                 365 agc aag atg tgg agt ttt tta ttt aaa gaa aag gag aat cca ata gat     1152
Ser Lys Met Trp Ser Phe Leu Phe Lys Glu Lys Glu Asn Pro Ile Asp
    370                 375                 380 tac gta acg aac ggt gtt cac ttt ccc aca tgg att tgt tca gat ttg     1200
Tyr Val Thr Asn Gly Val His Phe Pro Thr Trp Ile Cys Ser Asp Leu
385                 390                 395                 400 aga aga ctg tac gag gag tat ttg gga gag aac ttt gtg gaa ctt cac     1248
Arg Arg Leu Tyr Glu Glu Tyr Leu Gly Glu Asn Phe Val Glu Leu His
                405                 410                 415 gac cac aag tct ctg tgg gaa tta ata aga gac ata ccc gac gaa gaa     1296
Asp His Lys Ser Leu Trp Glu Leu Ile Arg Asp Ile Pro Asp Glu Glu
            420                 425                 430 ctg tgg gaa tat cac ata aga aat aaa gaa aga ctt att gag cac ata     1344
Leu Trp Glu Tyr His Ile Arg Asn Lys Glu Arg Leu Ile Glu His Ile
        435                 440                 445 aaa gac agg gca agg gaa agg tgg gtc aag gaa aaa gcg gat cct tca     1392
Lys Asp Arg Ala Arg Glu Arg Trp Val Lys Glu Lys Ala Asp Pro Ser
    450                 455                 460 atc ctt atg gcc gaa ggt ctg ttc ctt gat tct gac gtt ctt acg gtc     1440
Ile Leu Met Ala Glu Gly Leu Phe Leu Asp Ser Asp Val Leu Thr Val
465                 470                 475                 480 ggt ttt gcg agg agg atg acc ggt tac aaa aga ccg gat ctt ata ttc     1488
Gly Phe Ala Arg Arg Met Thr Gly Tyr Lys Arg Pro Asp Leu Ile Phe
                485                 490                 495 acg gat gta gaa cgc tta aaa aag ata gtg aat gat tcg gaa aga cct     1536
Thr Asp Val Glu Arg Leu Lys Lys Ile Val Asn Asp Ser Glu Arg Pro
            500                 505                 510 gtt cag ata ata ttc gcg gga aag gct cat ccg gct gat atc gaa ggg     1584
Val Gln Ile Ile Phe Ala Gly Lys Ala His Pro Ala Asp Ile Glu Gly
        515                 520                 525
```

-continued

| | | | | | | | | | | | | | | | |
|---|---|---|---|---|---|---|---|---|---|---|---|---|---|---|---|
| aaa | aag | ata | atc | cag | aga | ata | ttt | aac | ttt | gcg | aaa | gat | ccg | gaa | ttt | 1632 |
| Lys | Lys | Ile | Ile | Gln | Arg | Ile | Phe | Asn | Phe | Ala | Lys | Asp | Pro | Glu | Phe |
| | 530 | | | | 535 | | | | 540 | | | | | |

| ggg | gga | aga | ata | gct | ttc | gtt | gaa | gat | tac | gac | gaa | ctc | ctt | gcc | cat | 1680 |
| Gly | Gly | Arg | Ile | Ala | Phe | Val | Glu | Asp | Tyr | Asp | Glu | Leu | Leu | Ala | His |
| 545 | | | | 550 | | | | | 555 | | | | 560 |

| tac | atg | gtg | agg | ggt | gtg | gac | gta | tgg | ttg | aac | aac | cct | ctt | cct | ccc | 1728 |
| Tyr | Met | Val | Arg | Gly | Val | Asp | Val | Trp | Leu | Asn | Asn | Pro | Leu | Pro | Pro |
| | | | 565 | | | | | 570 | | | | 575 |

| ctt | gaa | gcc | tgc | ggg | aca | agc | ggt | atg | aaa | gct | tct | atg | aac | gga | gtg | 1776 |
| Leu | Glu | Ala | Cys | Gly | Thr | Ser | Gly | Met | Lys | Ala | Ser | Met | Asn | Gly | Val |
| | | 580 | | | | | 585 | | | | 590 |

| ctt | cac | ctt | tca | ata | ctt | gac | ggt | tgg | tgg | att | gag | ggt | tat | aac | gga | 1824 |
| Leu | His | Leu | Ser | Ile | Leu | Asp | Gly | Trp | Trp | Ile | Glu | Gly | Tyr | Asn | Gly |
| | | 595 | | | | 600 | | | | 605 |

| aag | aac | ggt | tgg | gct | ttc | gga | gat | tac | gaa | gtt | gaa | gga | gac | agg | aac | 1872 |
| Lys | Asn | Gly | Trp | Ala | Phe | Gly | Asp | Tyr | Glu | Val | Glu | Gly | Asp | Arg | Asn |
| 610 | | | | 615 | | | | 620 |

| aga | gcg | gat | gcg | gag | gcc | att | tac | aac | atc | ctt | gag | aat | gaa | gta | atc | 1920 |
| Arg | Ala | Asp | Ala | Glu | Ala | Ile | Tyr | Asn | Ile | Leu | Glu | Asn | Glu | Val | Ile |
| 625 | | | | 630 | | | | | 635 | | | | 640 |

| ccc | ctt | tat | tac | gaa | agg | gac | gag | agg | gga | gtg | cca | gtt | aag | tgg | ata | 1968 |
| Pro | Leu | Tyr | Tyr | Glu | Arg | Asp | Glu | Arg | Gly | Val | Pro | Val | Lys | Trp | Ile |
| | | | 645 | | | | | 650 | | | | 655 |

| agt | atg | atg | aag | gaa | gct | ata | aaa | agc | att | acc | cct | aac | ttt | tgc | tcc | 2016 |
| Ser | Met | Met | Lys | Glu | Ala | Ile | Lys | Ser | Ile | Thr | Pro | Asn | Phe | Cys | Ser |
| | | 660 | | | | | 665 | | | | 670 |

| aga | agg | atg | tta | aaa | gat | tac | ata | aat | aag | ttc | tat | tca | aaa | att | tta | 2064 |
| Arg | Arg | Met | Leu | Lys | Asp | Tyr | Ile | Asn | Lys | Phe | Tyr | Ser | Lys | Ile | Leu |
| | | 675 | | | | 680 | | | | 685 |

| aag | gag | gag | gga | tga | | | | | | | | | | | | 2079 |
| Lys | Glu | Glu | Gly |
| | 690 |

<210> SEQ ID NO 2
<211> LENGTH: 692
<212> TYPE: PRT
<213> ORGANISM: Aquifex aeolicus

<400> SEQUENCE: 2

Met Glu Glu Lys Val Lys Glu Gly Leu Trp Glu Leu Ala Tyr Asn
1               5                   10                  15

Leu Trp Trp Thr Trp Asn Pro Pro Ala Lys Glu Leu Phe Arg Ser Ile
            20                  25                  30

Asp Pro Leu Leu Trp Lys Glu Thr Lys Glu Asn Pro Ile Glu Leu Leu
        35                  40                  45

Arg Lys Thr Lys Leu Leu Glu Asn Lys Leu Lys Asp Glu Asp Phe Ile
    50                  55                  60

Ser His Phe Lys Tyr Val Tyr Ser Leu Tyr Lys Thr Tyr Met Asn Arg
65                  70                  75                  80

His Ser Lys Tyr Glu Asp Thr Tyr Lys Lys Pro Ile Val Phe Leu Ser
                85                  90                  95

Pro Glu Tyr Gly Leu His His Thr Leu Leu Ile Tyr Ala Gly Gly Leu
            100                 105                 110

Gly Phe Leu Ala Gly Asp Ile Leu Lys Glu Ser Ser Asp Leu Gly Phe
        115                 120                 125

Pro Leu Ile Gly Val Gly Phe Met Tyr Pro Gln Gly Tyr Val Lys Gln
    130                 135                 140

Arg Ile Arg Val Asp Gly Trp Gln Glu Asp Leu Asp Ala Gln Asn Gln

```
            145                 150                 155                 160
Lys Glu Leu Met Pro Val Lys Lys Val Leu Asp Lys Glu Gly Lys Trp
                        165                 170                 175

Leu Lys Cys Tyr Val Tyr Val Arg Asp Glu Lys Val Tyr Phe Gly Val
                180                 185                 190

Trp Glu Val Asn Val Gly Lys Thr Lys Leu Tyr Leu Asp Thr Asn
            195                 200                 205

Val Glu Glu Asn Thr Pro Trp Asn Arg Glu Ile Ser Ser Arg Leu Tyr
        210                 215                 220

Val Pro Asp Lys Asp Leu Arg Leu Arg Gln Gln Ile Val Leu Gly Phe
225                 230                 235                 240

Gly Thr Val Ile Leu Leu Glu Lys Leu Gly Ile Asp Ala Gly Gly Phe
                    245                 250                 255

His Ile Asn Glu Asp Tyr Pro Ser Phe Val Phe Leu Ala Glu Ile Phe
                260                 265                 270

Lys Leu Leu Lys Lys Gly Leu Thr Trp Asp Lys Ala Ile Glu Glu Val
                275                 280                 285

Arg Lys Ile Ser Leu Phe Thr Thr His Thr Pro Leu Arg Val Ala Val
        290                 295                 300

Asn Thr Tyr Pro Phe His Met Ile Glu Glu Gln Phe Leu Phe Val Lys
305                 310                 315                 320

Asp Val Tyr Gly Ile Asp Val Lys Lys Val Leu Glu Leu Gly Thr Asn
                    325                 330                 335

Pro Glu Asp Pro Ser Glu Gly Phe Asn Ser Thr Ile Met Ser Leu Arg
                340                 345                 350

Leu Ala Lys Tyr Val Asn Ala Val Ser Lys Arg His Gln Glu Val Ser
                355                 360                 365

Ser Lys Met Trp Ser Phe Leu Phe Lys Glu Lys Glu Asn Pro Ile Asp
        370                 375                 380

Tyr Val Thr Asn Gly Val His Phe Pro Thr Trp Ile Cys Ser Asp Leu
385                 390                 395                 400

Arg Arg Leu Tyr Glu Glu Tyr Leu Gly Glu Asn Phe Val Glu Leu His
                    405                 410                 415

Asp His Lys Ser Leu Trp Glu Leu Ile Arg Asp Ile Pro Asp Glu Glu
                420                 425                 430

Leu Trp Glu Tyr His Ile Arg Asn Lys Glu Arg Leu Ile Glu His Ile
                435                 440                 445

Lys Asp Arg Ala Arg Glu Arg Trp Val Lys Lys Ala Asp Pro Ser
        450                 455                 460

Ile Leu Met Ala Glu Gly Leu Phe Leu Asp Ser Asp Val Leu Thr Val
465                 470                 475                 480

Gly Phe Ala Arg Arg Met Thr Gly Tyr Lys Arg Pro Asp Leu Ile Phe
                    485                 490                 495

Thr Asp Val Glu Arg Leu Lys Lys Ile Val Asn Asp Ser Glu Arg Pro
                500                 505                 510

Val Gln Ile Ile Phe Ala Gly Lys Ala His Pro Ala Asp Ile Glu Gly
                515                 520                 525

Lys Lys Ile Ile Gln Arg Ile Phe Asn Phe Ala Lys Asp Pro Glu Phe
        530                 535                 540

Gly Gly Arg Ile Ala Phe Val Glu Asp Tyr Asp Glu Leu Leu Ala His
545                 550                 555                 560

Tyr Met Val Arg Gly Val Asp Val Trp Leu Asn Asn Pro Leu Pro Pro
                    565                 570                 575
```

```
-continued

Leu Glu Ala Cys Gly Thr Ser Gly Met Lys Ala Ser Met Asn Gly Val
            580                 585                 590

Leu His Leu Ser Ile Leu Asp Gly Trp Trp Ile Glu Gly Tyr Asn Gly
        595                 600                 605

Lys Asn Gly Trp Ala Phe Gly Asp Tyr Glu Val Glu Gly Asp Arg Asn
    610                 615                 620

Arg Ala Asp Ala Glu Ala Ile Tyr Asn Ile Leu Glu Asn Glu Val Ile
625                 630                 635                 640

Pro Leu Tyr Tyr Glu Arg Asp Glu Arg Gly Val Pro Val Lys Trp Ile
            645                 650                 655

Ser Met Met Lys Glu Ala Ile Lys Ser Ile Thr Pro Asn Phe Cys Ser
            660                 665                 670

Arg Arg Met Leu Lys Asp Tyr Ile Asn Lys Phe Tyr Ser Lys Ile Leu
            675                 680                 685

Lys Glu Glu Gly
        690
```